United States Patent
Ohta et al.

(10) Patent No.: US 8,798,236 B2
(45) Date of Patent: Aug. 5, 2014

(54) RADIOGRAPHIC IMAGE CAPTURING APPARATUS AND RADIOGRAPHIC IMAGE CAPTURING SYSTEM

(75) Inventors: Yasunori Ohta, Kanagawa-ken (JP); Naoyuki Nishino, Kanagawa-ken (JP); Haruyasu Nakatsugawa, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 775 days.

(21) Appl. No.: 12/929,501

(22) Filed: Jan. 28, 2011

(65) Prior Publication Data

US 2011/0188633 A1    Aug. 4, 2011

(30) Foreign Application Priority Data

Jan. 29, 2010 (JP) ................................ 2010-019635
Feb. 15, 2010 (JP) ................................ 2010-030543
Feb. 23, 2010 (JP) ................................ 2010-037586
Dec. 10, 2010 (JP) ................................ 2010-275185
Dec. 10, 2010 (JP) ................................ 2010-275187
Dec. 10, 2010 (JP) ................................ 2010-275188

(51) Int. Cl.
*H05G 1/10* (2006.01)
*H05G 1/64* (2006.01)

(52) U.S. Cl.
USPC ...... 378/102; 378/98.8; 378/101; 250/370.09

(58) Field of Classification Search
USPC .......... 378/91, 98.8, 101, 102, 115, 116, 117, 378/189; 250/370.09
See application file for complete search history.

(56) References Cited

U.S. PATENT DOCUMENTS

| 4,979,198 A | 12/1990 | Malcolm et al. |
| 5,514,873 A | 5/1996 | Schulze-Ganzlin et al. |
| 5,844,961 A * | 12/1998 | McEvoy et al. ............. 378/98.8 |
| 5,877,501 A * | 3/1999 | Ivan et al. ................ 250/370.09 |

(Continued)

FOREIGN PATENT DOCUMENTS

| JP | 10-225450 | 8/1998 |
| JP | 11-104117 | 4/1999 |

(Continued)

OTHER PUBLICATIONS

National Institute of Advanced Industrial Science & Technology, "Development of Portable X-ray Sources Using Carbon Nanostructures" [online], Mar. 19, 2009, pp. 1-4.

(Continued)

*Primary Examiner* — Allen C. Ho
(74) *Attorney, Agent, or Firm* — Jean C. Edwards; Edwards Neils PLLC

(57) ABSTRACT

A radiographic image capturing apparatus has a radiation source device including a radiation source, and a detector device including a radiation detector. At least one of the radiation source device and the detector device includes an electric power supply limiting unit for limiting supply of electric power. The electric power supply limiting unit has an activator/deactivator for determining activation or deactivation of supply of electric power between the radiation source device and the detector device, based on a present position of a corresponding one of the radiation source device and the detector device, or based on distance between the radiation source device and the detector device, and an electric power supply activator for enabling supply of electric power between the radiation source device and the detector device, if the activator/deactivator determines activation of supply of electric power between the radiation source device and the detector device.

30 Claims, 49 Drawing Sheets

(56) References Cited

U.S. PATENT DOCUMENTS

| | | | |
|---|---|---|---|
| 6,999,558 B2* | 2/2006 | Okoda | 378/102 |
| 7,015,478 B2* | 3/2006 | Yamamoto | 250/370.09 |
| 7,016,467 B2* | 3/2006 | Brooks | 378/102 |
| 7,356,121 B2* | 4/2008 | Schwarz | 378/101 |
| 7,545,914 B2* | 6/2009 | Kito et al. | 378/98.8 |
| 7,629,587 B2 | 12/2009 | Yagi et al. | |
| 7,664,228 B2* | 2/2010 | Yi | 378/101 |
| 7,768,002 B2 | 8/2010 | Kitamura et al. | |
| 7,847,258 B2 | 12/2010 | Yaegashi et al. | |
| 7,864,923 B2* | 1/2011 | Ohta et al. | 378/102 |
| 7,874,728 B2* | 1/2011 | Fan | 378/198 |
| 7,991,119 B2* | 8/2011 | Yoshida et al. | 378/114 |
| 8,080,802 B2* | 12/2011 | Nishino et al. | 250/370.08 |
| 8,193,509 B2* | 6/2012 | Niekawa et al. | 250/370.09 |
| 2007/0135182 A1 | 6/2007 | Hanif et al. | |
| 2008/0240343 A1 | 10/2008 | Jabri et al. | |
| 2009/0247199 A1 | 10/2009 | Oodachi et al. | |
| 2010/0163737 A1 | 7/2010 | Masuda et al. | |

FOREIGN PATENT DOCUMENTS

| | | | |
|---|---|---|---|
| JP | 2000-105297 | | 4/2000 |
| JP | 2007-103016 | | 4/2007 |
| JP | 2007-165960 | A | 6/2007 |
| JP | 2007-222604 | | 9/2007 |
| JP | 2007-530979 | | 11/2007 |
| JP | 2008-118285 | A | 5/2008 |
| JP | 2008-253762 | A | 10/2008 |
| JP | 2009-028449 | | 2/2009 |
| JP | 2009-32854 | | 2/2009 |
| JP | 2009-050689 | A | 3/2009 |
| JP | 2009-065347 | A | 3/2009 |
| JP | 2009-162491 | A | 7/2009 |
| JP | 2009-212389 | | 9/2009 |
| JP | 2009-239640 | A | 10/2009 |
| WO | WO 2006/101468 A1 | | 9/2006 |
| WO | WO-2008-146602 A1 | | 12/2008 |

OTHER PUBLICATIONS

Eisuke Hiro, et al.,"Applying Pyroelectric Crystal to Small High Energy X-Ray Source", Advances in X-Ray Chemical Analysis, 2010, pp. 195-200, Japan, 41.

Dev. by the Univ. of Tokyo, partial Eng. translation of "Arrival of Contactless Power Transmission Sheet Expected to be Embedded in Walls . . . " [online], Dec. 4, 2006, pp. 1-3.

Nikkei Electronics, partial Eng. translation of "Development of Wireless Power Transmission Technology, a 60-W Lamp Turned on in Experiment", Dec. 3, 2007, pp. 117-128.

Rejection of the Application issued by the Japanese Patent Office (JPO) on Feb. 12, 2014 in connection with Japanese Patent Application No. 2010-275188.

Rejection of Application issued by the JPO on Feb. 12, 2014 in connection with Japanese Patent Application No. 2010-275187.

* cited by examiner

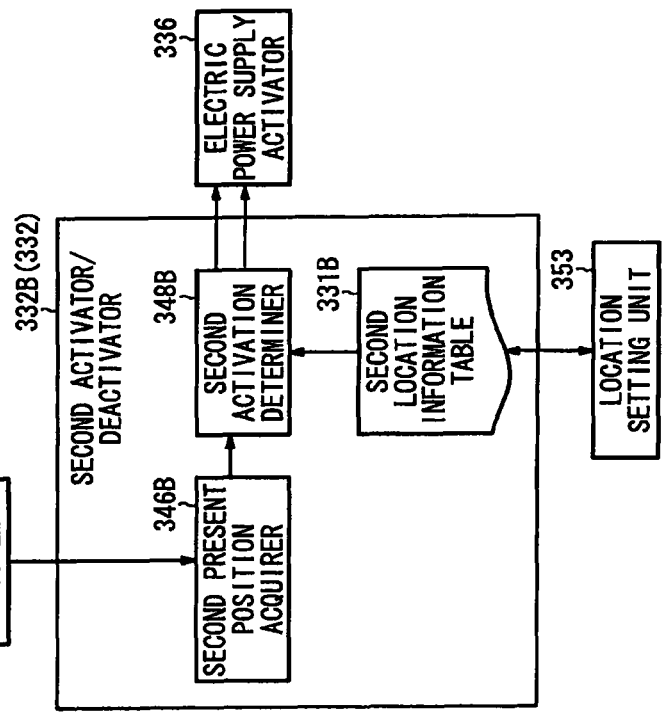
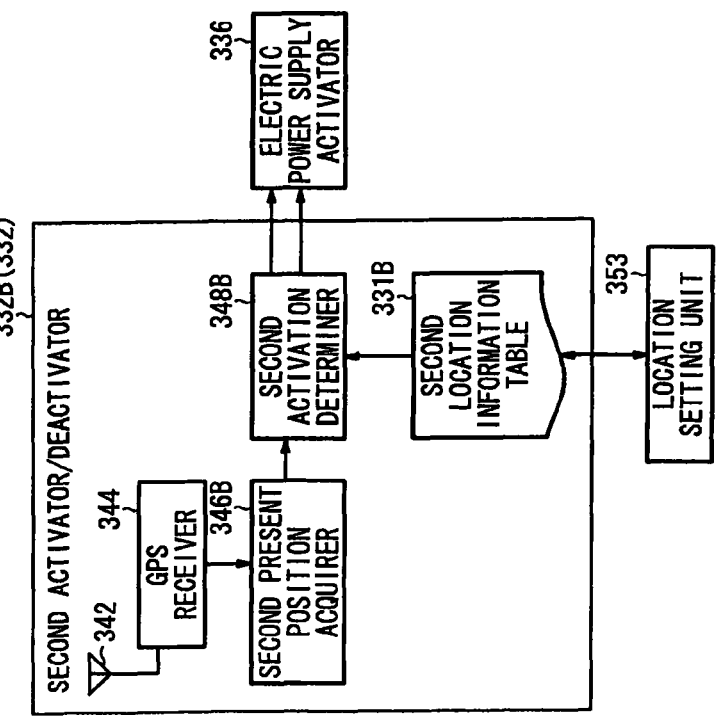

RADIOGRAPHIC IMAGE CAPTURING APPARATUS AND RADIOGRAPHIC IMAGE CAPTURING SYSTEM

CROSS-REFERENCE TO RELATED APPLICATION

This application is based upon and claims the benefit of priority from Japanese Patent Applications No. 2010-019635 filed on Jan. 29, 2010, No. 2010-030543 filed on Feb. 15, 2010, No. 2010-037586 filed on Feb. 23, 2010, No. 2010-275185 filed on Dec. 10, 2010, No. 2010-275187 filed on Dec. 10, 2010 and No. 2010-275188 filed on Dec. 10, 2010, of which the contents are incorporated herein by reference.

BACKGROUND OF THE INVENTION

1. Field of the Invention

The present invention relates to a radiographic image capturing apparatus and a radiographic image capturing system. More particularly, the present invention concerns a radiographic image capturing apparatus preferably for use as a portable radiographic image capturing apparatus, which can be carried outdoors by an operator, and a radiographic image capturing system.

2. Description of the Related Art

In the medical field, there have widely been used radiographic image capturing apparatus, which apply radiation to a subject and guide radiation that has passed through the subject to a radiation conversion panel (radiation detector), which captures a radiographic image from such radiation. Known forms of radiation conversion panels include conventional radiation film for recording a radiographic image by way of exposure, and stimulable phosphor panels for storing radiation energy representing a radiographic image in a phosphor, and reproducing the radiographic image as stimulated light by applying stimulating light to the phosphor. Radiation film with the recorded radiographic image is supplied to a developing device to develop the radiographic image, or the stimulable phosphor panel is supplied to a reading device to read the radiographic image as a visible image.

In an operating room or the like, for the purpose of quickly and appropriately treating patients, it is necessary to read a recorded radiographic image immediately from a radiation conversion panel after the radiographic image has been captured. As a radiation detector which meets such a requirement, there have been developed a radiation detector of a direct conversion type (electronic cassette) having a solid-state detector for converting radiation directly into electric signals, and a radiation detector of an indirect conversion type (electronic cassette) having a scintillator for temporarily converting radiation into visible light and a solid-state detector for converting such visible light into electric signals (see U.S. Pat. No. 5,514,873).

Such radiographic image capturing apparatus are developed on the assumption that they will be used to capture radiographic images of patients in medical organizations.

There are potential demands for capturing radiographic images outside of medical organizations. To meet such demands, radiographic image capturing apparatus, which are mounted on motor vehicles used to perform medical check-ups, have been proposed in the art. However, such proposed radiographic image capturing apparatus, which are disposed on medical checkup motor vehicles, are relatively large in size. Needs have arisen for capturing radiographic images of persons who suffer from natural disasters at disaster sites, or persons who are receiving home-care services at their homes.

However, existing medical checkup motor vehicles cannot be used in the former applications, since it is difficult to get to disaster sites. Although existing medical checkup motor vehicles may be driven to the homes of persons who are receiving home-care services, the image capturing process is highly burdensome to people to be imaged, because they have to be taken from their homes into the medical checkup motor vehicle in order to capture radiographic images of such people. Therefore, there have been demands for small-size portable radiographic image capturing apparatus for use at natural disaster sites or at homes receiving home-care services.

There has been developed a portable radiographic image capturing apparatus, which can be folded into a compact form in its entirety (see Japanese Laid-Open Patent Publication No. 2007-530979 (PCT)). In addition, radiation sources comprising field-electron-emission-type electron sources based on carbon nanotube (CNT) technology have also been developed (see Japanese Laid-Open Patent Publication No. 2007-103016, and AIST: Press Release, "Development of Portable X-ray Sources Using Carbon Nanostructures" [online], Mar. 19, 2009, National Institute of Advanced Industrial Science and Technology, Internet <URL:http://www.aist.go.jp/aist_j/press_release/pr2009/pr20090319/pr20090319.html> (hereinafter referred to as "Document 1"). It is expected that small-size, lightweight radiographic image capturing apparatus including radiation sources will become available in the art. Further, a portable size and high energy X-ray source was developed by using $LiTaO_3$ that is a typical pyroelectric crystal (see "Applying Pyroelectric Crystal to Small High Energy X-Ray Source", Advances in X-Ray Chemical Analysis, Japan, 41, 2010, pages 195-200 (hereinafter referred to as "Document 2")).

Wireless electric power transmitting schemes are known from IEDM Plenary Talk, "Arrival of Contactless Power Transmission Sheet Expected to be Embedded in Walls and Floors, developed by the University of Tokyo" [online], Dec. 4, 2006, Internet <URL:http://techon.nikkeibp.co.jp/article/NEWS/20061204/124943/> (hereinafter referred to as "Document 3"), and Nikkei Electronics, "Development of Wireless Power Transmission Technology, a 60-W Lamp Turned on in Experiment," Dec. 3, 2007, pages 117-128 (hereinafter referred to as "Document 4"). The process disclosed in Document 3 transmits electric power based on electromagnetic induction from a primary coil embedded in a contactless power transmission sheet. The process disclosed in Document 4 is a wireless power transmission technology based on magnetic field resonance between two LC resonators.

If a small-size radiation source can be reduced in size as disclosed in Japanese Laid-Open Patent Publication No. 2007-530979 (PCT), Japanese Laid-Open Patent Publication No. 2007-103016, Document 1, and Document 2, then the radiation source may be combined with an electronic cassette as disclosed in U.S. Pat. No. 5,514,873 in order to reduce the size and weight of the radiographic image capturing apparatus, which includes a radiation source and an electronic cassette, thereby allowing the radiographic image capturing apparatus to be moved with ease. In other words, a portable radiographic image capturing apparatus can be realized.

However, since such a portable radiographic image capturing apparatus mainly is used outdoors, a problem arises as to the availability of a power supply therefor. One solution would be to carry separate batteries together with the portable radiographic image capturing apparatus. More specifically, it is necessary to prepare a battery dedicated for the radiation source, a battery dedicated for the electronic cassette, and a battery dedicated for a controller (personal computer), etc., for use with the portable radiographic image capturing apparatus. In addition to such batteries, backup batteries also need to be carried, in case images have to be recaptured or additional images have to be captured. As a result, the entire radiographic image capturing system to be carried around is liable to be of an increased size and weight, thus reducing the ease (including portability) with which the radiographic image capturing system can be used.

SUMMARY OF THE INVENTION

An object of the present invention is to provide a radiographic image capturing apparatus and a radiographic image capturing system, which are capable of supplying electric power to a radiation source and a radiation detector even outdoors, reducing consumption of electric power, and minimizing the number batteries used therein, which can be used easily and efficiently both inside and outside of places such as medical organizations, accident sites, disaster sites, medical checkup sites, home-care service sites, etc., which can reduce consumption of electric power by separately storing and carrying the radiation source and the radiation detector, and which can prevent the radiation source and the radiation detector from being stolen as a set.

According to an aspect of the present invention, there is provided a radiographic image capturing apparatus comprising a radiation source device including a radiation source for outputting radiation, and a detector device including a radiation detector for detecting radiation that is transmitted through a subject when the subject is irradiated with radiation by the radiation source, and converting the detected radiation into a radiographic image, at least one of the radiation source device and the detector device having an electric power supply limiting unit for limiting supply of electric power, the electric power supply limiting unit comprising an activator/deactivator for determining activation or deactivation of supply of electric power between the radiation source device and the detector device, based on a present position of a corresponding one of the radiation source device and the detector device, or based on a distance between the radiation source device and the detector device, and an electric power supply activator for enabling supply of electric power between the radiation source device and the detector device, if the activator/deactivator determines activation of supply of electric power between the radiation source device and the detector device.

In the radiographic image capturing apparatus, the activator/deactivator comprises a present position acquirer for acquiring the present position of the corresponding one of the radiation source device and the detector device, and a determiner for determining whether or not the acquired present position is outside of a medical organization, and the electric power supply activator enables supply of electric power between the radiation source device and the detector device, if the determiner judges that the acquired present position is outside of the medical organization.

In the radiographic image capturing apparatus, the activator/deactivator comprises a present position acquirer for acquiring the present position of the corresponding one of the radiation source device and the detector device, and a determiner for determining whether or not the acquired present position is in a preset location, and the electric power supply activator enables supply of electric power between the radiation source device and the detector device, if the determiner judges that the acquired present position is in the preset location.

In the radiographic image capturing apparatus, the activator/deactivator comprises a determiner for determining whether or not the distance between the radiation source device and the detector device satisfies a certain condition, and the electric power supply activator enables supply of electric power between the radiation source device and the detector device, if the determiner judges that the distance satisfies the certain condition.

According to another aspect of the present invention, there is also provided a radiographic image capturing system comprising a radiation source device including a radiation source for outputting radiation, a detector device including a radiation detector for detecting radiation that is transmitted through a subject when the subject is irradiated with radiation by the radiation source, and converting the detected radiation into a radiographic image, an activator/deactivator for determining activation or deactivation of supply of electric power between the radiation source device and the detector device, based on a present position of at least one of the radiation source device and the detector device, or based on a distance between the radiation source device and the detector device, and an electric power supply activator for enabling supply of electric power between the radiation source device and the detector device, if the activator/deactivator determines activation of supply of electric power between the radiation source device and the detector device.

In the radiographic image capturing system, the activator/deactivator comprises a present position acquirer for acquiring the present position of at least one of the radiation source device and the detector device, and a determiner for determining whether or not the acquired present position is outside of a medical organization, and the electric power supply activator enables supply of electric power between the radiation source device and the detector device, if the determiner judges that the acquired present position is outside of the medical organization.

In the radiographic image capturing system, the activator/deactivator comprises a present position acquirer for acquiring the present position of at least one of the radiation source device and the detector device, and a determiner for determining whether or not the acquired present position is in a preset location, and the electric power supply activator enables supply of electric power between the radiation source device and the detector device, if the determiner judges that the acquired present position is in the preset location.

In the radiographic image capturing system, the activator/deactivator comprises a determiner for determining whether or not the distance between the radiation source device and the detector device satisfies a certain condition, and the electric power supply activator enables supply of electric power between the radiation source device and the detector device, if the determiner judges that the distance satisfies the certain condition.

According to the present invention, the radiation source and the radiation detector can be supplied with electric power even if the radiographic image capturing apparatus is used outdoors. Batteries that need to be included in the radiographic image capturing apparatus are minimized. Therefore, the radiographic image capturing apparatus is convenient for use outside of a medical organization, or in a preset location such as a medical organization, or in any of various other sites including an accident site, a disaster site, a medical checkup site, a home-care service site, etc. The radiation source and the radiation detector can separately be stored and carried for reduced electric power consumption, as well as for protection against being stolen as a set.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 16A is a block diagram of a second activator/deactivator according to a first mode;

FIG. 16B is a block diagram of a fourth activator/deactivator;

DESCRIPTION OF THE PREFERRED EMBODIMENTS

Figure 1:
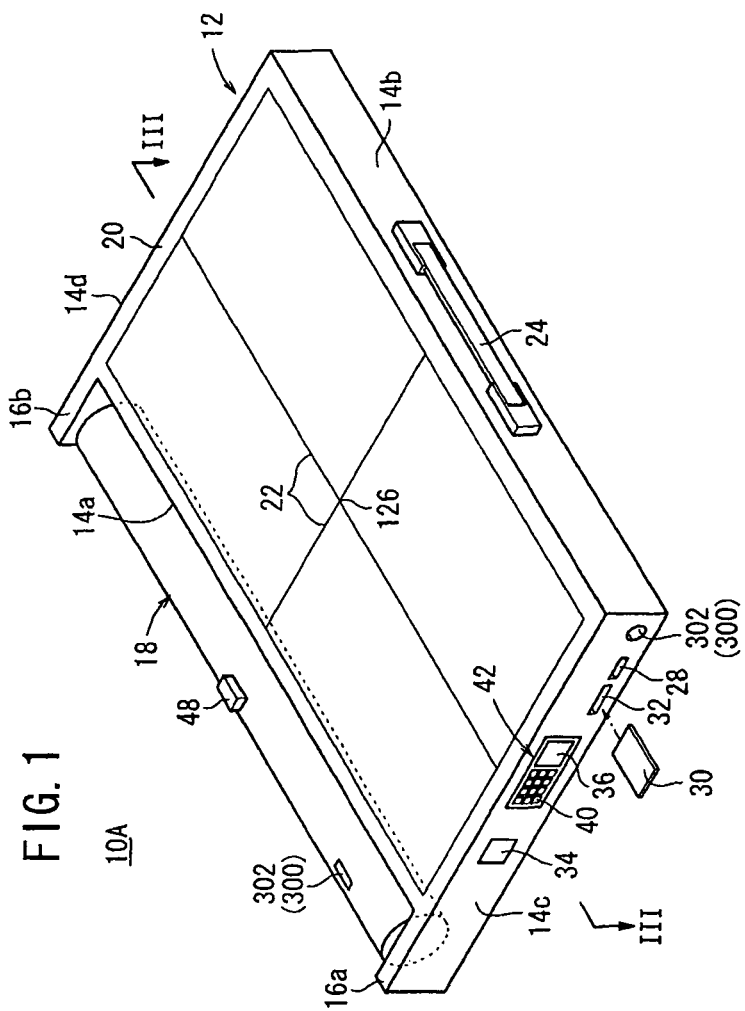
FIG. 1 is a perspective view of a radiographic image capturing apparatus (first radiographic image capturing apparatus) according to a first embodiment of the present invention.

Like or corresponding parts are denoted by like or corresponding reference characters throughout the views.

Figure 2:
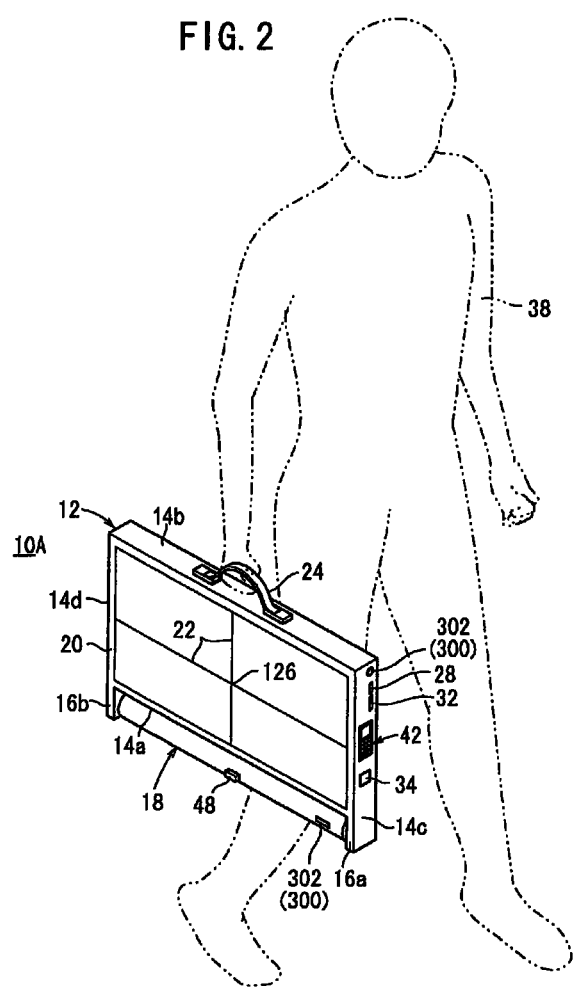
FIG. 2 is a perspective view showing the manner in which the first radiographic image capturing apparatus is carried.

As shown in FIGS. 1 and 2, a radiographic image capturing apparatus 10A according to a first embodiment of the present invention, which hereinafter will be referred to as a "first radiographic image capturing apparatus 10A," includes a cassette (detector device) 12 having a substantially rectangular outer contour shaped as a housing, and which is made of a material permeable to radiation 46 (see FIG. 5), and a cylindrical radiation source device 18 held in the cassette 12 by a pair of holders 16a, 16b, which project outwardly from opposite ends of one side 14a of the cassette 12.

The cassette 12 has crisscross guide lines 22 disposed on a surface (irradiated surface) 20 thereof, which serve as a reference for an image capturing area and an image capturing position. The cassette 12 also has a grip 24 on another side 14b thereof remote from the one side 14a. The cassette 12 has two other sides 14c, 14d extending perpendicular to and between the sides 14a, 14b, which are opposite to each other. On the side 14c, there are disposed a USB (Universal Serial Bus) terminal 28 as an interface means for sending information to and receiving information from an external device, a card slot 32 for insertion of a memory card 30 therein, and an unlocking button 34 to be described later. The side 14c also supports thereon a mobile terminal 42, which is detachable from the cassette 12. The mobile terminal 42 includes a display unit 36 and an operating unit 40 having a number of control buttons operable by a doctor or radiological technician (hereinafter referred to as an "operator") 38 who handles the first radiographic image capturing apparatus 10A. The radiation source device 18 has an exposure switch 48, which can be operated by the operator 38 in order to cause a radiation source 44 (see FIG. 5), which shall be descried later, to start emitting radiation 46.

FIGS. 1 and 2 show the first radiographic image capturing apparatus 10A, which is carried by the operator 38. When the first radiographic image capturing apparatus 10A is carried, the radiation source device 18 and the cassette 12 are integrally joined to each other. The operator 38 grips the grip 24 and carries the first radiographic image capturing apparatus 10A to a desired site, such as an accident site, a disaster site, a medical checkup site, or a home receiving home-care services outside of a medical organization, or somewhere inside of a medical organization. When the operator 38 arrives at the site, the operator 38 operates the first radiographic image capturing apparatus 10A in order to capture radiographic images of a victim at the accident site or the disaster site, or an examinee at the medical checkup site, or a person receiving home-care services at home. The victim or person whose radiographic images are to be captured will hereinafter be referred to as a "subject" 50 (see FIG. 6).

When the radiation source device 18 and the cassette 12 are joined to each other integrally, they are secured together by a joining mechanism 82 (see FIG. 3), to be described later, so that the first radiographic image capturing apparatus 10A can be carried by the operator 38. The radiation source device 18 can be detached from the cassette 12. If the radiation source device 18 includes a locking mechanism for locking a tape measure 72 (see FIGS. 4 and 11) as it is unreeled, then the radiation source device 18 can be detached from the cassette 12 while the tape measure 72 is unlocked from the locking mechanism. With the radiation source device 18 mounted on the cassette 12, a radiographic image of the subject 50 can be captured using another radiation source device 18. In such a case, the first radiographic image capturing apparatus 10A is constituted by the cassette 12, on which the radiation source device 18 is mounted, and the other radiation source device 18. These components are managed by a data center at a time when image capturing conditions are entered and established. The cassette 12 and the radiation source device 18 can thus be managed separately from each other.

The portable first radiographic image capturing apparatus 10A, which has been brought to a site such as an accident site or a disaster site outside of a medical organization, or to a preset disaster site or a preset home receiving home-care services, will be described below with reference to FIGS. 3 through 8.

Figure 3:
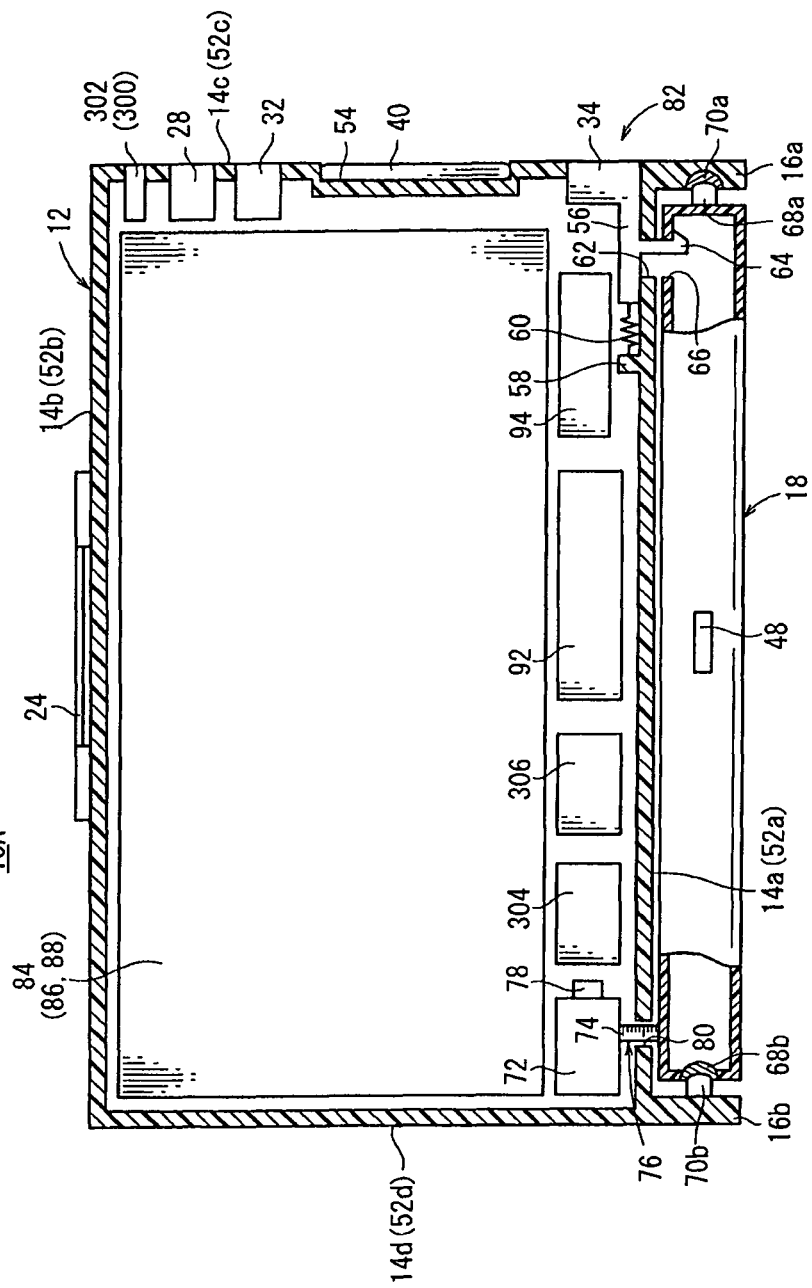
FIG. 3 is a horizontal cross-sectional view taken along line III-III of FIG. 1.

As shown in FIG. 3, the sides 14a, 14b, 14c, 14d of the cassette 12 are constituted by respective side walls 52a, 52b, 52c, 52d. The USB terminal 28, the card slot 32, and the unlocking button 34 are provided on the side wall 52c. The side wall 52c has a recess 54, which is defined between the card slot 32 and the unlocking button 34. The mobile terminal 42 (see FIG. 2) can be placed in the recess 54.

When the unlocking button 34 is pressed by the operator 38 (see FIG. 2), the unlocking button 34 is displaced along the side wall 52a toward the side wall 52d. A slide 56 projects along the side wall 52a from a surface of the unlocking button 34 that faces the side wall 52d, and a spring 60 acts between the slide 56 and a tooth 58 that projects inwardly from the side wall 52a. The spring 60 normally biases the unlocking button 34 to move in a direction from the tooth 58 toward the side wall 52c. The side wall 52a has a through hole 62 defined in a portion thereof against which the slide 56 slides, the through hole 62 extending from an inner surface of the side wall 52a to an outer surface thereof. The slide 56 has a hook 64, which extends through the through hole 62.

Figure 4:
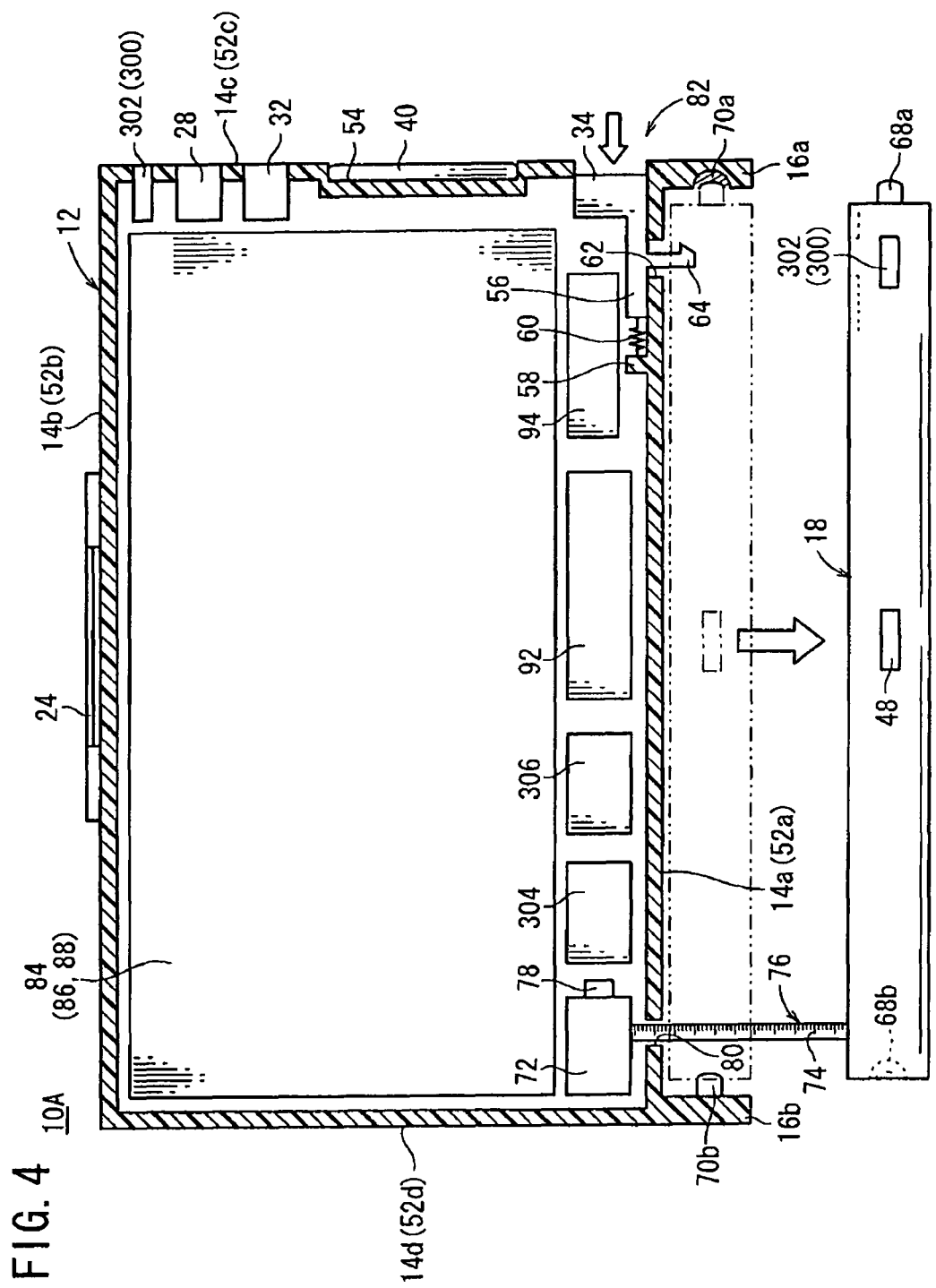
FIG. 4 is a cross-sectional view of the first radiographic image capturing apparatus, showing a radiation source device separated from a cassette.

As shown in FIGS. 3 and 4, the radiation source device 18 has a through hole 66 defined therein at a location aligned with the through hole 62 of the cassette 12 when the radiation source device 18 is held in the cassette 12 by the holders 16a, 16b. The through hole 66 is of substantially the same size as the through hole 62. When the hook 64 is displaced toward the side wall 52c under the bias of the spring 60, the hook 64 engages with an edge of the through hole 66 and locks the radiation source device 18 in place, thereby integrally joining the radiation source device 18 to the cassette 12 (see FIG. 3).

The radiation source device 18 has an electrically conductive connection terminal (first radiation source connection terminal) 68a mounted on an end thereof that faces the holder 16a, and also has an electrically conductive connection terminal (second radiation source connection terminal) 68b mounted on another end thereof that faces the holder 16b. The first radiation source connection terminal 68a is convex in shape toward the holder 16a, whereas the second radiation source connection terminal 68b is concave in shape toward the holder 16b. The radiation source device 18 has a first energy input/output unit 300, or a second energy input/output unit 302 (see FIG. 13) for inputting and outputting electric power through a wired or wireless link, for example. The first radiation source connection terminal 68a and the second radiation source connection terminal 68b, for example, constitute the first energy input/output unit 300 or the second energy input/output unit 302, respectively, and may be electrically connected through a wireless link. The first energy input/output unit 300 or the second energy input/output unit 302 is mounted on a side wall of the radiation source device 18 (see FIG. 1).

The holder 16a of the cassette 12 has an electrically conductive connection terminal (first cassette connection terminal) 70a on a surface thereof that faces the radiation source device 18. The holder 16b of the cassette 12 has an electrically conductive connection terminal (second cassette connection terminal) 70b on a surface thereof that faces the radiation source device 18. The first cassette connection terminal 70a is concave, complementary in shape to the convex first radiation source connection terminal 68a, whereas the second cassette connection terminal 70b is convex, complementary in shape to the concave second radiation source connection terminal 68b. The cassette 12 has a first energy input/output unit 300 or a second energy input/output unit 302 (see FIG. 13) for inputting and outputting electric power through a wired or wireless link, for example. The first cassette connection terminal 70a and the second cassette connection terminal 70b, for example, constitute the first energy input/output unit 300 or the second energy input/output unit 302, and may be electrically connected through a wireless link. The first energy input/output unit 300 or the second energy input/output unit 302 is mounted on the side 14c of the cassette 12.

As shown in FIG. 3, when the hook 64 engages the edge of the through hole 66 under the resiliency of the spring 60 in order to keep the radiation source device 18 and the cassette 12 joined integrally with each other, the convex first radiation source connection terminal 68a and the concave first cassette connection terminal 70a engage with each other, and the concave second radiation source connection terminal 68b and the convex second cassette connection terminal 70b engage with each other, respectively. Therefore, the radiation source device 18 and the cassette 12 are securely and integrally joined with each other. Consequently, the connection terminals 68a, 68b, 70a, 70b function as members for assisting the hook 64 and the through hole 66 in maintaining the radiation source device 18 and the cassette 12 in an integrally joined condition.

As shown in FIG. 4, when the operator 38 presses the unlocking button 34 to move the unlocking button 34 toward the side wall 52d against the resiliency of the spring 60, the hook 64 and the slide 56 are displaced toward the side wall 52d, so as to bring the hook 64 out of engagement with the edge of the through hole 66. While the hook 64 is kept out of engagement with the edge of the through hole 66, i.e., while the operator 38 presses the unlocking button 34, the operator 38 can remove or separate the radiation source device 18 from the cassette 12, whereby the radiation source device 18 and the cassette 12 are released from each other.

The cassette 12 houses therein a tape measure 72 comprising a ribbon 76 marked with graduations 74, which is coiled into a roll by a spring, not shown, in the tape measure 72. The tape measure 72 is combined with a rotary encoder 78 on one side thereof, for detecting the length by which the ribbon 76 is reeled out from the tape measure 72. The ribbon 76, which is reeled out from the tape measure 72, extends through a hole 80 that is defined in the side wall 52a at a location facing the tape measure 72, and a distal end of the ribbon 76 is fixed to the radiation source device 18 near the second connection terminal 68b.

When the radiation source device 18 and the cassette 12 are joined integrally with each other as shown in FIG. 3, most of the ribbon 76 is coiled into a roll inside the tape measure 72 under the resiliency of the spring. On the other hand, when the radiation source device 18 and the cassette 12 are not joined integrally with each other, as shown in FIGS. 4 through 8, the ribbon 76 can be pulled out of the tape measure 72 through the hole 80 by separating the radiation source device 18 away from the cassette 12 against the resiliency of the spring.

The unlocking button 34, the slide 56, the spring 60, the hook 64, the connection terminals 68a, 68b, 70a, 70b, and the tape measure 72 jointly make up a joining mechanism 82 for integrally joining the radiation source device 18 and the cassette 12 with each other when the first radiographic image capturing apparatus 10A is carried, and also for enabling the radiation source device 18 and the cassette 12 to be separated from each other when the first radiographic image capturing apparatus 10A is utilized to capture radiographic images.

The tape measure 72 comprises the ribbon 76, which is marked with graduations 74 in the illustrated embodiment. However, as a functional equivalent to the ribbon 76, the tape measure 72 may comprise a string marked with graduations 74.

Figure 6:
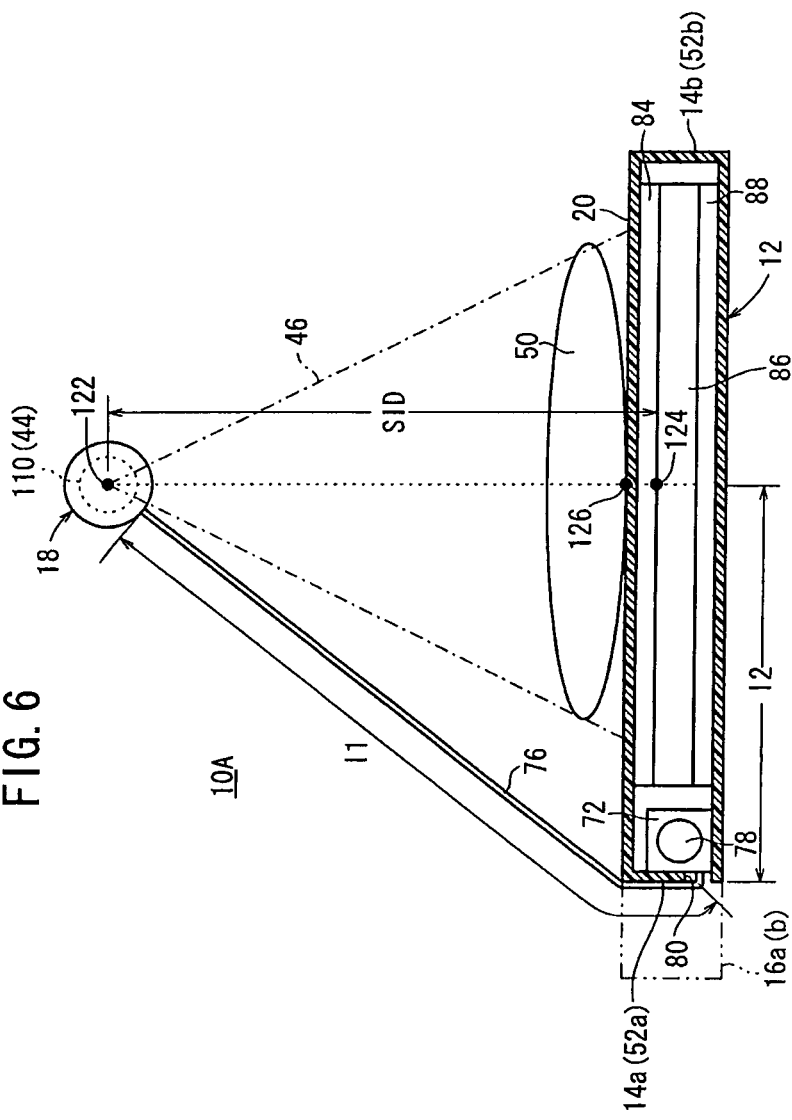
FIG. 6 is an elevational view, partially in cross section, showing the manner in which the first radiographic image capturing apparatus captures a radiographic image.

As shown in FIGS. 3 and 6, the cassette 12 also houses therein a grid 84 for removing scattered rays of radiation 46 from the subject 50 when the radiation source 44 applies radiation 46 with respect to the subject 50, a radiation detector 86 for detecting radiation 46 that has passed through the subject 50, and a lead plate 88 for absorbing back scattered rays of radiation 46, which are successively arranged in this order from the irradiated surface 20 of the cassette 12. The irradiated surface 20 of the cassette 12 may also be constructed as the grid 84.

The radiation detector 86 may comprise a radiation detector (including a front surface reading type and a rear surface reading type) of an indirect conversion type, including a scintillator for converting radiation 46 that has passed through the subject 50 into visible light, and solid-state detectors (hereinafter also referred to as pixels) made of amorphous silicon (a-Si) or the like for converting the visible light into electric signals. A radiation detector of ISS (Irradiation Side Sampling) type as a front surface reading type, comprises solid-state detectors and a scintillator that are successively provided along an irradiation direction of the radiation 46. A radiation detector of PSS (Penetration Side Sampling) type as a rear surface reading type, comprises a scintillator and solid-state detectors that are successively provided along the irradiation direction of the radiation 46. As well as the above-described indirect conversion type, the radiation detector 86 may also comprise a radiation detector of a direct conversion type, comprising solid-state detectors made of amorphous selenium (a-Se) or the like for converting a dose of radiation 46 directly into electric signals.

As shown in FIG. 3, the cassette 12 also houses therein a battery unit 304 as a power supply for the cassette 12, a battery controller (electric power supply limiting unit) 306 for limiting and controlling supply of electric power to the battery unit 304, a cassette controller 92 for controlling the radiation detector 86 (see FIG. 6) with electric power supplied from the battery unit 304, and a transceiver 94 for sending and receiving signals including information concerning radiation 46 that is detected by the radiation detector 86, to and from an external circuit. A plate of lead or the like should preferably be placed over the side surfaces of the cassette controller 92 and the transceiver 94 under the irradiated surface 20 in order to protect the cassette controller 92 and the transceiver 94 against damage, which would otherwise be caused if the cassette controller 92 and the transceiver 94 were irradiated with radiation 46.

Figure 13:
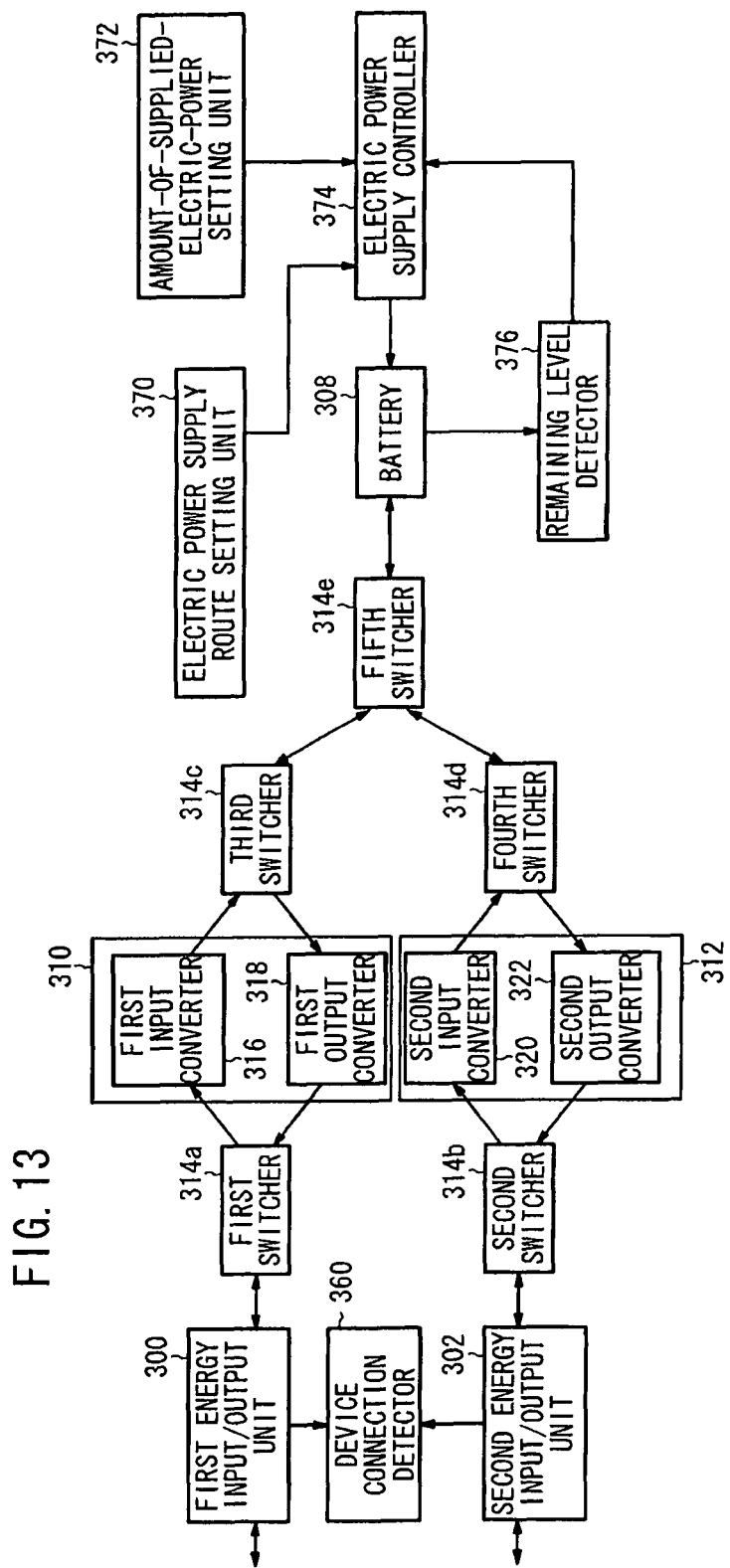
FIG. 13 is a block diagram of a battery unit.

The battery unit 304 supplies electric power to the rotary encoder 78, the radiation detector 86, the cassette controller 92, and the transceiver 94 in the cassette 12. The battery unit 304 can also charge the mobile terminal 42 when the mobile terminal 42 is placed in the recess 54. As shown in FIG. 13, the battery unit 304 includes, in addition to the first energy input/output unit 300 and the second energy input/output unit 302, a battery (electric power storage unit) 308, a first energy converter 310, and a second energy converter 312. The battery unit 304 can be supplied with (i.e., charged by) electric power from an external circuit, or can supply electric power to an external circuit, over a wired or wireless link via the first energy input/output unit 300 and/or the second energy input/output unit 302. A first switcher 314a is connected between the first energy input/output unit 300 and the first energy converter 310. A second switcher 314b is connected between the second energy input/output unit 302 and the second energy converter 312. Third through fifth switchers 314c through 314e are connected between the battery 308 and the first energy input/output unit 300 and the second energy input/output unit 302.

The first energy converter 310 comprises a first input converter 316 and a first output converter 318. The second energy converter 312 comprises a second input converter 320 and a second output converter 322. For inputting electric power via the first energy input/output unit 300, the first switcher 314a electrically connects the first energy input/output unit 300 and the first input converter 316 to each other, while the third switcher 314c and the fifth switcher 314e electrically connect the first input converter 316 and the battery 308 to each other. Conversely, for outputting electric power via the first energy input/output unit 300, the first switcher 314a electrically connects the first energy input/output unit 300 and the first output converter 318 to each other, while the third switcher 314c and the fifth switcher 314e electrically connect the first output converter 318 and the battery 308 to each other. Similarly, for inputting electric power via the second energy input/output unit 302, the second switcher 314b electrically connects the second energy input/output unit 302 and the second input converter 320 to each other, while the fourth switcher 314d and the fifth switcher 314e electrically connect the second input converter 320 and the battery 308 to each other. Conversely, for outputting electric power via the second energy input/output unit 302, the second switcher 314b electrically connects the second energy input/output unit 302 and the second output converter 322 to each other, while the fourth switcher 314d and the fifth switcher 314e electrically connect the second output converter 322 and the battery 308 to each other. The first through fifth switchers 314a through 314e are controlled by an electric power supply controller 374, to be described later, in order to make such connections.

The first energy input/output unit 300, the second energy input/output unit 302, the first energy converter 310, and the second energy converter 312 have different structures depending on the type of energy to be supplied (supplied energy).

For example, if electric energy is supplied through wired connections such as cables, connection terminals, etc., then the first energy input/output unit 300 comprises a connector, which is connected to cables and connection terminals. The first input converter 316 comprises a voltage converter or the like for converting a voltage applied from the first energy input/output unit 300 through the first switcher 314a into a voltage that is optimum for charging the battery 308. The first output converter 318 comprises a voltage converter or the like for converting a voltage output from the battery 308 through the fifth switcher 314e and the third switcher 314c into a voltage that is optimum for power transmission. The second energy input/output unit 302 and the second energy converter 312 also are of a similar construction.

If electric energy is supplied by way of electromagnetic induction through a coil (primary coil or secondary coil) embedded in a contactless power transmission sheet, for example as disclosed in Document 3, then the first energy input/output unit 300 comprises a secondary coil or a primary coil, whereas the first input converter 316 comprises a voltage converter or the like for converting a voltage generated by the first energy input/output unit 300, which functions as a secondary coil, into a voltage that is optimum for charging the battery 308. Further, the first output converter 318 comprises a voltage-to-current converter for converting a voltage output from the battery 308 through the fifth switcher 314e and the third switcher 314c into a current that flows to the first energy input/output unit 300, which functions as a primary coil. The second energy input/output unit 302 and the second energy converter 312 also are of a similar construction.

If electric energy is supplied by way of wireless power transmission technology based on magnetic resonance as disclosed in Document 4, then the first energy input/output unit 300 comprises a second LC resonator or a first LC resonator, which is combined with a first LC resonator or a second LC resonator of an electric power transmitter, whereas the first input converter 316 comprises a coil, i.e., a secondary coil combined with a primary coil as the coil of the second LC resonator, for converting electromagnetic energy generated by the first energy input/output unit 300, which functions as the second LC resonator. Further, the first output converter 318 comprises a coil, i.e., a primary coil combined with a secondary coil as the coil of the first LC resonator, for outputting a voltage output from the battery 308 through the fifth switcher 314e and the third switcher 314c as electromagnetic energy from the first energy input/output unit 300, which functions as the first LC resonator. The second energy input/output unit 302 and the second energy converter 312 also are of a similar construction.

The supplied energy may be optical energy or thermal energy. If the supplied energy is optical energy, then an energy receiver is provided, which comprises a photodetector for detecting optical energy, and an energy converter is provided, which comprises a photoelectric transducer (photoelectric converter) for converting the detected optical energy into electric power. If the supplied energy is thermal energy, then an energy receiver is provided, which comprises a thermal sensor for detecting thermal energy, and an energy converter is provided, which comprises a thermoelectric transducer, i.e., a thermoelectric transducer based on the Seebeck Effect, for converting the detected thermal energy into electric power.

The battery 308 may comprise a secondary battery, such as a nickel hydrogen battery, a nickel cadmium battery, a lithium battery, or the like, or a capacitor, such as a catalytic capacitor, an electric double-layer capacitor, a lithium ion capacitor, or the like. The battery 308 may be detachably mounted on the cassette 12. The battery 308 may comprise a small-size built-in capacitor, which is capable of storing an amount of electric power required to capture at least one radiographic image.

Since the transceiver 94 is capable of sending signals to and receiving signals from an external circuit, the transceiver 94 can send signals to and receive signals from a transceiver 98

(see FIG. 11) of the mobile terminal 42, which is removed from the recess 54, and also can send signals to and receive signals from a transceiver 100 of the radiation source device 18, which is separated from the cassette 12. Even when the cassette 12 and the radiation source device 18 are integrally coupled to each other and/or if the mobile terminal 42 is placed in the recess 54, the transceiver 94 can send signals to and receive signals from the transceivers 98, 100.

Figure 5:
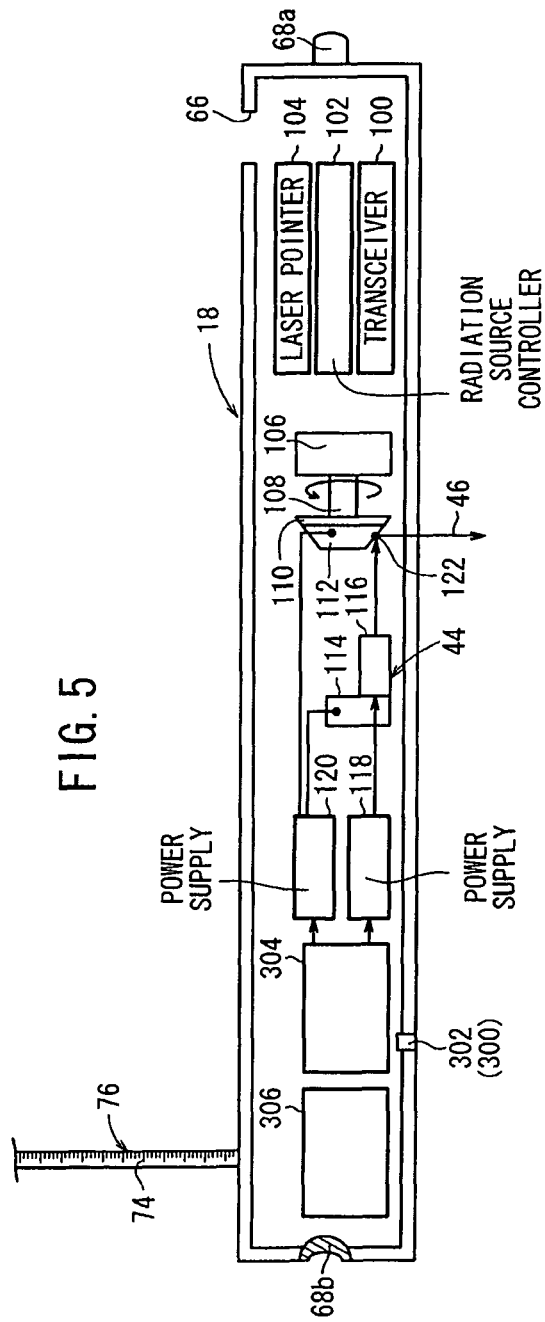
FIG. 5 is a cross-sectional view, shown partially in block form, of internal details of the radiation source device shown in FIG. 1.

As shown in FIG. 5, the radiation source device 18 houses therein the radiation source 44, a battery unit 304, a battery controller 306 for controlling the battery unit 304, a transceiver 100, a radiation source controller 102 for controlling the radiation source 44, and a laser pointer 104. The first energy input/output unit 300 and the second energy input/output unit 302, which are identical to those provided on the cassette 12, are mounted on a side wall of the casing of the radiation source device 18.

The radiation source 44 comprises a field-electron-emission-type radiation source, which is similar to the field-electron-emission-type radiation source disclosed in Japanese Laid-Open Patent Publication No. 2007-103016.

The radiation source 44 includes a disk-shaped rotary anode 110 mounted on a rotational shaft 108, which can be rotated about its axis by a rotating mechanism 106, an annular target layer 112 disposed on the surface of the rotary anode 110 and made up principally from a metallic element such as Mo or the like, a cathode 114 disposed in confronting relation to the rotary anode 110, and a field-electron-emission-type electron source 116 disposed on the cathode 114 in confronting relation to the target layer 112.

When the operator 38 operates the exposure switch 48, the radiation source controller 102 controls the radiation source 44 to output radiation 46. More specifically, when the radiation source 44 is controlled by the radiation source controller 102, the rotating mechanism 106 rotates the rotational shaft 108 so as to rotate the rotary anode 110. The battery unit 304 supplies electric power to a power supply 118, which applies a negative voltage to the field-electron-emission-type electron source 116. The battery unit 304 also supplies electric power to a power supply 120, which applies a voltage between the rotary anode 110 and the cathode 114. More specifically, a positive voltage is applied to the rotary anode 110, whereas a negative voltage is applied to the cathode 114. The field-electron-emission-type electron source 116 emits electrons, which are accelerated and bombard the target layer 112 due to the voltage applied between the rotary anode 110 and the cathode 114. The electrons are focused onto a focus point 122 on the surface of the target layer 112, and the bombarded surface of the target layer 112 emits radiation 46 from the focus point 122 at an intensity level depending on the applied electrons. As the radiation source 44, a portable size and high energy X-ray source that is disclosed in Document 2 and uses a crystal of tourmaline, $LiNbO_3$, $LiTaO_3$, ZnO, and the like, may be employed. In this case, for example, about 100 kV voltage can be generated by using $LiNbO_3$, whose axial length is 1 cm.

For irradiating the subject 50 with radiation 46 in order to capture radiographic images of the subject 50, it is necessary first to perform a preparatory procedure, thus readying the first radiographic image capturing apparatus 10A for capturing radiographic images. The preparatory procedure includes a process for presetting a source-to-image distance (SID), which represents the distance (imaging distance) between the focus point 122 of the radiation source 44 and a position 124 (see FIG. 6) on the radiation detector 86 located directly beneath the focus point 122, and a process for bringing the center of a range within which the irradiated surface 20 is irradiated with radiation 46 into alignment with a central position 126, i.e., a point of intersection, of the aforementioned crisscross guide lines 22.

Figure 7:
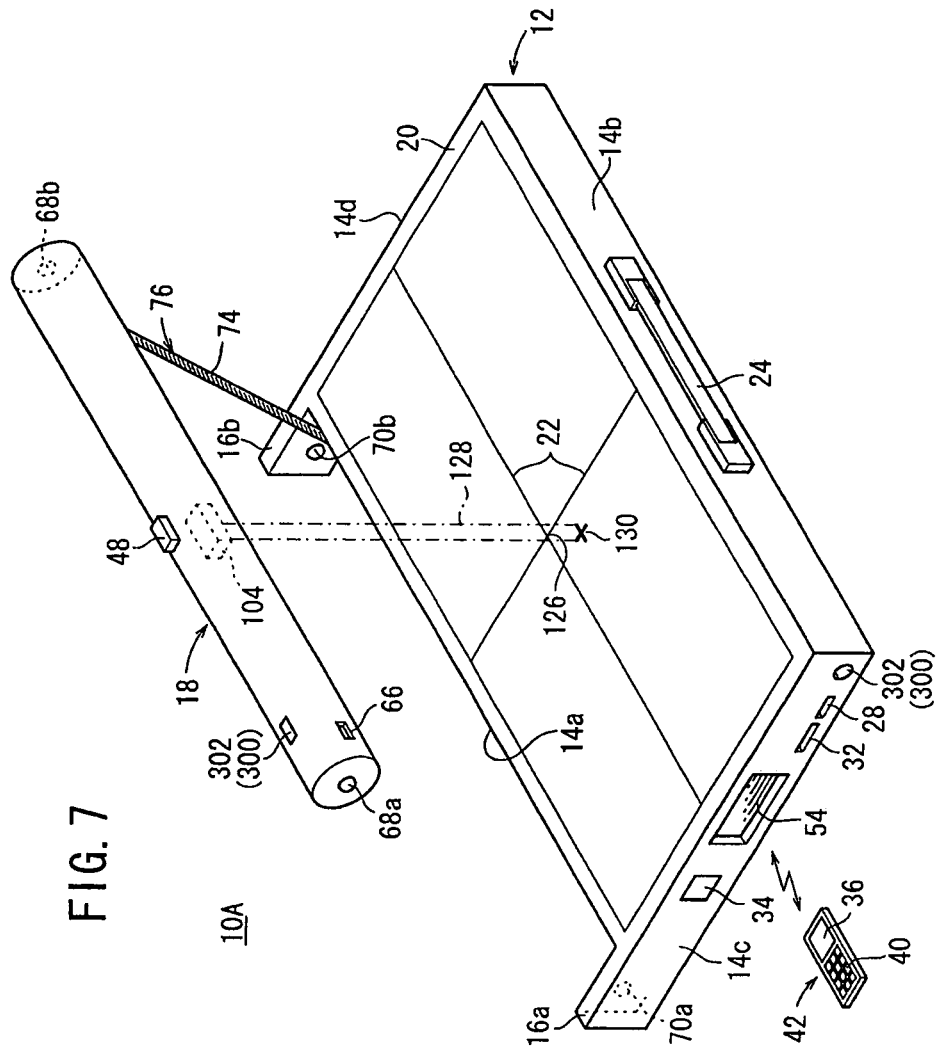
FIG. 7 is an elevational view showing the manner in which the first radiographic image capturing apparatus is readied to capture radiographic images.

The preparatory procedure is carried out as follows. As shown in FIGS. 6 and 7, while the radiation source device 18 is separated from the cassette 12, the operator 38 pulls the ribbon 76 from the tape measure 72 until the length of the ribbon 76, which is reeled out from the tape measure 72, is equal to a reeled-out length l1 that depends on the SID. The laser pointer 104 is controlled by the radiation source controller 102 to apply and focus a laser beam 128 on the irradiated surface 20, in order to display a crisscross mark 130 on the irradiated surface 20, which represents the center of a range within which the irradiated surface 20 is irradiated with radiation 46.

The SID, the reeled-out length l1 that depends on the SID, and a distance l2 between the position 124 or the central position 126 and the side 14a, which has the hole 80 through which the ribbon 76 is pulled out, are related to each other according to the equation $SID \approx (l1^2 - l2^2)^{1/2}$. The distance l2 is constant.

Figure 8:
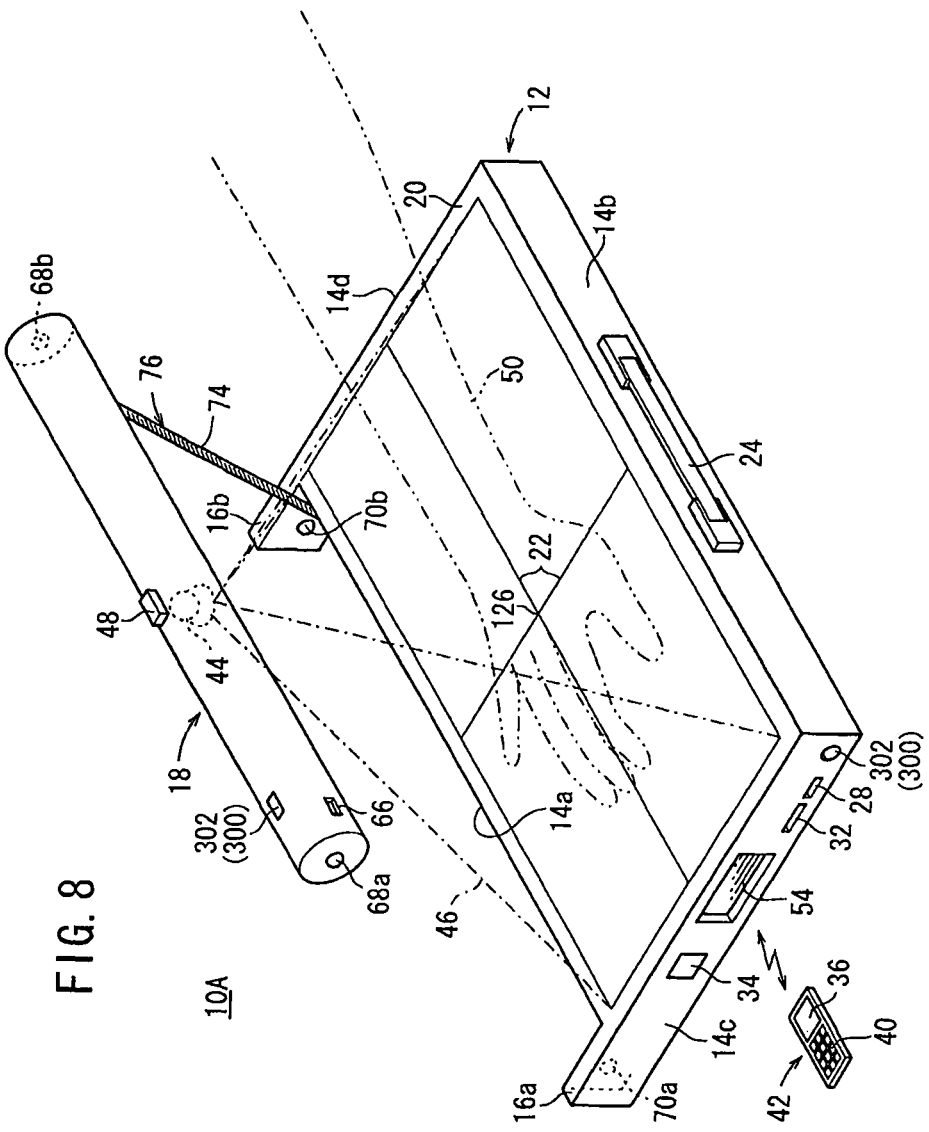
FIG. 8 is an elevational view showing the manner in which the first radiographic image capturing apparatus captures a radiographic image.

After the ribbon 76 has been pulled out from the tape measure 72 by the reeled-out length l1, the operator 38 positionally adjusts the radiation source device 18 so as to bring the mark 130 displayed on the irradiated surface 20 into alignment with the central position 126. Thereafter, the operator 38 turns on the exposure switch 48 to cause the radiation source 44 to apply radiation 46 to the subject 50 on the irradiated surface 20, thereby capturing radiographic images of the subject 50, as shown in FIG. 8. In FIG. 8, an example is shown in which a radiographic image of a hand of the subject 50 is captured.

Figure 9:
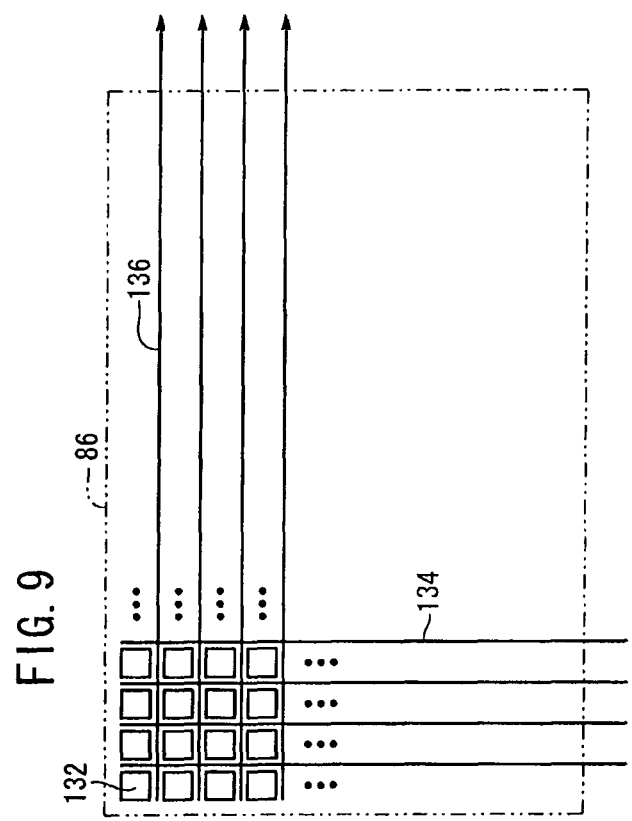
FIG. 9 is a schematic view showing a pixel array of a radiation detector of the first radiographic image capturing apparatus.

As shown in FIG. 9, the radiation detector 86 comprises a number of pixels 132 arrayed on a substrate, not shown, a number of gate lines 134 for supplying control signals to the pixels 132, and a number of signal lines 136 for reading electric signals output from the pixels 132.

A circuit arrangement of the radiation detector 86, which is of an indirect conversion type, for example, that is housed in the cassette 12, will be described in detail below with reference to FIG. 10.

Figure 10:
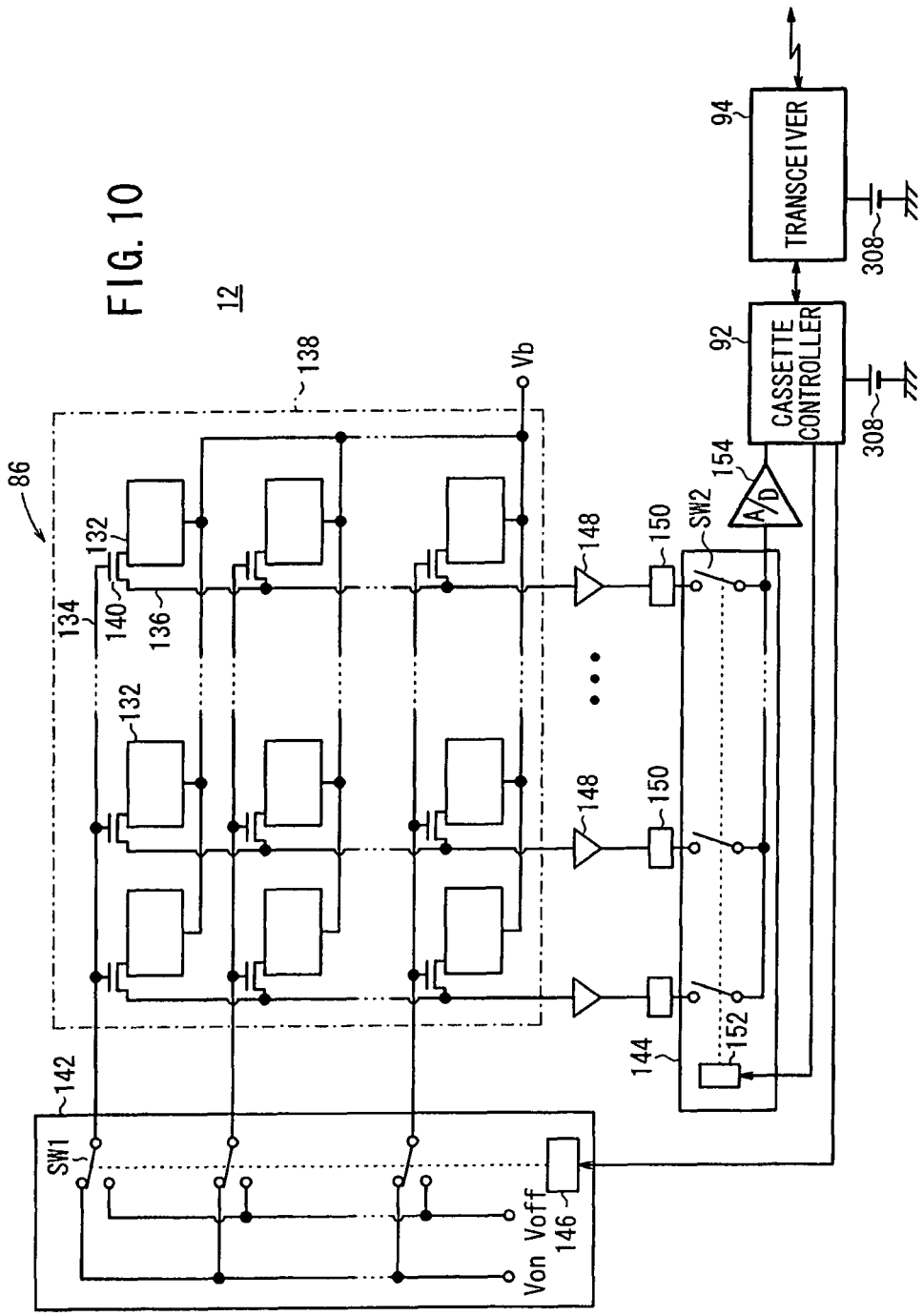
FIG. 10 is a block diagram of a circuit arrangement of the radiation detector disposed in the cassette.

As shown in FIG. 10, the radiation detector 86 comprises an array of thin-film transistors (TFTs) 140 arranged in rows and columns, and a photoelectric conversion layer 138 including the pixels 132, and made of a material such as amorphous silicon (a-Si) or the like for converting visible light into analog electric signals. The photoelectric conversion layer 138 is disposed on the array of TFTs 140. When radiation 46 is applied to the radiation detector 86, the pixels 132 generate electric charges by converting visible light into analog electric signals. Then, when the TFTs 140 are turned on one row at a time, electric charges are read from the pixels 132 as image signals.

The TFTs 140 are connected respectively to the pixels 132. The gate lines 134, which extend parallel to the rows, and the signal lines 136, which extend parallel to the columns, are connected to the TFTs 140. The gate lines 134 are connected to a line scanning driver 142, and the signal lines 136 are connected to a multiplexer 144. The gate lines 134 are supplied with control signals Von, Voff from the line scanning driver 142 for turning on and off the TFTs 140 along the rows. The line scanning driver 142 comprises a plurality of switches SW1 for switching between the gate lines 134, and an address decoder 146 for outputting a selection signal for selecting one of the switches SW1 at a time. The cassette controller 92 supplies an address signal to the address decoder 146.

The signal lines 136 are supplied with electric charges stored by the pixels 132 through the TFTs 140 arranged in the columns. The electric charges supplied to the signal lines 136 are amplified by amplifiers 148, which are connected respectively to the signal lines 136. The amplifiers 148 are connected through respective sample and hold circuits 150 to the multiplexer 144. The multiplexer 144 comprises a plurality of switches SW2 for successively switching between the signal lines 136, and an address decoder 152 for outputting selection signals for selecting one of the switches SW2 at a time. The address decoder 152 is supplied with an address signal from the cassette controller 92. The multiplexer 144 has an output terminal connected to an A/D converter 154. Radiographic image signals, which are generated by the multiplexer 144 based on electric charges from the sample and hold circuits 150, are converted by the A/D converter 154 into digital image signals representing radiographic image information, which is supplied to the cassette controller 92.

The TFTs 140, which function as switching devices, may be combined with another image capturing device, such as a CMOS (Complementary Metal-Oxide Semiconductor) image sensor or the like. Alternatively, the TFTs 140 may be replaced with a CCD (Charge-Coupled Device) image sensor for shifting and transferring electric charges with shift pulses that correspond to gate signals in the TFTs.

Figure 11:
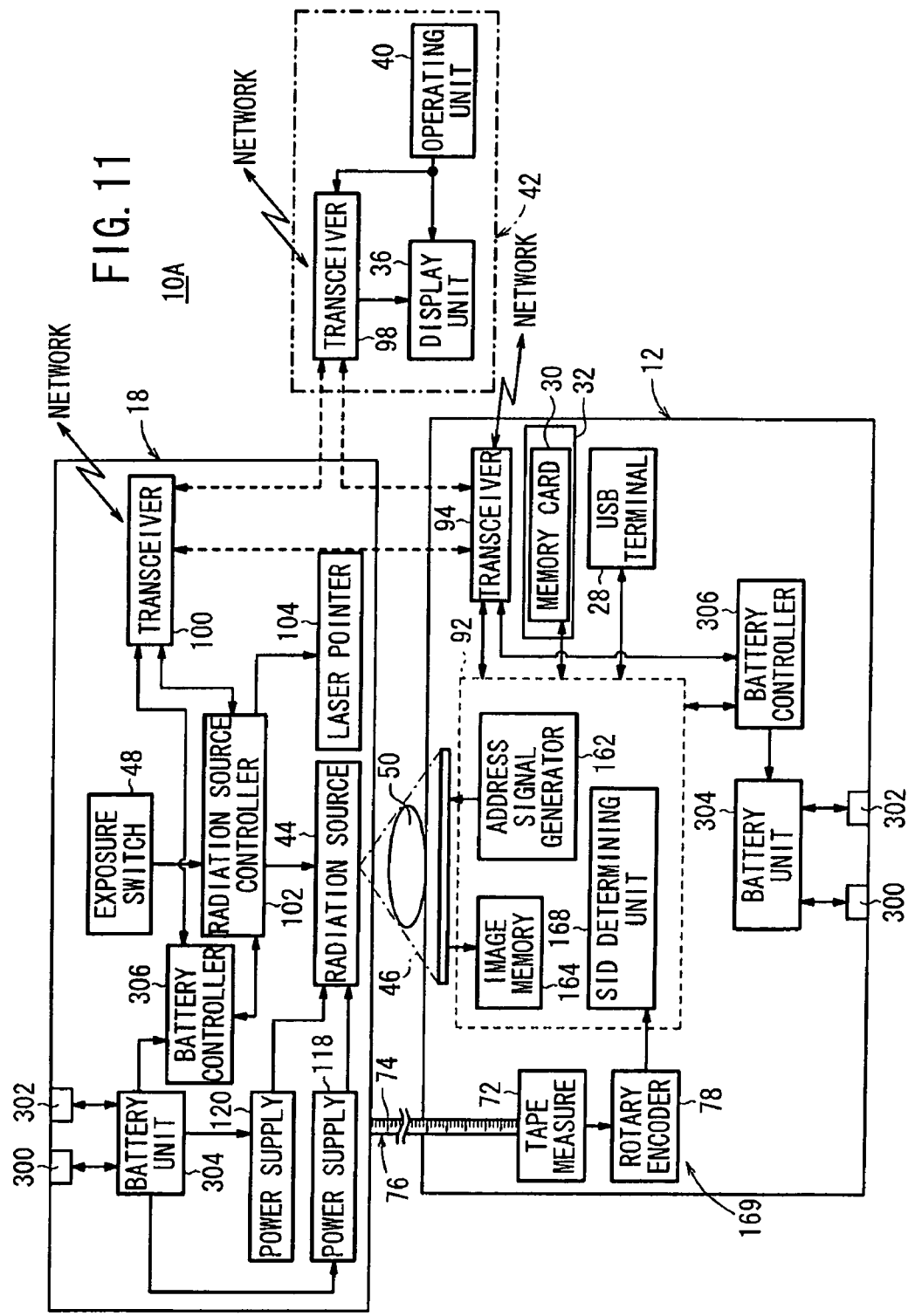
FIG. 11 is a block diagram of the first radiographic image capturing apparatus.

FIG. 11 shows in block form the first radiographic image capturing apparatus 10A. Components of the first radiographic image capturing apparatus 10A, which have not been described above with reference to FIGS. 1 through 10, will mainly be described below with reference to FIG. 11.

The cassette controller 92 comprises an address signal generator 162, an image memory 164, and an SID determining unit (imaging distance determining unit) 168.

The address signal generator 162 supplies address signals to the address decoder 146 of the line scanning driver 142, as well as to the address decoder 152 of the multiplexer 144. The image memory 164 stores the radiographic image information detected by the radiation detector 86.

The SID determining unit 168 calculates the imaging distance between the focus point 122 and the position 124, at a time when the radiation source device 18 is tentatively placed over the irradiated surface 20 according to the present reeled-out length 11 of the ribbon 76, based on the reeled-out length 11 of the ribbon 76, which is input from the rotary encoder 78, and the stored distance 12.

If the calculated imaging distance agrees with the SID, the SID determining unit 168 controls the display unit 36 through the transceivers 94, 98, so as to display information representing the present reeled-out length of the ribbon 76 as the reeled-out length 11 that depends on the SID, and also to display information representing that the imaging distance agrees with the SID. The cassette 12 may include a mechanism for preventing (locking) the ribbon 76 from being reeled out further, when the reeled-out length 11 and the imaging distance have been determined to agree with the SID. If the calculated imaging distance does not agree with the SID, then the SID determining unit 168 controls the display unit 36 through the transceivers 94, 98 in order to display information representing the difference between the present reeled-out length and the reeled-out length 11, and also to display information representing that the imaging distance does not agree with the SID.

The SID determining unit 168, the rotary encoder 78, and the tape measure 72 jointly make up an imaging distance setting means 169.

The cassette controller 92 transmits cassette ID information of the cassette 12 and radiographic image information, which are stored in the image memory 164, via the transceiver 94 to the mobile terminal 42 by way of wireless communications.

A preparatory procedure using the cassette 12 and the radiation source device 18, as well as operations of the first radiographic image capturing apparatus 10A to capture radiographic images, shall be described below.

First, the operator 38 performs an operation to ready the first radiographic image capturing apparatus 10A for capturing radiographic images at a site where the first radiographic image capturing apparatus 10A has been carried. The operator 38 operates the operating unit 40 of the mobile terminal 42 in order to register image capturing conditions including subject information (e.g., SID) of the subject 50 to be imaged.

At this time, the operator 38 operates the operating unit 40 while the mobile terminal 42 either is detached from or placed within the recess 54. If the body region to be imaged and an image capturing method are known, then the operator 38 also operates the operating unit 40 in order to register the body region and the image capturing method as image capturing conditions. If details of the subject 50 are already known before the operator 38 carries the first radiographic image capturing apparatus 10A to the imaging site, then the operator 38 may register the subject information including such details using the mobile terminal 42, which is located at the medical organization, e.g., the hospital, where the subject 50 is being treated.

The registered image capturing conditions, including subject information of the subject 50, are sent from the transceiver 98 of the mobile terminal 42 to the transceiver 94 of the cassette 12 by way of wireless communications, whereupon the image capturing conditions are registered in the cassette controller 92.

When the operator 38 presses the unlocking button 34, the hook 64 is displaced toward the side wall 52d against the resiliency of the spring 60 until the hook 64 is brought out of engagement with the edge of the through hole 66.

When the operator 38 detaches the radiation source device 18 from the cassette 12 while the hook 64 does not engage with the edge of the through hole 66, i.e., while the operator 38 presses the unlocking button 34, then the connection terminal 68a becomes disengaged from the connection terminal 70a, and the connection terminal 68b becomes disengaged from the connection terminal 70b, thereby releasing the radiation source device 18 and the cassette 12 from each other.

The operator 38 sets the imaging distance and then brings the mark 130, which is displayed on the irradiated surface 20, into alignment with the central position 126 of the guide lines 22. Thereafter, the operator 38 places and positions the subject 50 between the irradiated surface 20 and the radiation source device 18.

The operator 38 moves the radiation source device 18, whereby the ribbon 76 is reeled out from the tape measure 72 until the actual reeled-out length of the ribbon 76 reaches the reeled-out length 11 that depends on the SID.

The ribbon 76 is reeled out from the tape measure 72 until the actual reeled-out length of the ribbon 76 reaches the reeled-out length 11, in accordance with either of the two processes described below.

According to the first process, the SID determining unit 168 automatically determines whether or not the actual reeled-out length of the ribbon 76 has reached the reeled-out length 11. Therefore, the operator 38 is able to reel out the ribbon 76 from the tape measure 72 until the actual reeled-out length of the ribbon 76 reaches the reeled-out length 11 that depends on the SID.

In the first process, the rotary encoder 78 detects the actual reeled-out length of the ribbon 76, and based on the detected reeled-out length, the SID determining unit 168 calculates the imaging distance between the focus point 122 and the position 124 when the radiation source device 18 is tentatively placed over the irradiated surface 20 in accordance with the present reeled-out length of the ribbon 76.

If the imaging distance agrees with the SID, then the SID determining unit 168 controls the display unit 36 via the transceivers 94, 98 to display information representing the reeled-out length of the ribbon 76, and also to display information representing that the imaging distance agrees with the SID. If the imaging distance does not agree with the SID, then the SID determining unit 168 controls the display unit 36 via the transceivers 94, 98 to display information representing the difference between the present reeled-out length and the reeled-out length 11, and also to display information representing that the imaging distance does not agree with the SID.

The first process allows the operator 38 to set the imaging distance easily, because the operator 38 may reel out the ribbon 76 from the tape measure 72 according to the information displayed on the display unit 36.

According to the second process, the reeled-out length 11 already is known, and the operator 38 reels out the ribbon 76 from the tape measure 72, while observing the graduations 74, until the present reeled-out length reaches the reeled-out length 11.

After the ribbon 76 has been reeled out from the tape measure 72 until the present reeled-out length reaches the reeled-out length 11 that depends on the SID, the operator 38 moves the radiation source device 18 so as to confront (i.e., be placed in a facing relationship with) the irradiated surface 20.

At this time, the radiation source controller 102 controls the laser pointer 104 to apply a laser beam 128 to the irradiated surface 20. The crisscross mark 130, which represents the center of a range within which the irradiated surface 20 is irradiated with radiation 46, is displayed on the irradiated surface 20. The operator 38 positionally adjusts the radiation source device 18 until the mark 130 and the central position 126 are aligned with each other.

After having adjusted the position of the radiation source device 18 until the mark 130 and the central position 126 are aligned with each other, the operator 38 places or positions the subject 50 on the irradiated surface 20, so that the center of a body region of the subject 50 to be imaged is aligned with the central position 126, i.e., is aligned with the position of the mark 130.

After the above positional adjustment has been made, the radiation source device 18 is secured at the adjusted position by a holder, not shown, for example.

At a site such as a disaster site, due to limited space availability, the first radiographic image capturing apparatus 10A may not be able to capture radiographic images with the desired SID. Therefore, the cassette controller 92 may recalculate image capturing conditions based on a new SID, which is different from the desired SID, and store the recalculated image capturing conditions together with the new SID in association with image data, or transmit the new SID and/or the recalculated image capturing conditions via a network to a data center such as a medical organization for confirmation.

After the subject 50 has been positioned, the operator 38 turns on the exposure switch 48 to begin capturing radiographic images of the subject 50.

When the exposure switch 48 is turned on, the radiation source controller 102 sends a request for image capturing conditions to the cassette controller 92 by way of wireless communications. Based on such a request, the cassette controller 92 sends the image capturing conditions (control signals) with respect to the body region of the subject 50 to be imaged to the radiation source device 18. When the radiation source controller 102 receives the image capturing conditions, the radiation source controller 102 controls the laser pointer 104 in order to stop emitting the laser beam 128, and controls the radiation source 44 to apply radiation 46 at a predetermined dose to the subject 50.

In the radiation source 44, the rotating mechanism 106 is controlled by the radiation source controller 102 in order to rotate the rotational shaft 108 and the rotary anode 110. The power supply 118 applies a negative voltage to the field-electron-emission-type electron source 116, and the power supply 120 applies a voltage between the rotary anode 110 and the cathode 114, based on electric power supplied from the battery unit 304. The field-electron-emission-type electron source 116 emits electrons, which are accelerated by the voltage applied between the rotary anode 110 and the cathode 114, and the electrons bombard the target layer 112. The surface of the target layer 112, which is bombarded with electrons, emits radiation 46 from the focus point 122, the intensity of which depends on the applied electrons.

While the subject 50 is irradiated with radiation 46 for a given irradiation time based on the image capturing conditions, the radiation 46 passes through the subject 50 and reaches the radiation detector 86 of the cassette 12.

Since the radiation detector 86 is of an indirect conversion type, the scintillator of the radiation detector 86 emits visible light having an intensity that depends on the intensity of the radiation 46, and the pixels 132 of the photoelectric conversion layer 138 convert the visible light into electric charges and store the electric charges. The electric charges stored by the pixels 132, which are representative of a radiographic image of the subject 50, are read from the pixels 132 according to address signals, which are supplied from the address signal generator 162 of the cassette controller 92 to the line scanning driver 142 and the multiplexer 144.

More specifically, in response to an address signal supplied from the address signal generator 162, the address decoder 146 of the line scanning driver 142 outputs a selection signal in order to select one of the switches SW1, which supplies the control signal Von to the gates of the TFTs 140 that are connected to the gate line 134 corresponding to the selected switch SW1. In response to address signals supplied from the address signal generator 162, the address decoder 152 of the multiplexer 144 outputs selection signals to successively turn on the switches SW2 so as to switch between the signal lines 136, for thereby reading through the signal lines 136 the electric charges stored in the pixels 132 that are connected to the selected gate line 134.

The electric charges, which are read from the pixels 132 connected to the selected gate line 134, are amplified respectively by the amplifiers 148, sampled by the sample and hold circuits 150, and supplied to the multiplexer 144. Based on the supplied electric charges, the multiplexer 144 generates and supplies radiographic image signals to the A/D converter 154, which converts the radiographic image signals into digital signals. Digital signals representative of the radiographic image information are stored in the image memory 164 of the cassette controller 92.

Similarly, the address decoder 146 of the line scanning driver 142 successively turns on the switches SW1 so as to switch between the gate lines 134 according to the address signals supplied from the address signal generator 162. Electric charges stored in the pixels 132 connected to the successively selected gate lines 134 are read through the signal lines 136, processed by the multiplexer 144, and converted into digital signals by the A/D converter 154. The digital signals are stored in the image memory 164 of the cassette controller 92.

Figure 12:
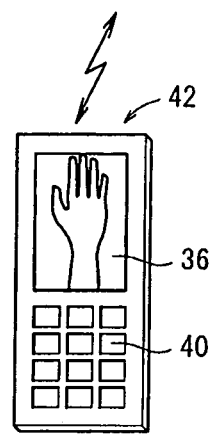
FIG. 12 is a perspective view of a mobile terminal, which displays a radiographic image on a display unit thereof.

Radiographic image information represented by the digital signals stored in the image memory 164 is transmitted through the transceiver 94 to the mobile terminal 42 by way of wireless communications. Radiographic image information transmitted to the mobile terminal 42 is received by the transceiver 98, and is transmitted from the transceiver 98 to the display unit 36, which displays a radiographic image based on the radiation image information, as shown in FIG. 12. The operator 38 can determine whether or not the body region of the subject 50 to be imaged has been appropriately imaged by confirming the radiographic image displayed on the display unit 36.

For example, if the radiographic image displayed on the display unit 36 does not include the body region of the subject 50 to be imaged, then the operator 38 judges that the subject 50 has not been appropriately imaged, and captures another radiographic image of the subject 50. At this time, using the mobile terminal 42, the operator 38 updates the number of captured images in the image capturing conditions, by incrementing the number with the number of recaptured images.

The radiographic image displayed on the display unit 36 may be of a quality that is sufficient enough to determine whether or not the subject 50 has been appropriately imaged. The displayed radiographic image may either be a radiographic image represented by the radiographic image information stored in the image memory 164, an image of low data, or a relatively low resolution processed image.

Figure 14:
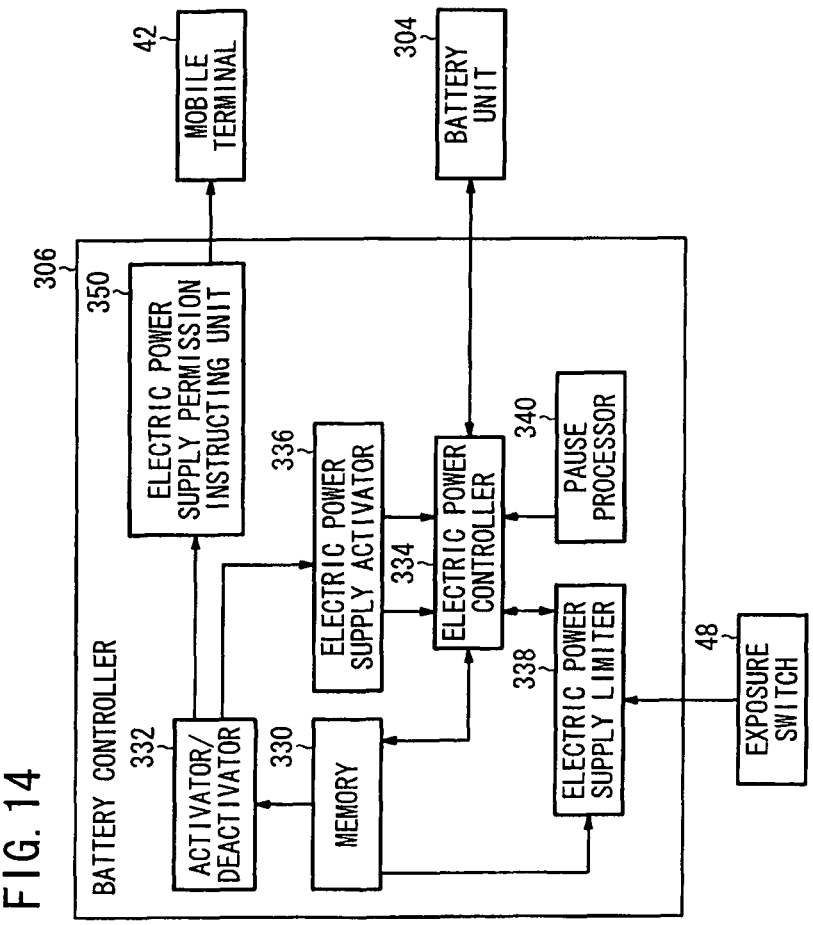
FIG. 14 is a block diagram of a battery controller.

As shown in FIG. 14, the battery controller 306 comprises a memory 330, an activator/deactivator 332, an electric power supply permission instructing unit 350, an electric power supply activator 336, an electric power controller 334, an electric power supply limiter (image capturing process indicating unit) 338, and a pause processor 340.

The activator/deactivator 332 comprises a selected one of a first activator/deactivator 332A, a second activator/deactivator 332B, and a third activator/deactivator 332C, which will be described below.

The first activator/deactivator 332A detects the present position of devices that incorporate the battery controller 306, i.e., the radiation source device 18, the cassette 12, etc., determines whether or not the detected present position is outside of a medical organization, and further determines whether or not supply of electric power between the devices is to be activated. If the present position is outside of the medical organization, then the first activator/deactivator 332A outputs an activation signal. If the present position changes and enters the medical organization after supply of electric power between the devices has been activated, then the first activator/deactivator 332A outputs a full deactivation signal. If the present position changes again and exits the medical organization after the first activator/deactivator 332A has output the full deactivation signal, then the first activator/deactivator 332A outputs an activation signal.

The second activator/deactivator 332B detects the present position of devices that incorporate the battery controller 306, i.e., the radiation source device 18, the cassette 12, etc., determines whether or not the detected present position is a preset position or not, and determines whether supply of electric power between the devices is to be activated. If the present position is the preset position, then the second activator/deactivator 332B outputs an activation signal. If the present position changes and leaves the preset position after supply of electric power between the devices has been activated, then the second activator/deactivator 332B outputs a full deactivation signal. If the present position changes again and reaches the preset position after the second activator/deactivator 332B has output the full deactivation signal, then the second activator/deactivator 332B outputs an activation signal.

The third activator/deactivator 332C determines whether the distance between devices that incorporate the battery controller 306, i.e., the radiation source device 18, the cassette 12, etc., and which belong to the first radiographic image capturing apparatus 10A, satisfies a certain condition or not, and determines whether or not supply of electric power between the devices is to be activated. If the distance satisfies the certain condition, then the third activator/deactivator 332C outputs an activation signal. If the distance changes and does not satisfy the certain condition after supply of electric power between the devices has been activated, then the third activator/deactivator 332C outputs a full deactivation signal. If the distance changes again and satisfies the certain condition after the third activator/deactivator 332C has output the full deactivation signal, then the third activator/deactivator 332C outputs an activation signal.

The electric power supply permission instructing unit 350 outputs a message for prompting entry of image capturing conditions to the mobile terminal 42, for example, based on the activation signal input from the activator/deactivator 332.

The electric power supply activator 336 activates the electric power controller 334 based on the activation signal input from the activator/deactivator 332, and deactivates the electric power controller 334 based on the full deactivation signal input from the activator/deactivator 332.

The electric power controller 334 is activated by the electric power supply activator 336 so as to allow electric power to be supplied between the batteries 308 (see FIG. 13) in the devices, which are connected in a wired fashion, or between the devices that have entered into an area where they can be fed wirelessly, i.e., devices that are connected in a wireless fashion.

If the activator/deactivator 332 has decided to activate supply of electric power between the devices, then since it is possible to supply electric power using the cassette 12 and the radiation source device 18 of the first radiographic image capturing apparatus 10A, it also is possible to supply electric power between either one of these devices and other devices, i.e., devices of another first radiographic image capturing apparatus 10A. For example, it is possible to supply electric power between the radiation source device 18, which is used to capture radiographic images, and the cassette 12 combined therewith, between a radiation source device 18 that is not used to capture radiographic images and the cassette 12 referred to above, and between a cassette 12 that is not used to capture radiographic images and the cassette 12 referred to above.

The electric power supply limiter 338 limits operation of the electric power controller 334 so as to supply electric power only during periods in which radiographic images are being captured.

The pause processor 340 temporarily shuts down the electric power controller 334 at a time when capturing of radiographic images is completed, or when supply of electric power is terminated.

The activator/deactivator 332, the electric power supply permission instructing unit 350, the electric power supply activator 336, the electric power controller 334, etc., which have been referred to above, will be described in detail later.

The memory 330 stores ID information for identifying the devices incorporating the battery controller 306, i.e., the cassette 12, the radiation source device 18, etc., and also stores various conditions. The memory 330 also temporarily stores various table information, which may be entered via a network, the mobile terminal 42, etc.

Details of the first activator/deactivator 332A, the second activator/deactivator 332B, and the third activator/deactivator 332C will be described below with reference to FIGS. 15A through 17C.

Figure 15A:
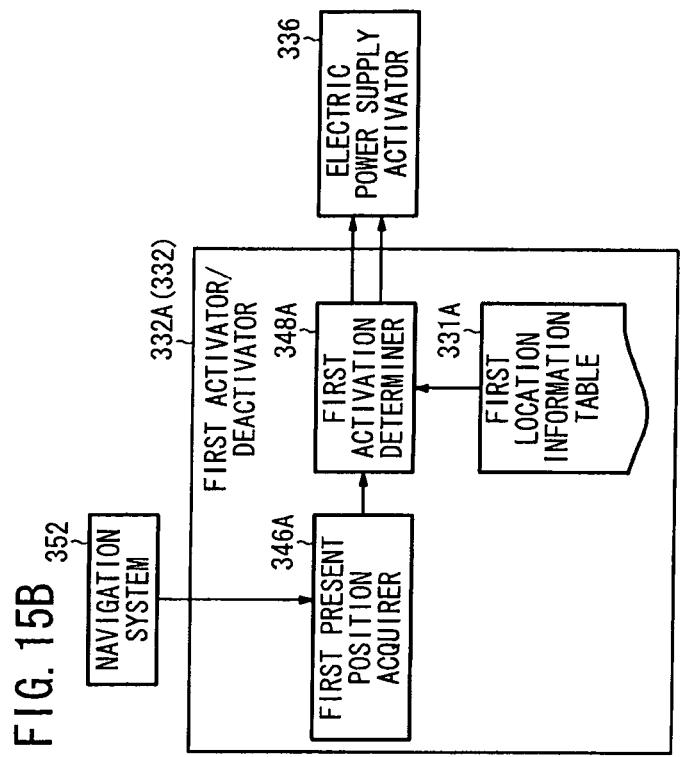
FIG. 15A is a block diagram of a first activator/deactivator according to a first mode.
Figure 15B:
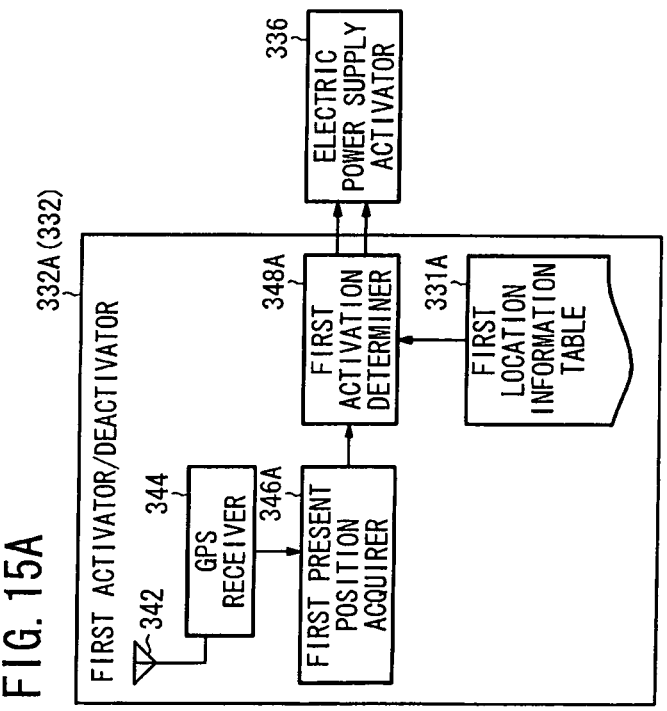
FIG. 15B is a block diagram of a first activator/deactivator according to a second mode.

The first activator/deactivator 332A is available in different configurations according to two modes, i.e., a first mode and a second mode. According to the first mode, as shown in FIG. 15A, the first activator/deactivator 332A detects a present position of the first radiographic image capturing apparatus 10A utilizing GPS (Global Positioning System). The first activator/deactivator 332A according to the first mode comprises a GPS antenna 342, a GPS receiver 344, a first present position acquirer 346A, a first activation determiner 348A, and a first location information table 331A. According to the second mode, as shown in FIG. 15B, it is assumed that the operator 38 uses a car or the like to carry a portable radiographic image capturing apparatus, or carries the first radiographic image capturing apparatus 10A while also carrying a portable navigation system 352 (such as a mobile phone or the like). The first activator/deactivator 332A according to the second mode comprises a first present position acquirer 346A, a first activation determiner 348A, and a first location information table 331A.

The first activator/deactivator 332A according to the first mode, which is shown in FIG. 15A, operates in the following manner. The GPS receiver 344 acquires a GPS signal (comprising positional information of an artificial satellite, and a time at which radio waves are transmitted from the artificial satellite) received by the GPS antenna 342. The first present position acquirer 346A calculates the present position (first present position) of the first radiographic image capturing apparatus 10A based on the acquired GPS signal, and information concerning the time at which radio waves from the artificial satellite are received.

The first activator/deactivator 332A according to the second mode shown in FIG. 15B operates in the following manner. The first present position acquirer 346A acquires positional information from the navigation system 352 as a present position (first present position) of the first radiographic image capturing apparatus 10A.

In each of the first activator/deactivators 332A according to the first and second modes, the first activation determiner 348A compares the first present position, which is acquired by the first present position acquirer 346A, with the positional information of a medical organization that is registered in the first location information table 331A, and determines whether or not the present position is outside of the medical organization. The position of the medical organization in the neighborhood of the first present position may be obtained from a map publishing company database, and is registered in the first location information table 331A, which may be stored in the memory 330. Alternatively, if the first radiographic image capturing apparatus 10A is carried into a predetermined area, then the position of the medical organization in the neighborhood of the predetermined area may be registered in a USB memory, and is read from the USB memory and registered in the first location information table 331A, which may be stored in the memory 330. Positional information of the medical organization refers to information, which represents an area having a radius ranging from 10 to 200 meters from the center of the medical organization, for example. The first activation determiner 348A compares the area with the first present position in order to determine whether or not the first present position lies within the area.

Then, the first activation determiner 348A judges that the present position is outside of the medical organization if the first present position is not within the area, and outputs an activation signal. Alternatively, if the first activation determiner 348A judges that the first present position lies within the area, then the first activation determiner 348A outputs a full deactivation signal.

The second activator/deactivator 332B is available in configurations according to two modes, i.e., a first mode and a second mode. According to the first mode, as shown in FIG. 16A, the second activator/deactivator 332B detects the present position (second present position) of the first radiographic image capturing apparatus 10A utilizing GPS. The second activator/deactivator 332B according to the first mode comprises a GPS antenna 342, a GPS receiver 344, a second present position acquirer 346B, a second activation determiner 348B, and a second location information table 331B. According to the second mode, as shown in FIG. 16B, it is assumed that the operator 38 uses a car or the like to carry a portable radiographic image capturing apparatus, or carries the first radiographic image capturing apparatus 10A while also carrying a portable navigation system 352 (such as a mobile phone or the like). The second activator/deactivator 332B according to the second mode comprises a second present position acquirer 346B for acquiring positional information from the navigation system 352, a second activation determiner 348B, and a second location information table 331B.

In the second activator/deactivator 332B according to each of the first and second modes, the second activation determiner 348B compares the second present position, which is acquired by the second present position acquirer 346B, with area information that is registered in the second location information table 331B, i.e., area information representative of a preset location, and determines whether or not the second present position is in the preset location.

The area information is registered in the second location information table 331B by a location setting unit 353 (see FIGS. 16A and 16B), which is incorporated in the mobile terminal 42, or in a computer at the data center (medical organization).

The area information, which is registered in the second location information table 331B, includes area information by way of absolute positioning as well as area information by way of relative positioning. Area information by way of absolute positioning refers to information representative of an area having a radius ranging from 10 to 200 meters from a position represented by positional information of a fixed location, such as a building, a land location, or the like. Area information by way of relative positioning refers to information representative of an area having a radius ranging from 10 to 200 meters from a position represented by positional information of a moving object (location), in the form of a transport vehicle such as an ambulance, a mobile medical checkup motor vehicle, a railway car, a ship, an aircraft, or the like. Flag information ("0": absolute positioning, "1": relative positioning) applied to the area information may be used to determine whether the registered area information is area information by way of absolute positioning or area information by way of relative positioning.

A process for setting area information by way of absolute positioning will be described below. The location setting unit 353, which is incorporated in a computer at the data center, sets area information by way of absolute positioning by acquiring positional information of a disaster site or an accident site (information of a present position based on GPS) indicated by an external source, and registering information representative of an area having a radius ranging from 10 to 200 meters from the position represented by the acquired positional information, as area information representative of the disaster site or the accident site, in the second location information table 331B in a database of the data center. Usually, a public organization, such as an administrative institution, a fire department, a police department, or the like, serves as the external source that indicates the disaster site or the accident site. However, an operator 38 who works for a medical organization may witness a disaster site or an accident site, and may send the present position to the data center using a present position sending function of a mobile phone possessed by the operator 38.

A medical organization site, a medical checkup site, or a home-care service site is set by acquiring positional information, which represents the address of a medical organization that does not have a radiation facility, such as a clinic or the like, a place where a medical checkup is to be carried out, or a home receiving home-care services, from the database of a map publishing company, and registering information representative of an area having a radius ranging from 10 to 200 meters from the position represented by the acquired positional information, and flag information representative of the absolute position thereof, as area information representative of the medical organization site, the medical checkup site, or the home-care service site, in the second location information table 331B.

A computer at the data center also sets area information by way of absolute positioning when the operator 38 who carries the first radiographic image capturing apparatus 10A sends information of the present position of the operator 38 to the data center using the mobile terminal 42, at a time when the operator 38 arrives at the medical organization, the accident site, the disaster site, the medical checkup site, or the home-care service site. The computer at the data center acquires information of the present position sent from the mobile terminal 42 by the operator 38, and registers information representative of an area having a radius ranging from 10 to 200 meters from the position represented by the acquired positional information, and flag information representative of the absolute position thereof, as area information representative of a preset location, in the second location information table 331B.

After having registered the second location information table 331B in the database, the location setting unit 353, which is incorporated in the computer at the data center, sends the second location information table 331B to the mobile terminal 42 of the first radiographic image capturing apparatus 10A. Upon receiving the second location information table 331B, the mobile terminal 42 sends the second location information table 331B to the battery controller 306. The battery controller 306 then stores the received second location information table 331B in the memory 330.

The location setting unit 353, which is incorporated in the mobile terminal 42, sets area information by way of absolute positioning when the operator 38 enters an operation input into the mobile terminal 42 in order to activate the location setting unit 353, and the location setting unit 353 designates the present position of the operator 38 as a preset location. The location setting unit 353 registers information representative of an area having a radius ranging from 10 to 200 meters from the designated present position, and flag information representative of the absolute position thereof, as area information representative of the preset location, in the second location information table 331B. Thereafter, the location setting unit 353 sends the second location information table 331B to the data center for sharing the second location information table 331B. The data center sends the received second location information table 331B to other mobile terminals 42, so that the second location information table 331B can be shared among the mobile terminals 42.

A process of setting area information by way of relative positioning will be described below. When the operator 38 who carries the first radiographic image capturing apparatus 10A is on board a transport vehicle, such as an ambulance, a mobile medical checkup motor vehicle, a railway car, a ship, an aircraft, or the like, the operator 38 sends information concerning the present position of the operator 38 together with a code representative of the relative position to the data center. The location setting unit 353 at the data center acquires the information of the present position of the operator 38, which was sent by the operator 38 from the mobile terminal 42, acquires the present position of the transport vehicle from a transport vehicle management center corresponding to the present position based on the code representative of the relative position, and registers information representative of an area having a radius ranging from 10 to 200 meters from the present position, and flag information representative of the relative position thereof, as area information representative of the preset location, in the second location information table 331B. Thereafter, the location setting unit 353 acquires the present position of the transport vehicle periodically, for example, at time intervals from 1 to 10 minutes, from the transport vehicle management center, and repeatedly updates and registers information representative of an area having a radius ranging from 10 to 200 meters from the present position, as area information representative of the preset location, in the second location information table 331B. Each time that the location setting unit 353 periodically updates and registers the area information representative of the preset location in the second location information table 331B, the location setting unit 353 sends the second location information table 331B to the mobile terminal 42 of the first radiographic image capturing apparatus 10A. After the mobile terminal 42 has received the second location information table 331B, the mobile terminal 42 sends the second location information table 331B to the battery controller 306. The battery controller 306 then stores the received second location information table 331B in the memory 330. The location setting unit 353 may send only area information representative of the relative position to the mobile terminal 42 of the first radiographic image capturing apparatus 10A.

The location setting unit 353, which is incorporated in the mobile terminal 42, sets area information by way of relative positioning when the operator 38, who is on board the transport vehicle, enters an operation input into the mobile terminal 42 in order to activate the location setting unit 353, designates the present position of the operator as a preset location, and further designates the position as a relative position. Based on the code representative of the relative position, the location setting unit 353 acquires the present position of the transport vehicle from the transport vehicle management center corresponding to the information representative of the present position, and registers information representative of an area having a radius ranging from 10 to 200 meters from the position and flag information representative of the relative position thereof, as area information representative of the relative position, in the second location information table 331B, which may be stored in the memory 330. Thereafter, the location setting unit 353 acquires the present position of the transport vehicle periodically, for example, at time intervals from 1 to 10 minutes, from the transport vehicle management center, and repeatedly updates and registers information representative of an area having a radius ranging from 10 to 200 meters from the present position, as area information representative of the preset location, in the second location information table 331B. Each time that the location setting unit 353 periodically updates and registers the area information representative of the preset location in the second location information table 331B, the location setting unit 353 sends the second location information table 331B to the data center for enabling sharing of the second location information table 331B. The data center sends the received second location information table 331B to other mobile terminals 42 for enabling the second location information table 331B to be shared among the mobile terminals 42. A transport vehicle, such as an ambulance or a mobile medical checkup motor vehicle, may be parked for a relatively long time of 30 minutes or longer for diagnosing a patient. In such a case, area information by way of absolute positioning may be registered in the second location information table 331B.

The second activation determiner 348B compares the second present position with the area information registered in the second location information table 331B in order to determine whether or not the second present position is in an area represented by the area information. If the second present position is within an area represented by the area information, then the second activation determiner 348B judges that the second present position is in the preset location, and outputs an activation signal. When the second activation determiner 348B compares the second present position with area information by way of absolute positioning, the second activation determiner 348B compares the second present position, which varies from time to time, with fixed area information, i.e., the area information by way of absolute positioning. When the second present position enters the area represented by the area information, the second activation determiner 348B outputs an activation signal. When the second activation determiner 348B compares the second present position with area information by way of relative positioning, the second activation determiner 348B compares the second present position, which varies from time to time, with area information, which also varies from time to time, i.e., the area information by way of relative positioning. When the second present position enters the area represented by the area information, the second activation determiner 348B outputs an activation signal. After having output the activation signal, if the second activation determiner 348B judges that the second present position has left the area represented by the area information registered in the second location information table 331B, then the second activation determiner 348B judges that the devices are not within the preset location, and outputs a full deactivation signal.

The third activator/deactivator 332C is available in configurations according to three modes, i.e., a first mode, a second mode, and a third mode, for example, depending on certain respective conditions.

According to the first mode, the certain condition is that the linear distance between the devices of the first radiographic image capturing apparatus 10A is equal to or less than a preset reference distance.

Figure 17A:
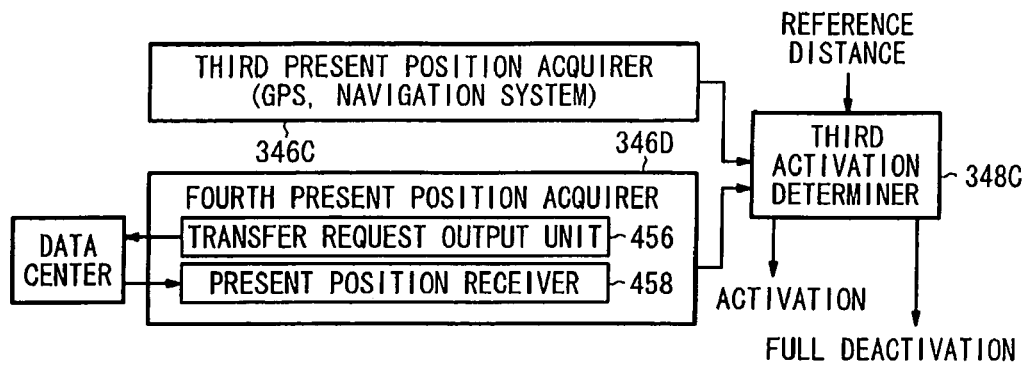
FIG. 17A is a block diagram of a third activator/deactivator according to a first mode.

As shown in FIG. 17A, the third activator/deactivator 332C according to the first mode comprises a third present position acquirer 346C, a fourth present position acquirer 346D, and a third activation determiner 348C.

The third present position acquirer 346C acquires the present position (third present position) of a device, which incorporates therein the battery controller 306, i.e., the radiation source device 18, the cassette 12, or the like. The fourth present position acquirer 346D acquires the present position (fourth present position) of a device, which is to be associated with the above device (hereinafter also referred to as the "aforesaid device"). If the linear distance between the third present position and the fourth present position is equal to or smaller than the preset reference distance, then the third activator/deactivator 332C according to the first mode outputs an activation signal. If the linear distance between the third present position and the fourth present position is greater than the preset reference distance, then the third activator/deactivator 332C according to the first mode outputs a full deactivation signal.

If the aforesaid device, the present position (third present position) of which is acquired by the third present position acquirer 346C, is the radiation source device 18, then the device to be associated with the above device refers to the cassette 12. The cassette 12, together with the radiation source device 18, makes up the first radiographic image capturing apparatus 10A.

The third present position acquirer 346C is available in configurations according to two modes, i.e., a first mode and a second mode. According to the first mode, the third present position acquirer 346C detects the third present position using GPS, and comprises at least a GPS antenna and a GPS receiver. According to the second mode, it is assumed that the operator 38 uses a car or the like to carry the radiation source device 18 and the cassette 12, or carries the radiation source device 18 and the cassette 12 while also carrying a portable navigation system (mobile phone or the like). The third present position acquirer 346C acquires positional information from the navigation system as the third present position.

The fourth present position acquirer 346D comprises a transfer request output unit 456 and a present position receiver 458. The transfer request output unit 456 outputs a transfer request signal through the network to the data center. The transfer request signal includes an ID of a device the present position (third present position) of which is acquired by the third present position acquirer 346C, a code representative of a transfer request for information of the present position of a device to be associated with the aforesaid device, and information representative of the third present position of the aforesaid device. After the data center has received the transfer request signal from the device, the data center searches a device association table, not shown, for the ID of a device that corresponds to the ID included in the transfer request signal, extracts the present position of the retrieved ID from the transfer request signal sent from the device indicated by the retrieved ID, and transfers the retrieved ID and the present position (fourth present position) of the device indicated by the ID via the network to the source of the transfer request signal. The present position receiver 458 of the fourth present position acquirer 346D receives the ID of the device along with the present position (fourth present position) thereof, which are transferred from the data center.

The third activation determiner 348C according to the first mode calculates a difference (linear distance) between the third present position (the present position of the device) from the third present position acquirer 346C and the fourth present position (the present position of the device to be associated with the aforesaid device) from the fourth present position acquirer 346D, and determines whether or not the calculated linear distance is equal to or smaller than a reference distance registered in the memory 330. If the linear distance is equal to or smaller than the reference distance, then the third activation determiner 348C outputs an activation signal. If the linear distance is greater than the reference distance, then the third activation determiner 348C outputs a full deactivation signal.

In other words, the third activator/deactivator 332C according to the first mode outputs an activation signal when the linear distance between the radiation source device 18 and the cassette 12 of the first radiographic image capturing apparatus 10A is equal to or smaller than the reference distance. For example, when the radiation source device 18 enters a circular area the radius of which is defined by the reference distance from the cassette 12 at the center of the circular area, the third activator/deactivator 332C outputs an activation signal. Conversely, when the linear distance between the radiation source device 18 and the cassette 12 of the first radiographic image capturing apparatus 10A is greater than the reference distance, e.g., when the radiation source device 18 leaves the circular area the radius of which is defined by the reference distance from the cassette 12 at the center of the circular area, the third activator/deactivator 332C outputs a full deactivation signal. The third activator/deactivator 332C will operate similarly if the radiation source device 18 is at the center of the circular area and the cassette 12 enters or leaves the circular area.

According to the second mode, the certain condition is that the linear distance between the devices of the first radiographic image capturing apparatus 10A lies within a communication range of each of the devices.

Figure 17B:
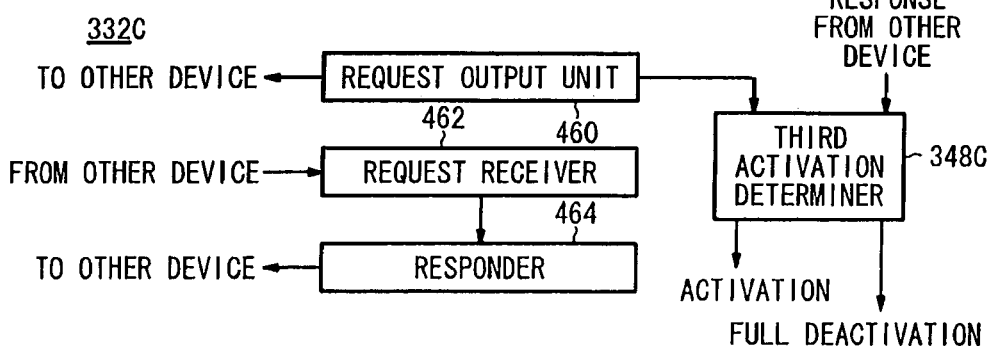
FIG. 17B is a block diagram of a third activator/deactivator according to a second mode.

As shown in FIG. 17B, the third activator/deactivator 332C according to the second mode comprises a request output unit 460, a request receiver 462, a responder 464, and a third activation determiner 348C.

The request output unit 460 periodically outputs a request signal including the ID of the aforesaid device through a transceiver in a wireless fashion.

The request receiver 462 receives a request signal output from another device through the transceiver.

The responder 464 determines whether or not the ID included in the received request signal is equivalent to the ID of a device to be associated with the aforesaid device, i.e., the ID of a device which, together with the aforesaid device, makes up the first radiographic image capturing apparatus 10A. If the ID included in the received request signal is equivalent to the ID of a device to be associated with the aforesaid device, then the responder 464 outputs an answer signal to the other device. Since the other device also has a similar responder 464, the other device outputs an answer signal in response to a request signal output from the aforesaid device.

The third activation determiner 348C according to the second mode determines whether or not an answer signal has arrived from another device within a preset response time from when the aforesaid device output a request signal. If an answer signal has arrived within the preset response time, then the third activation determiner 348C outputs an activation signal. If an answer signal has not arrived within the preset response time, then the third activation determiner 348C outputs a full deactivation signal.

Inasmuch as the transceiver 100 of the radiation source device 18 and the transceiver 94 of the cassette 12 associated with the radiation source device 18 are energized by the batteries 308 (see FIG. 13), the transceivers 100, 94 have a small communication range, i.e., from 2 to 5 meters, for example, for reducing electric power consumption. When the radiation source device 18 of the first radiographic image capturing apparatus 10A enters the communication range of the cassette 12, for example, the third activation determiner 348C outputs an activation signal. Conversely, when the radiation source device 18 leaves the communication range of the cassette 12, the third activation determiner 348C outputs a full deactivation signal. The third activation determiner 348C operates similarly if the cassette 12 enters or leaves the communication range of the radiation source device 18.

According to the third mode, the certain condition is that the linear distance between the devices of the first radiographic image capturing apparatus 10A lies within a range in which the devices can be connected in a wired or wireless fashion.

Figure 17C:
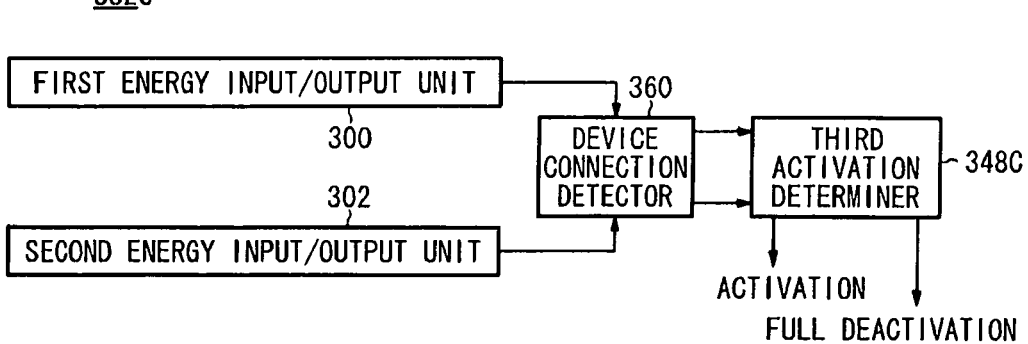
FIG. 17C is a block diagram of a third activator/deactivator according to a third mode.

As shown in FIG. 17C, the third activator/deactivator 332C according to the third mode comprises a device connection detector 360 and a third activation determiner 348C.

As shown in FIG. 13, the device connection detector 360 detects whether the device, i.e., the radiation source device 18 or the cassette 12, is connected to at least one of the first energy input/output unit 300 and the second energy input/output unit 302 in a wired or wireless fashion. A wireless connection is detected by an obstacle sensor such as an ultrasonic sensor or the like, which determines whether the device, i.e., the radiation source device 18 or the cassette 12, has entered into an area in which the device can be fed wirelessly from the first energy input/output unit 300 or the second energy input/output unit 302. When connection of the device to at least one of the first energy input/output unit 300 and the second energy input/output unit 302 is detected, the device connection detector 360 outputs a detection signal, which indicates connection of the device to the third activation determiner 348C. When connection of the device to either one of the first energy input/output unit 300 and the second energy input/output unit 302 is not detected after the detection signal has been output, the device connection detector 360 outputs a non-detection signal to the third activation determiner 348C.

The third activation determiner 348C according to the third mode outputs an activation signal based on the detection signal input from the device connection detector 360, and outputs a full deactivation signal based on the non-detection signal input from the device connection detector 360. Wired connection of another device to the aforesaid device indicates that the linear distance between the devices makes it possible to connect them in a wired fashion, whereas wireless connection of another device to the aforesaid device indicates that the linear distance between the devices makes it possible to feed signals to them in a wireless fashion.

When it is necessary to refer to the first activation determiner 348A, the second activation determiner 348B, and the third activation determiner 348C collectively, they hereinafter will be referred to as an "activation determiner 348."

If supply timing conditions stored in the memory 330 are free of timing controls, then the electric power supply permission instructing unit 350 outputs a message indicating permission to supply electric power to the mobile terminal 42 and/or energizes (or de-energizes) a pilot lamp (not shown) based on an activation signal input from the activator/deactivator 332. If the supply timing conditions indicate supply of electric power before or after capturing of radiographic images, then the electric power supply permission instructing unit 350 outputs a message prompting entry of the image capturing conditions to the mobile terminal 42, based on the activation signal input from the activator/deactivator 332.

Based on the activation signal, the electric power supply activator 336 is activated. If the supply timing conditions stored in the memory 330 are free of timing controls, then the electric power supply activator 336 of a device whose electric power supply switch has been operated activates the corresponding electric power controller 334 based on operation of the electric power supply switch. The electric power supply activator 336 may activate the electric power controller 334 without waiting for the electric power supply switch to be operated. In such a case, if an interlock process is not performed, then the electric power controllers 334 of all the devices outside of the medical organization, all devices in the preset location, or all devices of which the linear distance therebetween satisfies the certain condition referred to above, are activated, thus tending to cause processing operations to interfere with each other. Therefore, the electric power supply activator 336 of each of the devices refers to interlock information registered in the memory 330, i.e., the ID of the radiation source device 18 or the cassette 12 to be used in a preset image capturing process, and only the electric power supply activator 336 of a device whose ID is identical to the ID of the interlock information activates the corresponding electric power controller 334. Thus, for example, only the electric power controller 334 of the radiation source device 18 that is used in the preset image capturing process is operated, while interference from the other devices is prevented.

If the supply timing conditions indicate supply of electric power before capturing of radiographic images, then the electric power controller 334 is activated based on the image capturing conditions (order) that are input from the mobile terminal 42. In this case, only the electric power supply activator 336 of a device having an ID identical to that of the ID of the radiation source device 18 or the cassette 12 to be used to capture radiographic images, which is registered in advance in the image capturing conditions, activates the corresponding electric power controller 334. If the supply timing conditions indicate supply of electric power after capturing of radiographic images, then the electric power controller 334 is activated based on an image capture completion signal supplied from an image capture completion determiner 386 (see FIG. 18). In this case as well, only the electric power supply activator 336 of a device having an ID identical to that of the ID of the radiation source device 18 or the cassette 12 to be used to capture radiographic images, which is registered in advance in the image capturing conditions, activates the corresponding electric power controller 334. The electric power supply activator 336 is shut down based on a full deactivation signal input from the activator/deactivator 332, whereupon the electric power supply activator 336 waits to be activated at a subsequent time by the activation determiner 348.

Figure 18:
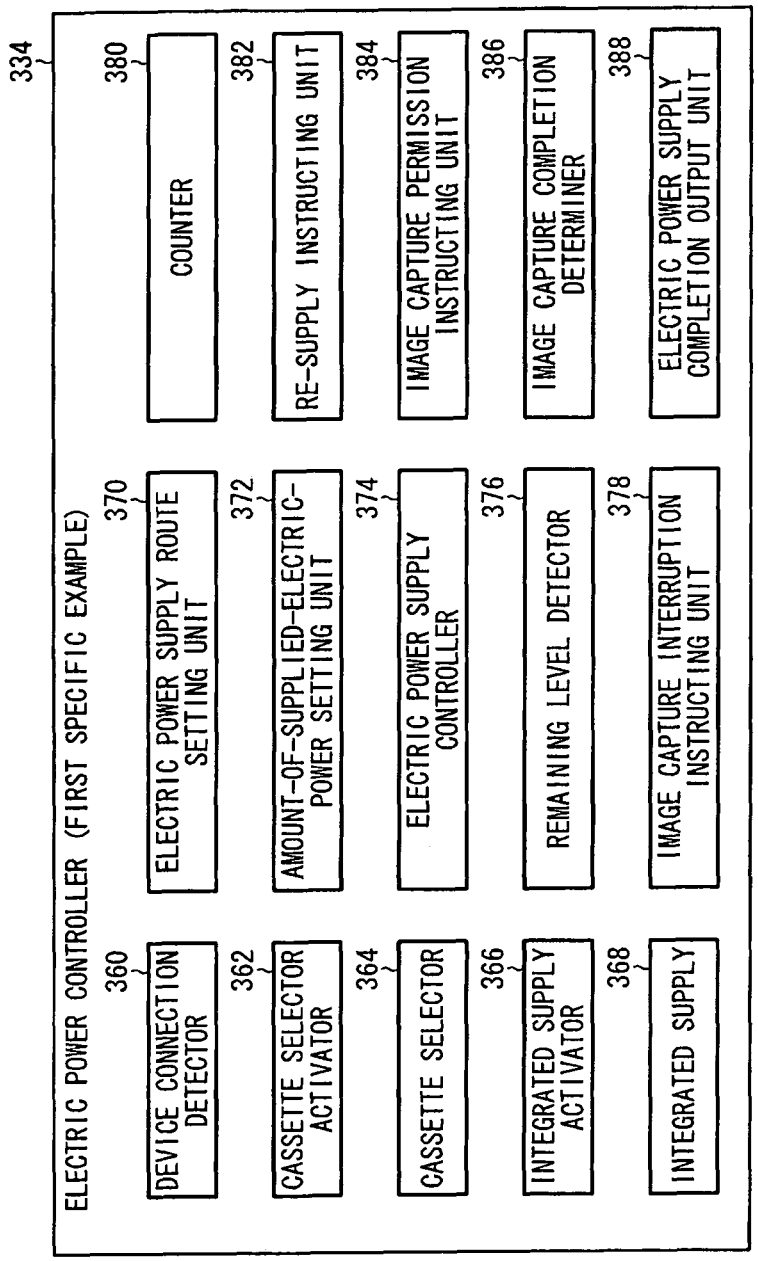
FIG. 18 is a block diagram of a power controller according to a first specific example.

The electric power controller 334 is available in different configurations according to two specific examples, i.e., a first specific example and a second specific example. According to the first specific example, the battery 308 of the radiation source device 18 supplies electric power to the battery 308 of the cassette 12, or the battery 308 of the radiation source device 18 controls supply of electric power to the battery 308 of the cassette 12. As shown in FIG. 18, the electric power controller 334 according to the first specific example comprises, as functional components thereof, a device connection detector 360, a cassette selector activator 362, a cassette selector 364, an integrated supply activator 366, an integrated supply 368, an electric power supply route setting unit 370, an amount-of-supplied-electric-power setting unit 372, an electric power supply controller 374, a remaining level detector 376, an image capture interruption instructing unit 378, a counter 380, a re-supply instructing unit 382, an image capture permission instructing unit 384, an image capture completion determiner 386, and an electric power supply completion output unit 388. If the activator/deactivator 332 comprises the third activator/deactivator 332C (see FIG. 17C) according to the third mode, then since the device connection detector 360 is incorporated in the third activator/deactivator 332C, the device connection detector 360 is not included within the electric power controller 334.

Figure 19:
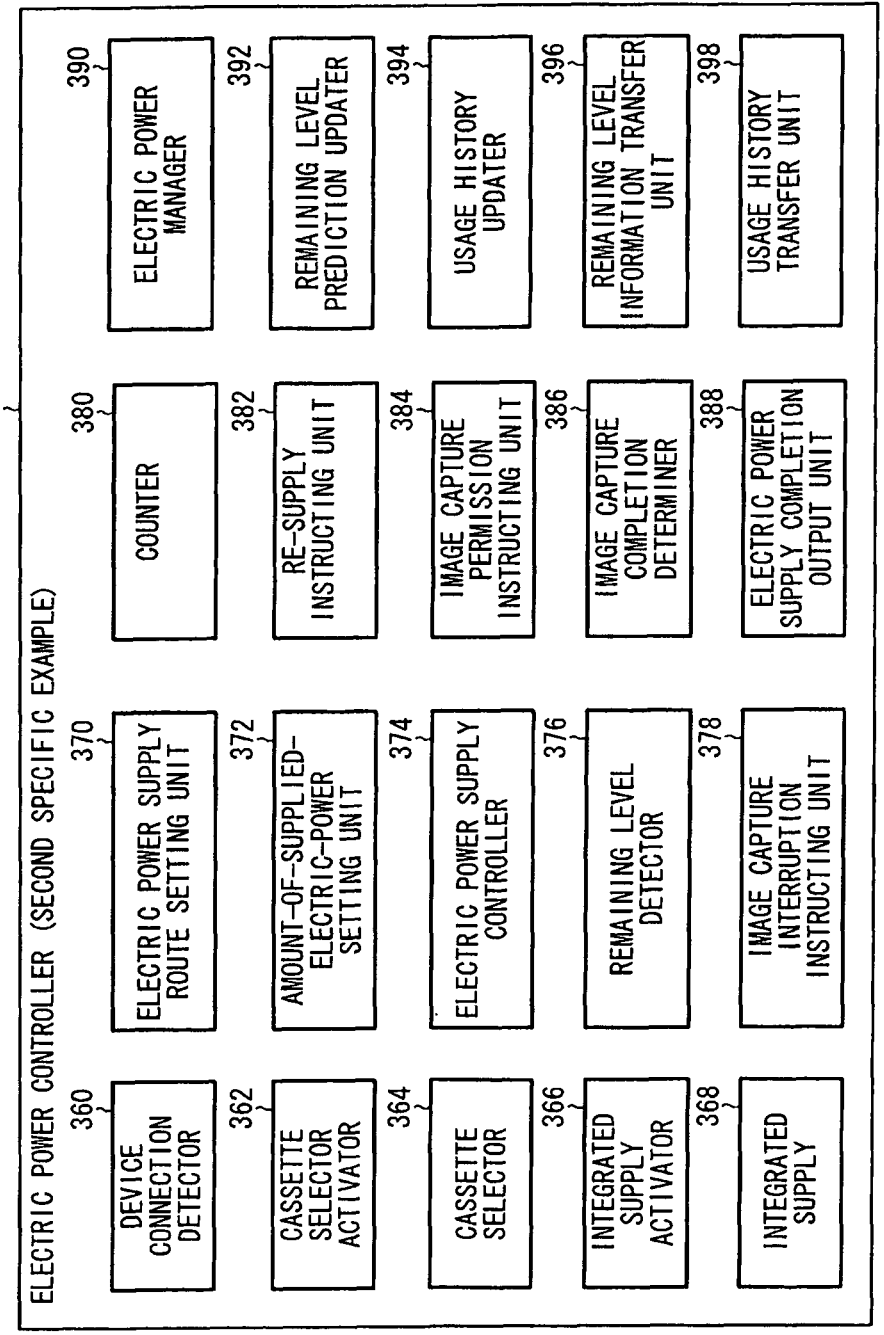
FIG. 19 is a block diagram of a power controller (including a power manager) according to a second specific example.

According to the second specific example, the electric power controller 334 controls supply of electric power such that the remaining levels of electric power stored in the batteries 308 of the connected devices are utilized flexibly between the connected devices, based on preset battery charging conditions and image capturing conditions. As shown in FIG. 19, the electric power controller 334 according to the second specific example comprises, in addition to the functional components shown in FIG. 18, an electric power manager 390 and functional components ancillary to the electric power manager 390, which include a remaining level prediction updater 392, a usage history updater 394, a remaining level information transfer unit 396, and a usage history transfer unit 398. If the activator/deactivator 332 is the third activator/deactivator 332C according to the third mode, then since the device connection detector 360 already is incorporated in the third activator/deactivator 332C, the device connection detector 360 is not included in the electric power controller 334.

Flexible utilization of the remaining levels of electric power stored in the batteries 308 between the connected devices implies at least the following aspects:

(1) One or more devices, the batteries of which store an excessive remaining level of electric power, supply electric power to a device whose battery stores a remaining level of electric power that is not sufficient to capture radiographic images.

(2) One or more devices, which are not used to capture radiographic images, supply electric power required to capture radiographic images to the aforesaid device, which is used to capture radiographic images.

(3) One or more devices, which are not used to capture radiographic images, supply electric power required to capture radiographic images to the aforesaid device, which is used to capture radiographic images, while increasing the remaining level of electric power in the battery of the aforesaid device, i.e., the amount of electric power held by the aforesaid device, up to at least a level required to capture radiographic images.

As shown in FIG. 14, the electric power controller 334 limits supply of electric power during a period in which the electric power controller 334 is supplied with a supply limit signal, which is input thereto from the electric power supply limiter 338. Limiting supply of electric power refers to stopping supply of electric power, reducing the amount of electric power supplied per unit time, or controlling supply of electric power in a stepwise manner. To stop supply of electric power, as shown in FIG. 13, the electric power controller 334 may output a stop signal to the electric power supply controller 374, thereby causing the electric power supply controller 374 to control the first through fifth switchers 314a through 314e in order to change to neutral positions thereof, which are neither input positions nor output positions, for example. In order to reduce the amount of electric power supplied per unit time, the electric power controller 334 may output a supplied-amount reduction signal to the electric power supply controller 374, thereby causing the electric power supply controller 374 to reduce the amount of electric power supplied per unit time to a preset level. In order to control the supply of electric power in a stepwise manner, as described later, the electric power controller 334 may stop supplying electric power while electric charges are being stored in the pixels in the cassette 12 and are converted from analog signals into digital signals, supply a small amount of electric power while image data are being transferred, and supply a large amount of electric power during an idling period after transferring of the image data is completed. The electric power controller 334 stops controlling supply of electric power based on a pause signal, which is input from the pause processor 340, and waits to be activated at a subsequent time by the electric power supply activator 336.

Figure 20:
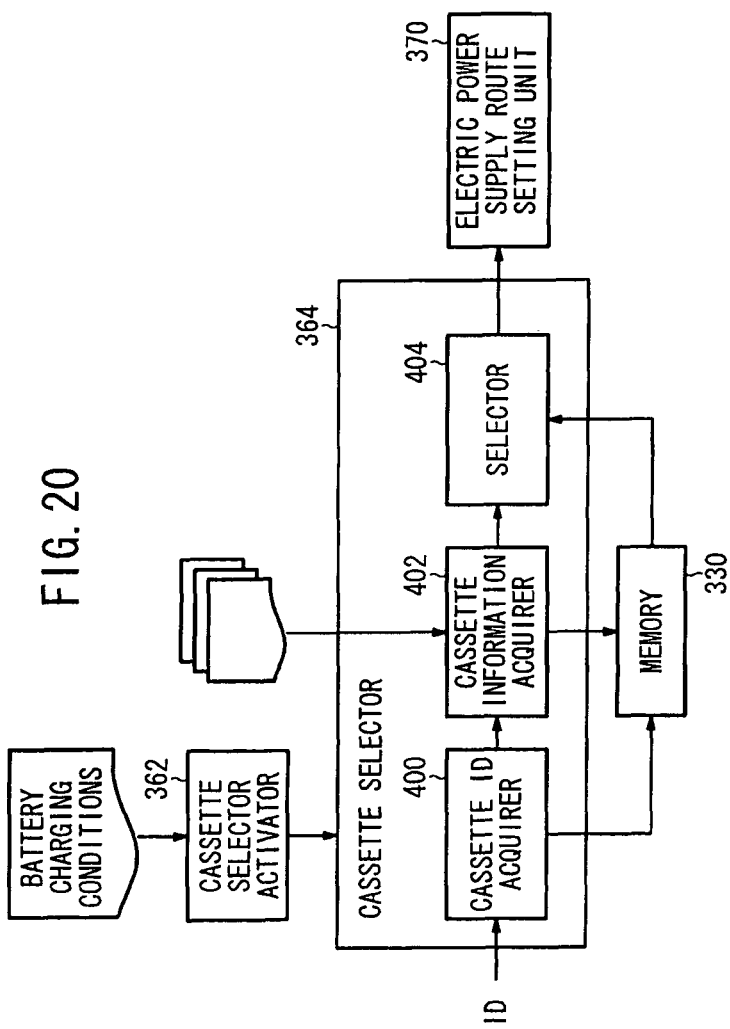
FIG. 20 is a block diagram of a cassette selection activator and a cassette selector.

According to the first specific example, as shown in FIG. 20, the cassette selector activator 362 activates the cassette selector 364 when a condition concerning a route, from among battery charging conditions stored in the memory 330, represents only supply of electric power from one cassette 12 to the radiation source device 18, the aforesaid device is the radiation source device 18, and connection of a plurality of cassettes 12 to the radiation source device 18 is detected.

The cassette selector 364 comprises a cassette ID acquirer 400, a cassette information acquirer 402, and a selector 404.

The cassette ID acquirer 400 sends a transfer request for requesting that the cassettes 12, which are connected to the radiation source device 18, transfer IDs thereof. The cassettes 12 output IDs to the radiation source device 18 based on the transfer request. The cassette ID acquirer 400 acquires the IDs and stores the IDs in the memory 330.

The cassette information acquirer 402 acquires cassette information tables, which contain information concerning defective pixels, etc., and usage history tables corresponding to the acquired IDs via the network.

The selector 404 selects a cassette 12 that matches selecting conditions from among the connected cassettes 12 based on the selecting conditions, the acquired cassette information tables, and the acquired usage history tables, which are stored in the memory 330. The selector 404 then outputs the ID of the selected cassette 12 to the electric power supply route setting unit 370.

The selecting conditions for selecting a cassette 12 include:

(1-a) a large-size cassette 12;

This condition serves the purpose of discharging electric power from a large-size cassette 12 in a special environment where no large-size cassette 12 is used. The size of a cassette 12 is determined based on size information that is recorded in the cassette information table.

(1-b) a small-size cassette 12;

This condition serves the purpose of preferentially discharging electric power from a cassette 12 that is less versatile.

(1-c) a cassette 12 with many defective pixels;

This condition serves the purpose of preferentially discharging electric power from a cassette 12 that is less frequently used, thereby preventing the cassette 12 from becoming disabled substantially simultaneously. The number of defective pixels is determined based on information concerning defective pixels recorded in the cassette information table. The information concerning defective pixels, which is recorded in the cassette information table, is regularly or irregularly updated upon calibration or the like, for example.

(1-d) a cassette 12 with a small imaging area;

The size of an imaging area is calculated from information concerning defective pixels, which is recorded in the cassette information table, particularly positional information about the defective pixels.

(1-e) a cassette 12 with a highly deteriorated battery 308;

The level of deterioration of the battery 308 is determined based on the number of times that the cassette 12 has been used, which is recorded in the cassette information table.

(1-f) a cassette 12 with a lowly deteriorated battery 308;

(1-g) a cassette 12 that has been used many times;

The number of times that the cassette 12 has been used is determined based on a counted number of times that the cassette 12 has been used, which is recorded in the cassette information table, or based on information concerning an accumulated radiation dose, which is recorded in the cassette information table.

(1-h) a cassette 12 with a small remaining built-in memory capacity;

The remaining built-in memory capacity is determined based on a reply, which is sent from the cassette controller 92 in response to an inquiry as to the remaining built-in memory capacity sent to the cassette controller 92.

(1-i) a cassette 12 that is positioned a small distance from the radiation source device 18;

This condition serves the purpose of selecting a cassette 12 that can easily supply electric power over a small distance, thereby reducing the burden on the circuits involved. The distance from the radiation source device 18 to the cassette 12 is determined based on the information concerning present positions of the cassettes 12 acquired via GPS, or distance information from a range sensor such as an ultrasonic sensor, a three-dimensional magnetic sensor, or the like.

Figure 21:
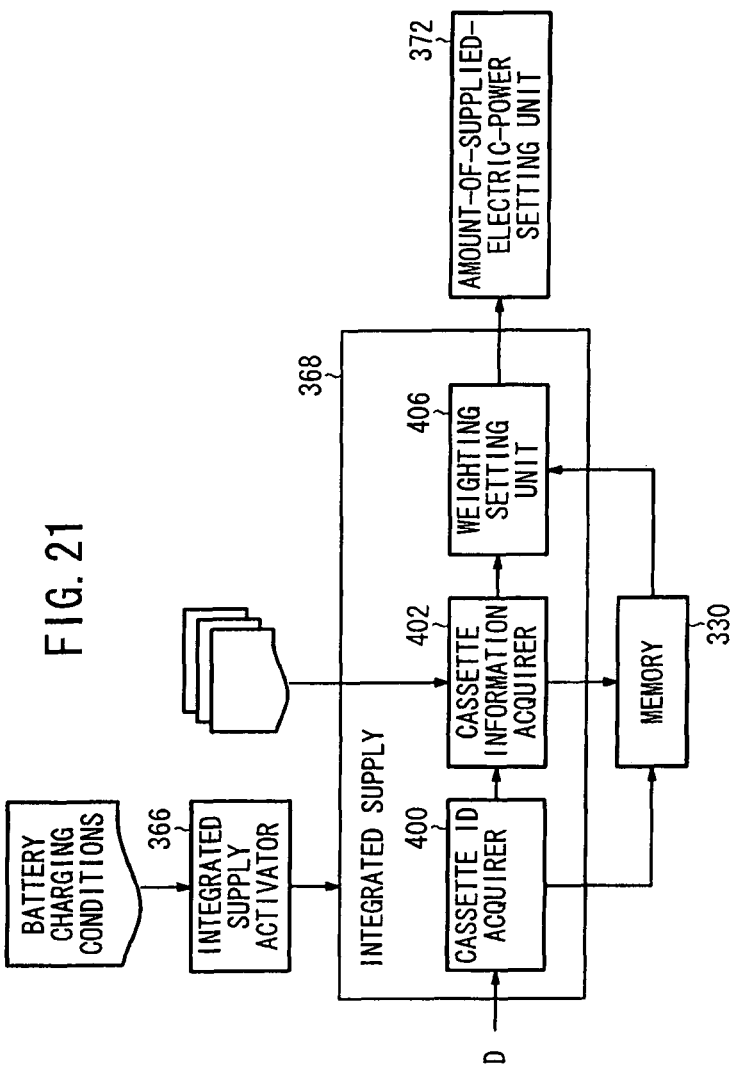
FIG. 21 is a block diagram of an integrated supply activator and an integrated supply.

As shown in FIG. 21, the integrated supply activator 366 activates the integrated supply 368 when a condition concerning a route, from among the battery charging conditions stored in the memory 330, represents only supply of electric power from a plurality of cassettes 12 to the radiation source device 18, the aforesaid device is the radiation source device 18, and connection of a plurality of cassettes 12 to the radiation source device 18 is detected.

The integrated supply 368 comprises a cassette ID acquirer 400, a cassette information acquirer 402, and a weighting setting unit 406.

The cassette ID acquirer 400 sends a transfer request for requesting that cassettes 12 connected to the radiation source device 18 transfer IDs thereof. The cassettes 12 output IDs to the radiation source device 18 based on the transfer request. The cassette ID acquirer 400 acquires the IDs and stores the IDs in the memory 330.

The cassette information acquirer 402 acquires cassette information tables, which contain information concerning defective pixels, etc., and usage history tables corresponding to the acquired IDs via the network.

The weighting setting unit 406 sets weighting coefficients for respective amounts of electric power to be supplied from the cassettes 12 to the radiation source device 18, based on integrating conditions, the acquired cassette information tables, and the acquired usage history tables, which are stored in the memory 330. The weighting setting unit 406 then outputs the set weighting coefficients, together with corresponding ID information, to the amount-of-supplied-electric-power setting unit 372.

The integrating conditions include:

(2-a) The amount of supplied electric power is sorted depending on the amount of defective pixels;

As the number of defective pixels becomes greater, the weighting setting unit 406 sets a weighting coefficient for increasing the amount of supplied electric power. Conversely, as the number of defective pixels becomes smaller, the weighting setting unit 406 sets a weighting coefficient for reducing the amount of supplied electric power.

(2-b) The amount of supplied electric power is sorted depending on the imaging area;

As the imaging area becomes smaller, the weighting setting unit 406 sets a weighting coefficient for increasing the amount of supplied electric power. Conversely, as the imaging area becomes greater, the weighting setting unit 406 sets a weighting coefficient for reducing the amount of supplied electric power.

(2-c) The amount of supplied electric power is sorted depending on the level of deterioration of the battery 308;

As the level of deterioration of the battery 308 becomes greater, the weighting setting unit 406 sets a weighting coefficient for increasing the amount of supplied electric power. Conversely, as the level of deterioration of the battery 308 becomes smaller, the weighting setting unit 406 sets a weighting coefficient for reducing the amount of supplied electric power.

(2-d) The amount of supplied electric power is sorted depending on the number of times that the cassette 12 has been used;

As the number of times that the cassette 12 has been used becomes greater, the weighting setting unit 406 sets a weighting coefficient for increasing the amount of supplied electric power. Conversely, as the number of times that the cassette 12 has been used is smaller, the weighting setting unit 406 sets a weighting coefficient for reducing the amount of supplied electric power.

(2-e) The amount of supplied electric power is sorted depending on the remaining built-in memory capacity;

As the amount of supplied electric power becomes smaller, the weighting setting unit 406 sets a weighting coefficient for increasing the amount of supplied electric power. Conversely, as the amount of supplied electric power becomes greater, the weighting setting unit 406 sets a weighting coefficient for reducing the amount of supplied electric power.

(2-f) The amount of supplied electric power is sorted depending on the distance to the radiation source device 18.

As the distance to the radiation source device 18 becomes smaller, the weighting setting unit 406 sets a weighting coefficient for increasing the amount of supplied electric power. Conversely, as the distance to the radiation source device 18 becomes greater, the weighting setting unit 406 sets a weighting coefficient for reducing the amount of supplied electric power.

Then, the electric power supply route setting unit 370 sets a route for supply of electric power based on a condition concerning the route from among the battery charging conditions stored in the memory 330. For example, the electric power supply route setting unit 370 sets a route from the radiation source device 18 to the cassette 12, or a route from the cassette 12 to the radiation source device 18. If the electric power supply route setting unit 370 is supplied with an ID from the cassette selector 364, then the electric power supply route setting unit 370 sets a route from the cassette 12 to the radiation source device 18 corresponding to the ID. If the electric power supply route setting unit 370 is supplied with a plurality of IDs from the integrated supply 368, then the electric power supply route setting unit 370 sets routes from the cassettes 12 to the radiation source device 18 corresponding to such IDs. Route information representing the set IDs is displayed on a display screen of the mobile terminal 42. The condition concerning the route is descriptive of at least one source of electric power. If the source of electric power is the radiation source device 18, then the radiation source device 18 supplies electric power to the cassette 12. If the source of electric power is the cassette 12, then the cassette 12 supplies electric power to the radiation source device 18. The condition concerning the route can be changed as desired by the mobile terminal 42. If the re-supply instructing unit 382 provides a re-supply instruction, i.e., if the re-supply instructing unit 382 inputs a re-supply instruction signal to the electric power supply route setting unit 370, then the electric power supply route setting unit 370 sets the route for supply of electric power based on battery charging conditions. If the operator 38 intends to additionally charge the battery of another device, e.g., the radiation source device 18 or the cassette 12, then the operator 38 enters the route for supply of electric power to the other device, i.e., a route from the other device to the radiation source device 18 or the cassette 12 that is used to capture radiographic images, or a route from the radiation source device 18 or the cassette 12 that is used to capture radiographic images to the other device, and also enters an amount of electric power to be supplied. Based on the entered route for supply of electric power, the electric power supply route setting unit 370 outputs a supply source instruction signal or a supply destination instruction signal to the electric power supply controller 374 of each device.

The amount-of-supplied-electric-power setting unit 372 sets an amount of electric power to be supplied based on a condition concerning the amount of electric power to be supplied, from among the battery charging conditions. At least items such as a full battery charge, an amount of electric power to be supplied that is required to capture a single radiographic image, etc., can be used as conditions concerning the amount of electric power to be supplied. One of such items, which is selected at present, is applicable as the condition concerning the amount of electric power to be supplied. An item to be applied can be selected as desired by the mobile terminal 42. An amount of electric power to be supplied can be set as a numerical value by the mobile terminal 42. If the amount-of-supplied-electric-power setting unit 372 is supplied with a plurality of IDs and corresponding coefficients from the integrated supply 368, then the amount-of-supplied-electric-power setting unit 372 multiplies the amount of electric power to be supplied by such coefficients in order to set amounts of electric power to be supplied respectively from the cassettes 12 to the radiation source device 18. If the re-supply instructing unit 382 provides a re-supply instruction, then the amount-of-supplied-electric-power setting unit 372 sets an amount of electric power to be supplied based on a condition concerning the amount of electric power to be supplied, from among the battery charging conditions. The amount of electric power to be supplied can also be changed as desired by the mobile terminal 42. If batteries of devices are to be charged as well, then the amount-of-supplied-electric-power setting unit 372 also sets respective amounts of electric power to be supplied in order to charge the batteries, and supplies the set amounts of electric power to be supplied to the electric power supply controllers 374 of each of the respective devices.

As shown in FIG. 13, if a supply source instruction signal is input to the electric power supply controller 374, then the electric power supply controller 374 controls the battery 308 in order to output electric power. If a supply destination instruction signal is input to the electric power supply controller 374, then the electric power supply controller 374 controls the battery 308 in order to receive electric power. Based on a remaining level of electric power in the battery 308, which is detected by the remaining level detector 376, the electric power supply controller 374 controls the battery 308 that is supplied with electric power at a constant charging rate, or controls the battery 308 to supply electric power at the constant discharging rate. Assuming that the amount of electric power to be supplied is small, then the electric power supply controller 374 can quickly charge or discharge the battery 308. If the remaining level of electric power in the battery 308, which is detected by the remaining level detector 376, is insufficient to capture a single radiographic image, then the electric power supply controller 374 outputs an imaging disable signal, which includes the remaining level of electric power and the ID of the aforesaid device. When the supply of electric power to the battery 308 or the supply of electric power from the battery 308 is completed, the electric power supply controller 374 outputs a supply termination signal.

As described above, the remaining level detector 376 detects a remaining level of electric power in the battery 308, and sends a signal representative of the detected remaining level of electric power in the battery 308 to the electric power supply controller 374.

The image capture interruption instructing unit 378, as shown in FIG. 18, outputs a message representing interruption of an image capturing process to the mobile terminal 42, based on an imaging disabled signal input from the electric power supply controller 374.

The counter 380 counts the number of times that the exposure switch 48 has been turned on. The counter 380 resets the count (count=0) based on an image capture completion signal, which is input from the image capture completion determiner 386.

Based on the imaging disabled signal input from the electric power supply controller 374, the re-supply instructing unit 382 outputs a re-supply instruction signal including the preset count of the counter 380, the amount of electric power included in the imaging disabled signal, and the ID of the aforesaid device, respectively, to the electric power supply route setting unit 370, the amount-of-supplied-electric-power setting unit 372, and the electric power manager 390. If electric power is supplied after capturing of radiographic images, since the electric power controller 334 itself is not activated, the re-supply instructing unit 382 of the radiation source device 18 or the cassette 12 that is used to capture radiographic images activates the electric power supply route setting unit 370, the amount-of-supplied-electric-power setting unit 372, and the electric power manager 390, using an interrupt routine for emergency.

If the supply timing conditions recorded in the memory 330 are free of timing controls, or indicate supply electric power before capturing of radiographic images, then the image capture permission instructing unit 384 outputs an image capture permission message to the mobile terminal 42 based on supply termination signals, which are input from the electric power supply controllers 374 of all of the devices to which electric power is supplied.

The image capture completion determiner 386 compares the number of times that radiographic images have been captured in the image capturing conditions with the count of the counter 380, and outputs an image capture completion signal when the number of times that radiographic images have been captured becomes equal to the count.

The electric power supply completion output unit 388 outputs an electric power supply completion signal based on supply termination signals, which are input from the electric power supply controllers 374 of all of the devices to which electric power is supplied.

The electric power supply limiter 338 shown in FIG. 14 determines whether or not a radiographic image of the subject 50 is being captured if the supply timing conditions recorded in the memory 330 include a condition indicating that "the supply of electric power is stopped while a radiographic image is being captured." If a radiographic image is being captured, then the electric power supply limiter 338 outputs a supply limit signal during the period in which a radiographic image is being captured. More specifically, when the exposure switch 48 is turned on, the electric power supply limiter 338 outputs a supply limit signal. Thereafter, when a predetermined period of time has elapsed, the electric power supply limiter 338 stops outputting the supply limit signal. The electric power controller 334 limits supply of electric power during the period in which the supply limit signal is input thereto.

The period during which the electric power supply limiter 338 outputs the supply limit signal should preferably be any one of a period (storage period) in which radiation 46 having passed through the subject 50 is applied to the radiation detector 86 and converted by a scintillator (not shown) into visible light, and the visible light is converted at each pixel 132 into electric signals that are stored as electric charges (signal charges), a period (reading period) during which the stored electric charges are read, and a period (analog-to-digital conversion period) during which the read electric charges (analog signals) are converted into digital signals by the A/D converter 154, a period which is a combination of the above periods, or a period that includes all the above periods. In the above three periods, the image signals (radiographic image information) are highly susceptible to noise. More specifically, in the storage period and the reading period, since the level of electric charge is very low, the radiographic image information is highly susceptible to noise. In the analog-to-digital conversion period, analog signals are less resistant to noise than digital signals, and any noise added to the analog signals tends to be converted into digital signals and appear in the image data.

The storage period includes a period during which the radiation source 44 emits radiation 46. More specifically, after the storage period has started, the radiation source 44 begins to emit radiation 46 as quickly as possible, and after the radiation source 44 has stopped emitting radiation 46, the stored electric charges are read immediately from the pixels. Any time lag associated with these processes should be reduced as much as possible in order to reduce dark current, and hence increase the quality of radiographic images that are generated. The reading period refers to a period during which the TFTs 140 are turned on, and signals are supplied through the amplifiers 148 to the A/D converter 154. The reading period and the analog-to-digital conversion period occur substantially at the same time, although the reading time starts slightly earlier than the analog-to-digital conversion period.

The period during which the supply limit signal is output should extend from a time when the supply limit signal is output to a time when the radiation source device 18 stops emitting radiation 46, or more preferably reside within the period during which the radiographic image is captured, so that the cassette 12 can detect radiation 46 with high quality. A predicted time, which is required to capture and display a radiographic image, may be preset and used as the period during which the supply limit signal is output. The degree to which the amount of supplied electric power is reduced per unit time may be set experimentally to a value for preventing noise from being added to the radiographic image, or for reducing any added noise to a level that is not detrimental to the quality of the radiographic image.

If the supply timing conditions recorded in the memory 330 are free of timing controls, or indicate supply of electric power before capturing of radiographic images, then the pause processor 340 shown in FIG. 14 outputs a pause signal to the electric power controller 334, based on an image capture completion signal input from an image capture completion determiner 386. If the supply timing conditions recorded in the memory 330 indicate supply of electric power after capturing of radiographic images, then the pause processor 340 outputs a pause signal to the electric power controller 334, based on an electric power supply completion signal input from the electric power supply completion output unit 388.

Figure 22:
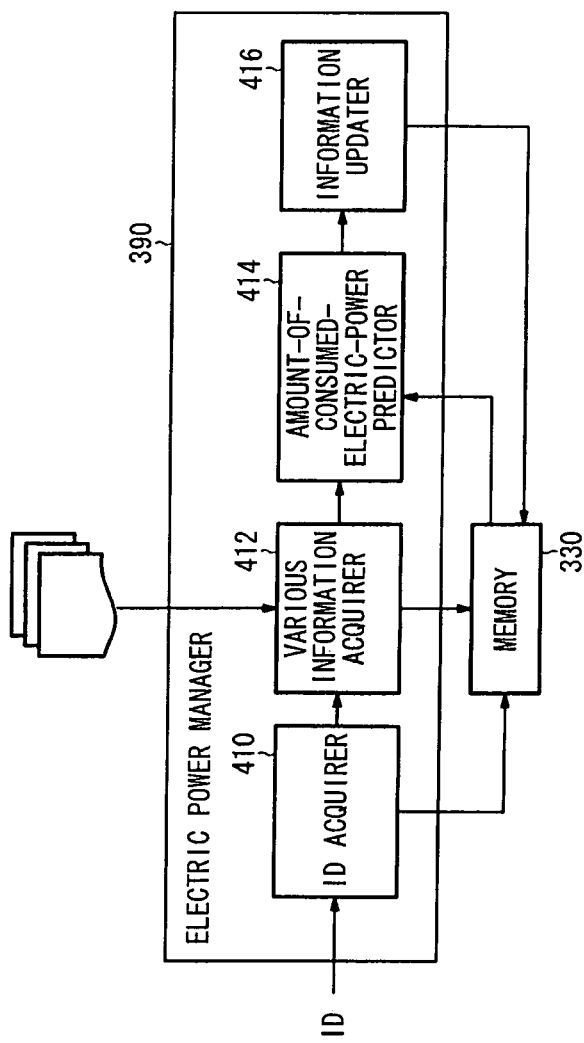
FIG. 22 is a block diagram of a power manager.

According to the second specific example, the electric power manager 390 shown in FIG. 19 gives the electric power supply controller 374 information for controlling supply of electric power, such that the remaining levels of electric power stored in the batteries 308 of the devices are utilized flexibly between the devices, based on preset battery charging conditions and image capturing conditions. The electric power manager 390 is incorporated in the radiation source device 18 and/or the cassette 12. As shown in FIG. 22, the electric power manager 390 comprises an ID acquirer 410, an information acquirer 412 for acquiring various information, an amount-of-consumed-electric-power predictor 414, and an information updater 416.

The ID acquirer 410 sends a transfer request for requesting the device that incorporates the electric power manager 390 therein and another device that is connected to the device to transfer respective IDs thereof. Based on the transfer request, the devices output their IDs respectively to the electric power manager 390. The ID acquirer 410 acquires the IDs input thereto and registers the acquired IDs in the memory 330. If another radiation source device 18 or another cassette 12, in addition to the radiation source device 18 and the cassette 12 used to capture radiographic images, are connected or are present in an area in which they can be fed wirelessly, then the ID acquirer 410 also acquires IDs of the other radiation source device 18 and the cassette 12.

The information acquirer 412 for acquiring various information acquires present or previous image capturing conditions, which are input via the mobile terminal 42 or the network, remaining level-of-electric-energy information tables corresponding to the IDs, previous image capturing conditions corresponding to the IDs, and usage history tables corresponding to the IDs, and stores such information in the memory 330.

The amount-of-consumed-electric-power predictor 414 calculates amounts of electric power that are consumed by the radiation source device 18 and the cassette 12 used to capture radiographic images, from the battery charging conditions stored in the memory 330 and the present or previous image capturing conditions representative of the number of radiographic images to be captured, mAs values, etc. The amount-of-consumed-electric-power predictor 414 then corrects the calculated amounts of electric power by multiplying the calculated amounts by usage histories of the radiation source device 18 and the cassette 12, i.e., coefficients corresponding to the number of times that the radiation source device 18 and the cassette 12 have been used, thereby predicting amounts of electric power that will be consumed by the radiation source device 18 and the cassette 12 during the present image capturing process, or amounts of electric power consumed by the radiation source device 18 and the cassette 12 in the previous image capturing process. If a re-supply instruction is input from the re-supply instructing unit 382, then the amount-of-consumed-electric-power predictor 414 calculates amounts of electric power to be consumed by the respective devices indicated by the IDs, i.e., the radiation source device 18 and the cassette 12 to be re-supplied with electric power, from image capturing conditions for the image capturing process to be carried out, from which image capturing conditions for radiographic images already captured (indicated by the count) are excluded, which are among the present image capturing conditions representative of the number of radiographic images to be captured, mAs values, etc., and corrects the calculated amounts of electric power by multiplying the calculated amounts by usage histories of the radiation source device 18 and the cassette 12, i.e., coefficients corresponding to the number of times that the radiation source device 18 and the cassette 12 have been used, thereby predicting amounts of electric power that will be consumed by the devices of the IDs in the image capturing process to be carried out.

The information updater 416 subtracts the amount of supplied electric power from the remaining level of electric power of a device serving as an electric power supply source, and adds the amount of supplied electric power to the remaining level of electric power of a device that serves as an electric power supply destination, in the remaining level-of-electric-energy information table. If the re-supply instructing unit 382 outputs a re-supply instruction, then the information updater 416 changes only the remaining levels of electric power of the respective devices indicated by the IDs. A value produced by adding the present amount of supplied electric power to the amount of electric power included in the re-supply instruction signal is recorded in the memory 330. Since this value reflects the amount of electric power from the electric power supply controller 374, an error in the remaining level of electric power, which is represented by only a predicted value, is corrected.

According to the second specific example, because the electric power controller 334 includes the electric power manager 390, the electric power supply route setting unit 370 and the amount-of-supplied-electric-power setting unit 372 operate differently from those of the electric power controller 334 according to the first specific example.

More specifically, the electric power supply route setting unit 370 according to the second specific example sets a route for supply of electric power based on the predicted amount of electric power, and the remaining levels of electric power in the batteries 308 of the radiation source device 18 and the cassette 12 (remaining level-of-electric-energy information tables). Typically, the electric power supply route setting unit 370 sets a route for supplying electric power to a device, the battery of which stores a remaining level of electric power that will almost be eliminated in the present image capturing process. Information concerning the set route is displayed on the display screen of the mobile terminal 42. If the re-supply instructing unit 382 outputs a re-supply instruction, then the electric power supply route setting unit 370 sets routes for supplying electric power to respective devices indicated by the IDs. If the operator 38 intends to supply electric power additionally from other devices, i.e., a radiation source device 18 and a cassette 12 that are not used to capture radiographic images, then the operator 38 enters routes for supplying electric power, and amounts of electric power, from the other devices, i.e., routes for supplying electric power from the other devices to the respective devices indicated by the IDs. If the operator 38 additionally intends to charge a battery using another device, i.e., a radiation source device 18 or a cassette 12, then the operator 38 enters a route for supplying electric power to or from the other device, i.e., a route from the other device to the radiation source device 18 or the cassette 12 that is used to capture radiographic images, or a route from the radiation source device 18 or the cassette 12 that is used to capture radiographic images to the other device, together with the amount of electric power to be supplied, and an order in which such electric power is supplied. Based on the entered route for supplying electric power, the electric power supply route setting unit 370 outputs a supply source instruction signal or a supply destination instruction signal to the electric power supply controller 374 of each of the devices.

The amount-of-supplied-electric-power setting unit 372 according to the second specific example sets the supplied amount of electric power based on the predicted amount of electric power and the remaining levels of electric power in the batteries 308 of the radiation source device 18 and the cassette 12 (remaining level-of-electric-energy information tables). Thus, at most, the predicted amount of electric power is supplied to a device, the battery of which stores a remaining level of electric power, which will almost be eliminated during the present image capturing process. The amount of electric power, which is supplied to such a device, may be one-half or one-third the predicted amount of electric power. The information concerning the set amount of electric power is displayed on a display screen of the mobile terminal 42. The set amount of electric power can also be changed as desired by the mobile terminal 42. If the operator 38 additionally intends to charge a battery, then the amount-of-supplied-electric-power setting unit 372 also sets the amount of electric power to be supplied, so as to additionally charge the battery. The amount of electric power predicted based on previous image capturing conditions is supplied in order to supplement the amount of electric power consumed in the previous image capturing process. If the re-supply instructing unit 382 outputs a re-supply instruction, then the amount-of-supplied-electric-power setting unit 372 sets the amount of electric power to equal the predicted amount of electric power. The set amount of electric power can be changed as desired by the mobile terminal 42. If the operator 38 additionally intends to charge a battery, then the amount-of-supplied-electric-power setting unit 372 also sets an amount of electric power to be supplied, so as to additionally charge the battery. The set amount of electric power then is supplied to the electric power supply controller 374 of the corresponding device.

Among functional components that are ancillary to the electric power manager 390, the remaining level prediction updater 392 shown in FIG. 19 functions, assuming that the supply timing conditions recorded in the memory 330 indicate supply of electric power before capturing of radiographic images. Each time that the operator 38 turns on the exposure switch 48, the remaining level prediction updater 392 updates, by way of subtraction, the remaining levels of electric power stored in the batteries that are recorded in the remaining level-of-electric-energy information tables, i.e., the remaining levels of electric power stored in the batteries 308 of the radiation source device 18 and the cassette 12, which are used to capture radiographic images. More specifically, with respect to the radiation source device 18 and the cassette 12, the remaining level prediction updater 392 calculates amounts of electric power consumed in order to capture radiographic images based on the image capturing conditions and the usage history tables, and subtracts the calculated amounts of electric power from the remaining levels of electric power stored in the batteries 308 of the radiation source device 18 and the cassette 12, which are recorded in the remaining level-of-electric-energy information tables.

The usage history updater 394 adds to the usage counts recorded in the usage history tables the number of times that the exposure switch 48 has been turned on, i.e., the number of times that the radiation source device 18 and the cassette 12 have been used.

If the supply timing conditions recorded in the memory 330 indicate supply of electric power before capturing of radiographic images, then the remaining level information transfer unit 396 shown in FIG. 19 transfers the remaining level-of-electric-energy information tables via the network to the database of a data center, such as a medical organization or the like for updating, based on an image capture completion signal input from the image capture completion determiner 386. If the supply timing conditions recorded in the memory 330 indicate supply of electric power after capturing of radiographic images, then the remaining level information transfer unit 396 transfers the remaining level-of-electric-energy information tables via the network to the database of the data center for updating, based on an electric power supply completion signal input from the electric power supply completion output unit 388.

If the supply timing conditions recorded in the memory 330 indicate supply of electric power before capturing of radiographic images, then the usage history transfer unit 398 transfers the usage history tables via the network to the database of the data center for updating, based on an image capture completion signal input from the image capture completion determiner 386. If the supply timing conditions recorded in the memory 330 indicate supply of electric power after capturing of radiographic images, then the usage history transfer unit 398 transfers the usage history tables via the network to the database of the data center for updating, based on an electric power supply completion signal input from the electric power supply completion output unit 388.

The first radiographic image capturing apparatus 10A basically is constructed as described above. Operations of the first radiographic image capturing apparatus 10A will be described below with reference to the flowcharts shown in FIGS. 23 through 29.

First, an operation sequence of the first radiographic image capturing apparatus 10A, if the supply timing conditions are free of timing controls, will be described below with reference to the flowcharts shown in FIGS. 23 and 24.

Figure 23:
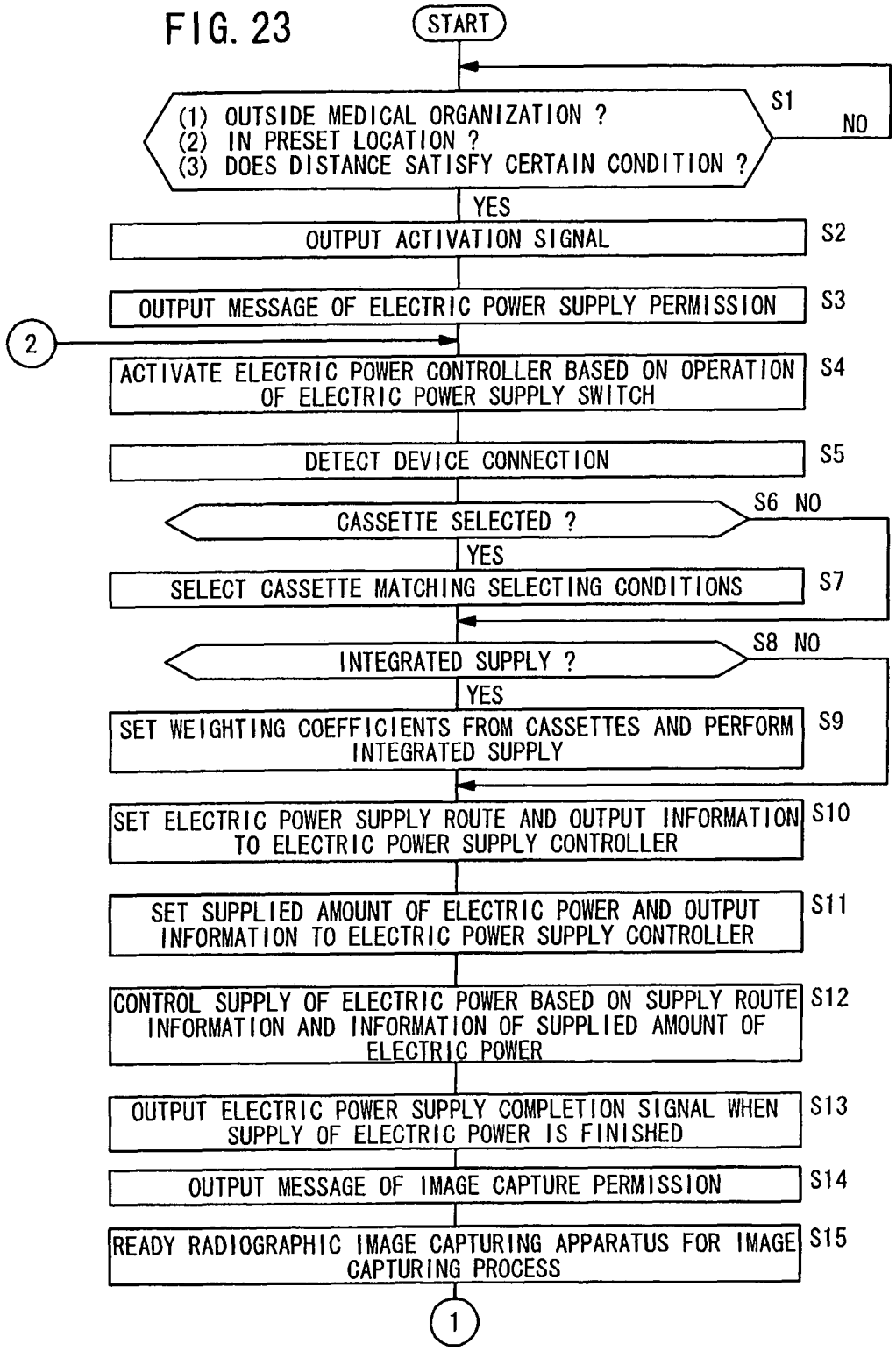
FIG. 23 is a first flowchart of an operation sequence of the first radiographic image capturing apparatus, operated under supply timing conditions, which are free of timing controls.

In step S1 shown in FIG. 23, the activator/deactivator 332 performs a determining process. More specifically, if the activator/deactivator 332 is the first activator/deactivator 332A (see FIGS. 15A and 15B), then the first activator/deactivator 332A determines whether or not the first present position is outside of a medical organization. If the operator 38 carries the first radiographic image capturing apparatus 10A, the devices of which are coupled together, out of the medical organization while gripping the grip 24, then control proceeds to step S2, during which the first activator/deactivator 332A outputs an activation signal.

If the activator/deactivator 332 is the second activator/deactivator 332B (see FIGS. 16A and 16B), then the second activator/deactivator 332B determines whether or not the second present position is in a preset location, i.e., at the location indicated by the area information registered in the second location information table 331B, such as a medical organization, an accident site, a disaster site, a medical checkup site, a home-care service site, or a transport vehicle such as an ambulance, a mobile medical checkup motor vehicle, a railway car, a ship, an aircraft, or the like. If the operator 38 carries the first radiographic image capturing apparatus 10A, the devices of which are coupled together, into the preset location while gripping the grip 24, then control proceeds to step S2, during which the second activator/deactivator 332B outputs an activation signal.

If the activator/deactivator 332 is the third activator/deactivator 332C (see FIGS. 17A through 17C), then the third activator/deactivator 332C determines whether or not the distance between the aforesaid device and another device satisfies a certain condition. More specifically, the third activator/deactivator 332C according to the first mode (see FIG. 17A) determines whether or not the linear distance between the third present position (the aforesaid device) and the fourth present position (another device) is equal to or smaller than a preset reference distance. The third activator/deactivator 332C according to the second mode (see FIG. 17B) determines whether or not an answer signal has arrived from the other device within a preset response time from when the aforesaid device outputs a request signal, i.e., whether the distance between the devices is within the communication range of each of the devices. The third activator/deactivator 332C according to the third mode (see FIG. 17C) determines whether or not a device (the radiation source device 18 or the cassette 12) is connected to at least one of the first energy input/output unit 300 and the second energy input/output unit 302 in a wired fashion or a wireless fashion, i.e., whether the distance between the devices is sufficient for the devices to be connected in a wired fashion, or whether the distance between the devices allows them to be fed wirelessly.

When the operator 38 approaches the radiation source device 18 and the cassette 12 of the first radiographic image capturing apparatus 10A toward one another until the linear distance between such devices is equal to or smaller than the reference distance, when the distance between the devices enters within the communication range, or when the distance between the devices allows the devices to be connected in a wired fashion or wireless fashion, then the third activator/deactivator 332C outputs an activation signal in step S2.

Thereafter, in step S3, the electric power supply permission instructing unit 350 outputs a message indicating permission to supply electric power to the mobile terminal 42 and/or to energize (de-energize) the pilot lamp.

In step S4, the electric power controller 334 is activated based on operation of the electric power supply switch. The electric power supply activator 336 may also activate the electric power controller 334 without waiting for operation of the electric power supply switch. At this time, the electric power supply activator 336 of each of the devices refers to interlock information registered in the memory 330, i.e., an ID of the radiation source device 18 or the cassette 12 that is used in a preset image capturing process, and only the electric power supply activator 336 of the device having an ID is identical to that of the interlock information activates the corresponding electric power controller 334.

In step S5, the device connection detector 360 detects whether or not the device, i.e., the radiation source device 18 or the cassette 12, is connected to the first energy input/output unit 300 or to the second energy input/output unit 302. If the activator/deactivator 332 is the third activator/deactivator 332C (see FIG. 17C), then since the device connection detector 360 has already detected connection thereof in step S1, control proceeds from step S4 to step S6, while skipping step S5.

After the device connection detector 360 has detected the connection in step S5, the cassette selector activator 362 determines whether or not conditions are satisfied for activating the cassette selector 364 in step S6. More specifically, the cassette selector activator 362 activates the cassette selector 364 when a condition concerning a route, from among the battery charging conditions stored in the memory 330, represents only supply of electric power from one cassette 12 to the radiation source device 18, the aforesaid device is the radiation source device 18, and connection of a plurality of cassettes 12 to the radiation source device 18 is detected.

In step S7, the cassette selector 364 selects a cassette 12 that matches the selecting conditions from among the connected cassettes 12, based on a plurality of IDs that are acquired by the cassette ID acquirer 400, selecting conditions stored in the memory 330, and the cassette information tables and the usage history tables, which are acquired by the cassette information acquirer 402. The cassette selector 364 then outputs the ID of the selected cassette 12 to the electric power supply route setting unit 370.

After step S7, or if the cassette selector activator 362 judges that conditions are not satisfied for activating the cassette selector 364 in step S6, control proceeds to step S8, during which the integrated supply activator 366 determines whether conditions are not satisfied in order to activate the integrated supply 368. More specifically, the integrated supply activator 366 activates the integrated supply 368 when a condition concerning a route, from among the battery charging conditions stored in the memory 330, represents only supply of electric power from a plurality of cassettes 12 to the radiation source device 18, the aforesaid device is the radiation source device 18, and connection of a plurality of cassettes 12 to the radiation source device 18 is detected.

In step S9, the integrated supply 368 sets weighting coefficients for the amounts of electric power to be supplied from the cassettes 12 to the radiation source device 18 based on a plurality of IDs that are acquired by the cassette ID acquirer 400, integrating conditions stored in the memory 330, the cassette information tables, and the usage history tables, which are acquired by the cassette information acquirer 402. The integrated supply 368 then outputs the set weighting coefficients to the corresponding amount-of-supplied-electric-power setting unit 372.

After step S9, or if the integrated supply activator 366 judges that conditions are not satisfied for activating the integrated supply 368 in step S8, then control proceeds to step S10, during which the electric power supply route setting unit 370 sets a route for supply of electric power, based on conditions concerning the route from among the battery charging conditions stored in the memory 330. For example, the electric power supply route setting unit 370 sets a route from the radiation source device 18 to the cassette 12, or a route from the cassette 12 to the radiation source device 18. If the electric power supply route setting unit 370 is supplied with an ID from the cassette selector 364, then the electric power supply route setting unit 370 sets a route from the cassette 12 identified by the ID to the radiation source device 18. If the electric power supply route setting unit 370 is supplied with a plurality of IDs from the integrated supply 368, then the electric power supply route setting unit 370 sets multiple routes from the cassettes 12 identified by the IDs to the radiation source device 18. Thereafter, the electric power supply route setting unit 370 outputs information concerning the set route (route information) to the electric power supply controller 374. More specifically, based on the set route for supply of electric power, the electric power supply route setting unit 370 outputs a supply source instruction signal, or a supply destination instruction signal, to the electric power supply controller 374 of each device. For example, it is assumed that the first energy input/output unit 300 of the radiation source device 18 is connected to the first energy input/output unit 300 of the cassette 12. If the set route is a route for supplying electric power from the radiation source device 18 to the cassette 12, then the electric power supply route setting unit 370 outputs a supply source instruction signal to the electric power supply controller 374 of the radiation source device 18, and further outputs a supply destination instruction signal to the electric power supply controller 374 of the cassette 12. If the set route is a route for supplying electric power from the cassette 12 to the radiation source device 18, then the electric power supply route setting unit 370 outputs a supply destination instruction signal to the electric power supply controller 374 of the radiation source device 18, and further outputs a supply source instruction signal to the electric power supply controller 374 of the cassette 12.

In step S11, the amount-of-supplied-electric-power setting unit 372 sets an amount of electric power to be supplied (supplied amount of electric power) based on a condition concerning the amount of electric power to be supplied, from among the battery charging conditions. For example, the amount-of-supplied-electric-power setting unit 372 sets an amount of electric power to be supplied for a full battery charge, or for capturing a single radiographic image. If the amount-of-supplied-electric-power setting unit 372 is supplied with a plurality of IDs and corresponding coefficients from the integrated supply 368, then the amount-of-supplied-electric-power setting unit 372 multiplies the amount of electric power to be supplied by such coefficients in order to set respective amounts of electric power to be supplied to the radiation source device 18 from the respective cassettes 12. The amount-of-supplied-electric-power setting unit 372 outputs information concerning the set amounts of electric power to be supplied to the electric power supply controllers 374 of the corresponding devices.

In step S12, if the electric power supply controller 374 is supplied with a supply source instruction signal, then the electric power supply controller 374 controls the battery 308 in order to output electric power. Further, if the electric power supply controller 374 is supplied with a supply destination instruction signal, then the electric power supply controller 374 controls the battery 308 so as to be supplied with electric power. When supply of electric power to the battery 308 or supply of electric power from the battery 308 is completed, then the electric power supply controller 374 outputs a supply termination signal.

In step S13, the electric power supply completion output unit 388 outputs an electric power supply completion signal based on supply termination signals, which are input from the electric power supply controllers 374 of all of the devices to which electric power has been supplied.

In step S14, the image capture permission instructing unit 384 outputs a message representative of permission to capture an image to the mobile terminal 42, based on the electric power supply completion signal input from the electric power supply completion output unit 388.

In step S15, the operator 38 prepares the first radiographic image capturing apparatus 10A for capturing radiographic images at a site where the first radiographic image capturing apparatus 10A has been carried. This preparatory procedure has been described in detail above, and will not be described below.

Figure 24:
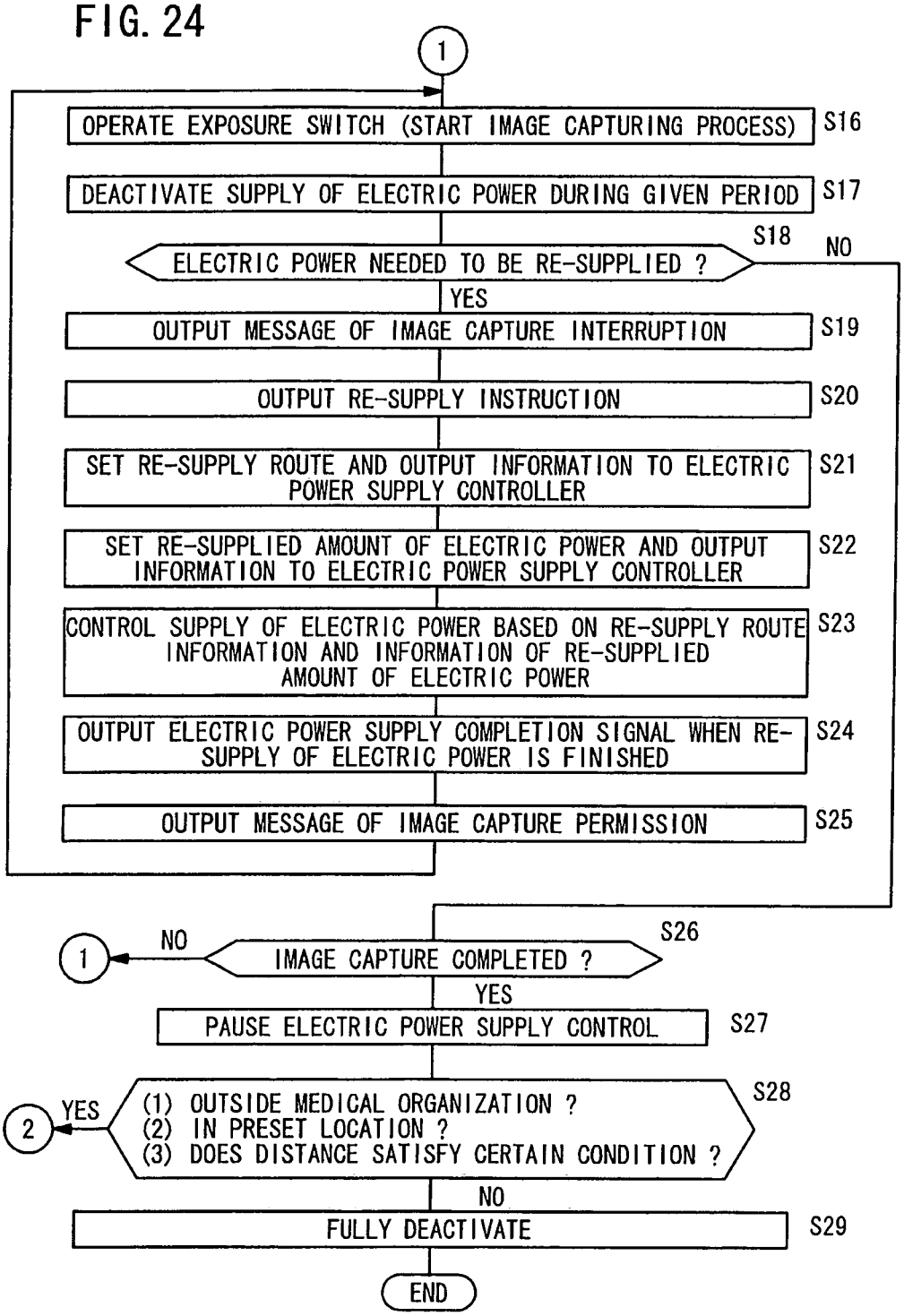
FIG. 24 is a second flowchart of an operation sequence of the first radiographic image capturing apparatus, operated under supply timing conditions, which are free of timing controls.

When the subject 50 is positioned during the preparatory procedure, control proceeds to step S16 shown in FIG. 24, in which the operator 38 turns on the exposure switch 48 to begin capturing radiographic images of the subject 50. At this time, the counter 380 updates the count by incrementing the count by +1.

When the operator 38 turns on the exposure switch 48 in step S16, then in step S17, the electric power supply limiter 338 outputs a supply limit signal to the electric power controller 334 during the aforementioned period. During the period in which the electric power controller 334 is supplied with the supply limit signal, the electric power controller 334 temporarily interrupts the operation thereof to supply electric power.

In step S18, the electric power controller 334 determines whether or not electric power needs to be re-supplied, based on whether the electric power supply controller 374 of any device has output an imaging disabled signal. More specifically, if the remaining level of electric power stored in the battery 308 of the radiation source device 18 or the cassette 12 is insufficient to capture a single radiographic image, then the electric power supply controller 374 outputs an imaging disabled signal, including the remaining level of electric power and the ID of the aforesaid device to the re-supply instructing unit 382, for thereby requesting the re-supply instructing unit 382 to re-supply electric power.

If the electric power controller 334 judges that electric power needs to be re-supplied, then control proceeds to step S19, in which the image capture interruption instructing unit 378 outputs a message indicating interruption of image capturing to the mobile terminal 42. The mobile terminal 42 displays a message on a display screen thereof, and preferably outputs an alarm sound, for prompting the operator 38 to interrupt the image capturing process.

Thereafter, in step S20, the re-supply instructing unit 382 outputs a re-supply instruction signal to the electric power supply route setting unit 370, as well as to the amount-of-supplied-electric-power setting unit 372.

In step S21, the electric power supply route setting unit 370 sets a route for re-supplying electric power (re-supply route) based on the battery charging conditions, and based on the set re-supply route, outputs a supply source instruction signal or a supply destination instruction signal to the electric power supply controller 374 of each device.

In step S22, the amount-of-supplied-electric-power setting unit 372 sets an amount of electric power to be re-supplied (amount of re-supplied electric power) based on a condition concerning the supplied amount, from among the battery charging conditions, and outputs information concerning the set amount of re-supplied electric power to the electric power supply controller 374 of the corresponding device.

In step S23, if the electric power supply controller 374 is supplied with a supply source instruction signal, then the electric power supply controller 374 controls the battery 308 in order to output electric power. Further, if the electric power supply controller 374 is supplied with a supply destination instruction signal, then the electric power supply controller 374 controls the battery 308 so as to be supplied with electric power. When supply of electric power to the battery 308, or supply of electric power from the battery 308 is completed, the electric power supply controller 374 outputs a supply termination signal.

In step S24, the electric power supply completion output unit 388 outputs an electric power supply completion signal, based on supply termination signals that are input from the electric power supply controllers 374 of all of the devices to which electric power is re-supplied.

In step S25, the image capture permission instructing unit 384 outputs a message representing permission to capture an image to the mobile terminal 42, based on the electric power supply completion signal input from the electric power supply completion output unit 388. Thereafter, control returns to step S16 shown in FIG. 24 and steps subsequent thereto.

If the electric power controller 334 judges that no electric power needs to be re-supplied in step S18, then control proceeds to step S26, in which the image capture completion determiner 386 determines whether or not the image capturing process is completed, by comparing the number of times that radiographic images have been captured in the image capturing conditions with the count from the counter 380. If the count is smaller than the number of times that radiographic images have been captured, then control returns to step S16 shown in FIG. 24, and step S16 and steps subsequent thereto are repeated until the image capturing process is brought to an end. If the image capturing process is completed, control proceeds to step S27, in which the electric power controller 334 is temporarily shut down. More specifically, the image capture completion determiner 386 outputs an image capture completion signal. Based on the image capture completion signal input from the image capture completion determiner 386, the pause processor 340 outputs a pause signal to the electric power controller 334. Based on the pause signal input from the pause processor 340, the electric power controller 334 stops controlling supply of electric power, and waits to be activated at a subsequent time by the electric power supply activator 336.

In step S28, the activator/deactivator 332 performs a determining process. More specifically, if the activator/deactivator 332 is the first activator/deactivator 332A, then the first activator/deactivator 332A determines whether or not the first present position is outside of the medical organization. If the first present position remains outside of the medical organization, then control returns to step S4 shown in FIG. 23, and step S4 and steps subsequent thereto are repeated. If the operator 38 carries the first radiographic image capturing apparatus 10A, the devices of which are coupled together, into the medical organization while gripping the grip 24, then control proceeds to step S29 shown in FIG. 24, in which the electric power supply activator 336 is fully deactivated. More specifically, when the first radiographic image capturing apparatus 10A is carried into the medical organization, the first activator/deactivator 332A outputs a full deactivation signal. Based on the full deactivation signal, the electric power supply activator 336 is shut down, and the electric power supply activator 336 waits to be reactivated at a subsequent time by the first activator/deactivator 332A. At this stage, the operation sequence of the first radiographic image capturing apparatus 10A is brought to an end. However, when the first radiographic image capturing apparatus 10A is carried out of the medical organization again, step S2 shown in FIG. 23 and steps subsequent thereto are repeated.

If the activator/deactivator 332 is the second activator/deactivator 332B, then in step S28, the second activator/deactivator 332B determines whether or not the second present position remains within the preset location. If the second present position remains in the preset location, then control returns to step S4 shown in FIG. 23, and step S4 and steps subsequent thereto are repeated. If the operator 38 carries the first radiographic image capturing apparatus 10A, devices of which are coupled together, out of the preset location while gripping the grip 24, then control proceeds to step S29 shown in FIG. 24, in which the electric power supply activator 336 is fully deactivated. More specifically, when the first radiographic image capturing apparatus 10A is carried outside of the preset location, the second activator/deactivator 332B outputs a full deactivation signal. Based on the full deactivation signal, the electric power supply activator 336 is shut down, and the electric power supply activator 336 waits to be activated at a subsequent time by the second activator/deactivator 332B. At this stage, the operation sequence of the first radiographic image capturing apparatus 10A is brought to an end. However, when the first radiographic image capturing apparatus 10A is carried again into the preset location, or is carried into a new preset location, step S2 shown in FIG. 23 and steps subsequent thereto are repeated.

If the activator/deactivator 332 is the third activator/deactivator 332C, then in step S28, the third activator/deactivator 332C determines whether or not the distance between the aforesaid device and another device satisfies the certain condition. If the distance between the aforesaid device and another device still satisfies the certain condition, then control returns to step S4 shown in FIG. 23, and step S4 and steps subsequent thereto are repeated. If the operator 38 separates the radiation source device 18 and the cassette 12 of the first radiographic image capturing apparatus 10A from each other, whereupon the linear distance between the devices exceeds the reference distance, or the distance between the devices falls outside of the communication range, or if the distance between the devices is too large for the devices to be connected in a wired or wireless fashion, then control proceeds to step S29 shown in FIG. 24, in which the electric power supply activator 336 is fully deactivated. The third activator/deactivator 332C outputs a full deactivation signal. Based on the full deactivation signal, the electric power supply activator 336 is shut down and waits to be activated at a subsequent time by the third activator/deactivator 332C. At this stage, the operation sequence of the first radiographic image capturing apparatus 10A is brought to an end. However, when the distance between the aforesaid device and another device once again satisfies the certain condition, step S2 shown in FIG. 23 and steps subsequent thereto are repeated.

An operation sequence of the first radiographic image capturing apparatus 10A, if the supply timing conditions indicate supply of electric power before capturing of radiographic images, will be described below with reference to the flowcharts shown in FIGS. 25 through 27. Although the electric power manager 390 mainly is involved in the operation sequence to be described below, the cassette selector 364 and the integrated supply 368 may also be included in the operation sequence.

Figure 25:
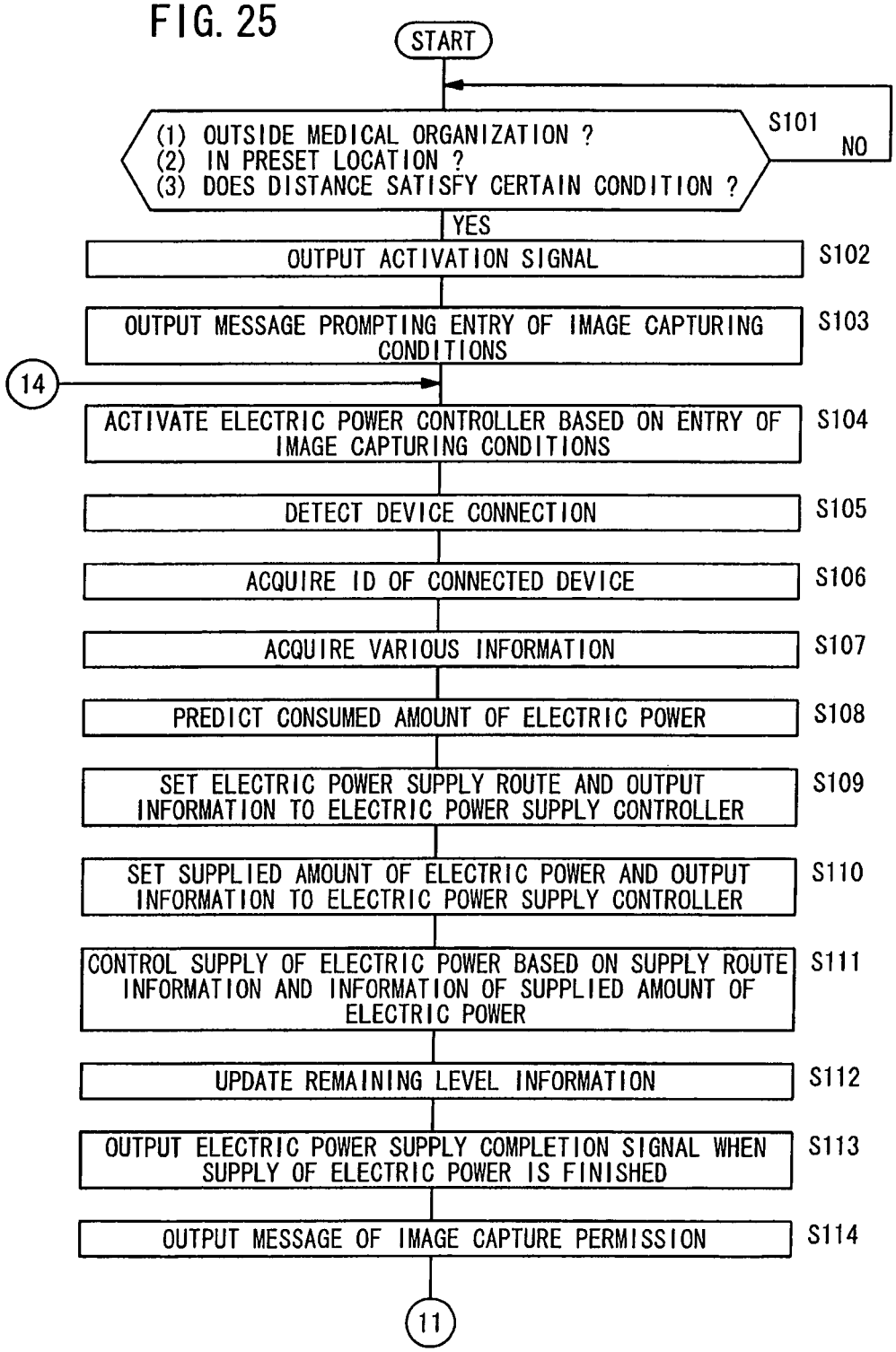
FIG. 25 is a first flowchart of an operation sequence of the first radiographic image capturing apparatus, operated under supply timing conditions for supplying electric power before capturing of radiographic images.

In step S101 shown in FIG. 25, the activator/deactivator 332 performs a determining process. More specifically, if the activator/deactivator 332 is the first activator/deactivator 332A (see FIGS. 15A and 15B), then the first activator/deactivator 332A determines whether or not the first present position is outside of a medical organization. If the operator 38 carries the first radiographic image capturing apparatus 10A, the devices of which are coupled together, out of the medical organization while gripping the grip 24, then control proceeds to step S102, in which the first activator/deactivator 332A outputs an activation signal.

If the activator/deactivator 332 is the second activator/deactivator 332B, then the second activator/deactivator 332B determines whether or not the second present position is in a preset location, i.e., a location indicated by area information registered in the second location information table 331B. If the operator 38 carries the first radiographic image capturing apparatus 10A, the devices of which are coupled together, into the preset location while gripping the grip 24, then control proceeds to step S102, in which the second activator/deactivator 332B outputs an activation signal.

If the activator/deactivator 332 is the third activator/deactivator 332C, then the third activator/deactivator 332C determines whether or not the distance between the aforesaid device and another device satisfies a certain condition. This determining process is the same as the determining process described above in step S1, and will not be described below. When the operator 38 approaches the radiation source device 18 and the cassette 12 of the first radiographic image capturing apparatus 10A toward each other until the linear distance between the devices is equal to or less than the reference distance, or when the distance between the devices enters within a communication range, or when the distance between the devices allows them to be connected in a wired or wireless fashion, the third activator/deactivator 332C outputs an activation signal in step S102.

Thereafter, in step S103, the electric power supply permission instructing unit 350 outputs a message to the mobile terminal 42 for prompting the operator 38 to enter image capturing conditions.

In step S104, the electric power supply activator 336 activates the electric power controller 334 based on the present image capturing conditions (order) entered from the mobile terminal 42. At this time, only the electric power supply activator 336 of a device having an ID, which is the same as the ID of the radiation source device 18 or the cassette 12 used to capture radiation images, which has been registered in advance in the image capturing conditions, activates the corresponding electric power controller 334. The present image capturing conditions may be input from the data center via the network and the mobile terminal 42. The present image capturing conditions are stored in the memory 330.

In step S105, the device connection detector 360 detects whether or not the device, i.e., the radiation source device 18 or the cassette 12, is connected to the first energy input/output unit 300 or the second energy input/output unit 302. If the activator/deactivator 332 is the third activator/deactivator 332C (see FIG. 17C) according to the third mode, then since the device connection detector 360 has already detected the connection in step S101, control proceeds from step S104 to step S106, while skipping step S105.

After the device connection detector 360 has detected the connection in step S105, control proceeds to step S106, in which the ID acquirer 410 of the electric power manager 390 shown in FIG. 22 acquires the ID of the connected device. More specifically, the ID acquirer 410 sends a transfer request requesting the connected device to transfer the ID thereof. The connected device outputs the ID to the electric power manager 390, and the ID acquirer 410 acquires the ID and stores the ID in the memory 330.

In step S107, the information acquirer 412 for acquiring various information acquires the present image capturing conditions, which already have been stored in the memory 330, a remaining level-of-electric-energy information table corresponding to the ID, previous image capturing conditions corresponding to the ID, and a usage history table corresponding to the ID, and stores such information in the memory 330.

In step S108, the amount-of-consumed-electric-power predictor 414 calculates amounts of electric power to be consumed by the radiation source device 18 and the cassette 12 that is used to capture radiographic images, from conditions concerning the amount of electric power to be supplied (stored in the memory 330), and the present or previous image capturing conditions, which represent the number of radiographic images to be captured, mAs values, etc., from among the battery charging conditions. The amount-of-consumed-electric-power predictor 414 then corrects the calculated amounts of electric power by multiplying the calculated amounts by usage histories of the radiation source device 18 and the cassette 12, i.e., by coefficients corresponding to the number of times that the radiation source device 18 and the cassette 12 have been used, thereby predicting amounts of electric power that are consumed by the radiation source device 18 and the cassette 12 during the present image capturing process, or amounts of electric power consumed by the radiation source device 18 and the cassette 12 during the previous image capturing process. The condition concerning amount of electric power from among the battery charging conditions may be an amount of electric power required to capture radiographic images in the present image capturing process, an amount of electric power required to capture a single radiographic image, or an amount of electric power consumed during the previous image capturing process. If the condition concerning the amount of electric power is an amount of electric power required to capture radiographic images during the present image capturing process, then the amount-of-consumed-electric-power predictor 414 calculates amounts of electric power that are consumed by the radiation source device 18 and the cassette 12 used to capture radiographic images in the present image capturing process, and corrects the calculated amounts of electric power by multiplying the calculated amounts by usage histories of the radiation source device 18 and the cassette 12, i.e., by coefficients corresponding to the number of times that the radiation source device 18 and the cassette 12 have been used, thereby predicting amounts of electric power that are consumed by the radiation source device 18 and the cassette 12 during the present image capturing process, or amounts of electric power consumed by the radiation source device 18 and the cassette 12 during the previous image capturing process. If the condition concerning amount of electric power is an amount of electric power consumed during the previous image capturing process, then the amount-of-consumed-electric-power predictor 414 calculates amounts of electric power consumed by the radiation source device 18 and the cassette 12 in the previous image capturing process, and corrects the calculated amounts of electric power by multiplying the calculated amounts by usage histories of the radiation source device 18 and the cassette 12, i.e., by coefficients corresponding to the number of times that the radiation source device 18 and the cassette 12 have been used, thereby predicting amounts of electric power consumed by the radiation source device 18 and the cassette 12 during the previous image capturing process.

In step S109, the electric power supply route setting unit 370 sets a route for supply of electric power based on the predicted amounts of electric power, and the remaining levels of electric power in the batteries 308 of the radiation source device 18 and the cassette 12 (remaining level-of-electric-energy information tables). Typically, the electric power supply route setting unit 370 sets a route for supply of electric power to a device, the battery of which stores a remaining level of electric power that will be almost eliminated during the present image capturing process. Information concerning the set route is displayed on the display screen of the mobile terminal 42. If the operator 38 intends to supply electric power additionally from other devices, i.e., a radiation source device 18 and a cassette 12 that are not used to capture radiographic images, then the operator 38 enters routes for supplying electric power from such other devices, i.e., routes for supplying electric power from the other devices to the devices having IDs, together with amounts of electric power. If the operator 38 intends to charge a battery as well using another device, i.e., a radiation source device 18 or a cassette 12, then the operator 38 enters a route for supplying electric power to or from the other device, i.e., a route from the other device to the radiation source device 18 or the cassette 12 that is used to capture radiographic images, or a route from the radiation source device 18 or the cassette 12 that is used to capture radiographic images to the other device, together with an amount of electric power to be supplied and the order in which electric power is supplied. Based on the entered route for supplying electric power, the electric power supply route setting unit 370 outputs a supply source instruction signal or a supply destination instruction signal to the electric power supply controller 374 of each of such devices.

In step S110, the amount-of-supplied-electric-power setting unit 372 sets an amount of electric power to be supplied (supplied amount of electric power) based on the predicted amount of electric power and the remaining levels of electric power in the batteries 308 of the radiation source device 18 and the cassette 12 (remaining level-of-electric-energy information tables). Thus, at most, the predicted amount of electric power is supplied to a device, the battery of which stores a remaining level of electric power that will be almost eliminated during the present image capturing process. The amount of electric power, which is supplied to such a device, may be one-half or one-third the predicted amount of electric power. The information of the set amount of electric power is displayed on a display screen of the mobile terminal 42. The set amount of electric power also can be changed as desired by the mobile terminal 42. If the operator 38 intends to charge a battery as well, then the amount-of-supplied-electric-power setting unit 372 also sets an amount of electric power to be supplied additionally to charge the battery. The amount of electric power, which is predicted based on the previous image capturing conditions, is supplied in order to supplement the amount of electric power consumed during the previous image capturing process. If the operator 38 intends to charge a battery as well, then the amount-of-supplied-electric-power setting unit 372 also sets an amount of electric power to be supplied additionally to charge the battery. The set amount of electric power is supplied to the electric power supply controller 374 of the corresponding device.

In step S111, if the electric power supply controller 374 is supplied with a supply source instruction signal, then the electric power supply controller 374 controls the battery 308 to output electric power. If the electric power supply controller 374 is supplied with a supply destination instruction signal, then the electric power supply controller 374 controls the battery 308 so as to be supplied with electric power. When supply of electric power to the battery 308 or supply of electric power from the battery 308 is completed, the electric power supply controller 374 outputs a supply termination signal.

In step S112, the information updater 416 of the electric power manager 390, in the remaining level-of-electric-energy information table, subtracts the amount of supplied electric power from the remaining level of electric power of the device that serves as the electric power supply source, and adds the amount of supplied electric power to the remaining level of electric power of the device that serves as the electric power supply destination.

In step S113, the electric power supply completion output unit 388 outputs an electric power supply completion signal based on supply termination signals input from the electric power supply controllers 374 of all of the devices to which electric power has been supplied.

In step S114, the image capture permission instructing unit 384 outputs a message, which represents permission to capture an image, to the mobile terminal 42 based on the electric power supply completion signal input from the electric power supply completion output unit 388.

Figure 26:
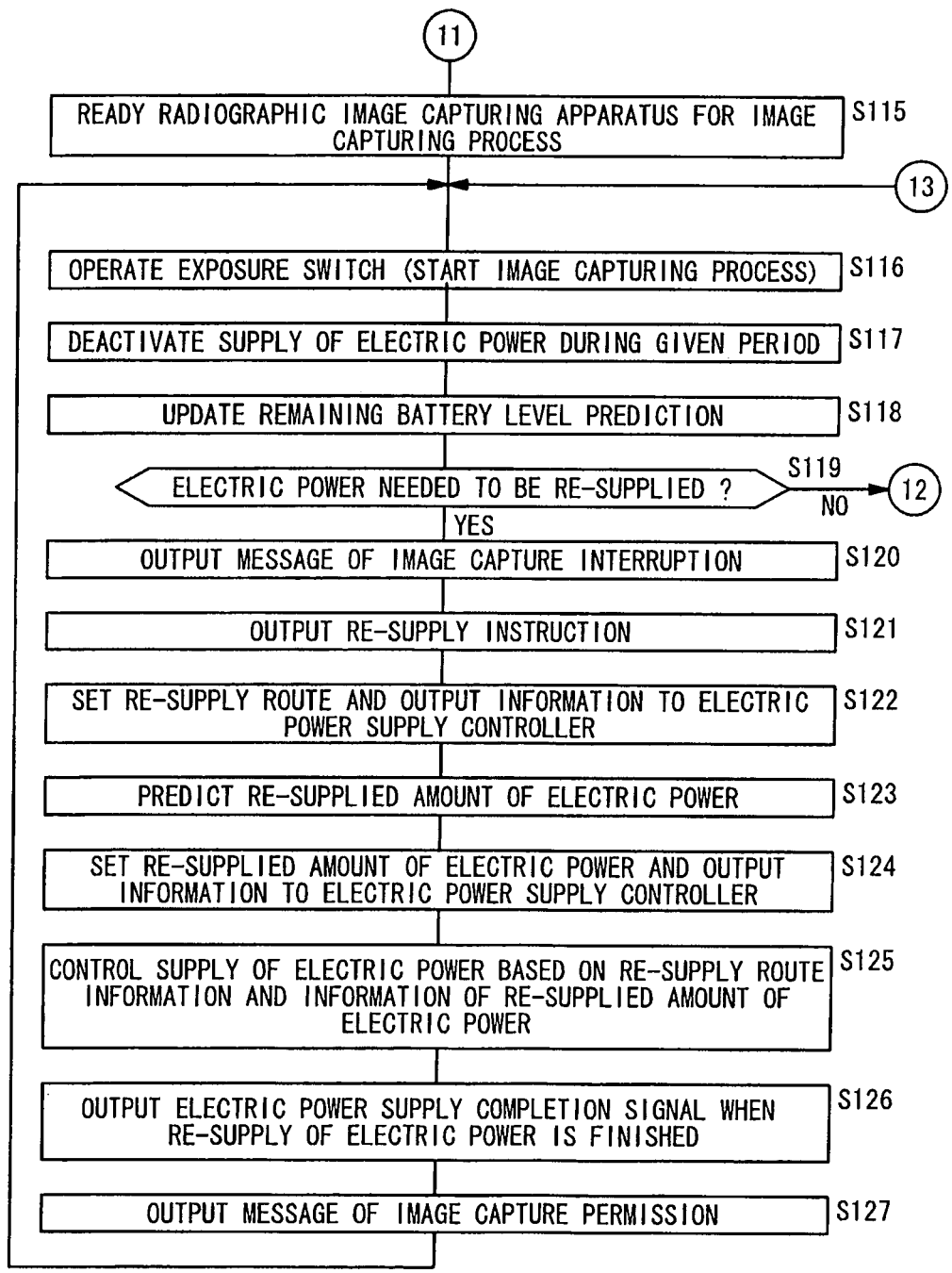
FIG. 26 is a second flowchart of an operation sequence of the first radiographic image capturing apparatus, operated under supply timing conditions for supplying electric power before capturing of radiographic images.

In step S115 shown in FIG. 26, the operator 38 prepares the first radiographic image capturing apparatus 10A for capturing radiographic images, at a site to which the first radiographic image capturing apparatus 10A has been carried. This preparatory procedure has already been described in detail above, and will not be described below.

In step S116, the operator 38 turns on the exposure switch 48 in order to start capturing radiographic images of the subject 50. At this time, the counter 380 updates the count thereof by incrementing the count by +1.

When the operator 38 turns on the exposure switch 48 in step S116, the electric power supply limiter 338 outputs a supply limit signal to the electric power controller 334, during the period referred to above in step S117. During the period in which the electric power controller 334 is supplied with the supply limit signal, the electric power supply operation of the electric power controller 334 is limited.

In step S118, the remaining level prediction updater 392 updates, by way of subtraction, the remaining levels of electric power stored in the batteries, which are recorded in the remaining level-of-electric-energy information tables, i.e., the remaining levels of electric power stored in the batteries 308 of the radiation source device 18 and the cassette 12, which are utilized for capturing radiographic images. More specifically, with respect to the radiation source device 18 and the cassette 12 that carry out capturing of radiographic images, the remaining level prediction updater 392 calculates the amounts of electric power consumed during each time the exposure switch 48 is turned on, based on the image capturing conditions and the usage history tables, and subtracts the calculated amounts of electric power from the remaining levels of electric power stored in the batteries 308 of the radiation source device 18 and the cassette 12, which are recorded in the remaining level-of-electric-energy information tables.

In step S119, the electric power controller 334 determines whether or not electric power needs to be re-supplied, based on whether the electric power supply controller 374 of any device has output an imaging disabled signal.

If the electric power controller 334 judges that electric power needs to be re-supplied, then control proceeds to step S120, in which the image capture interruption instructing unit 378 outputs a message indicative of an image capture interruption to the mobile terminal 42. The mobile terminal 42 displays the message on a display screen thereof, and preferably outputs an alarm sound, for prompting the operator 38 to interrupt the image capturing process.

Thereafter, in step S121, the re-supply instructing unit 382 outputs a re-supply instruction signal to the electric power supply route setting unit 370, the amount-of-supplied-electric-power setting unit 372, and the electric power manager 390.

In step S122, the electric power supply route setting unit 370 sets, as a re-supply route, a route for supplying electric power to the device having the ID included in the input re-supply instruction signal, and outputs a supply source instruction signal or a supply destination instruction signal to the electric power supply controller 374 of each device, based on the set re-supply route.

In step S123, the amount-of-consumed-electric-power predictor 414 calculates amounts of electric power to be consumed by the device having the aforementioned ID, i.e., the radiation source device 18 or the cassette 12 that is re-supplied with electric power, from among the image capturing conditions for an image capturing process to be carried out, and from which image capturing conditions for radiographic images already captured (indicated by the count) are excluded, among the battery charging conditions stored in the memory 330 and the present image capturing conditions representative of the number of radiographic images to be captured, mAs values, etc. The amount-of-consumed-electric-power predictor 414 also corrects the calculated amounts of electric power by multiplying the calculated amounts by the usage history of the device having the ID, i.e., a coefficient corresponding to the number of times that the device of the ID has been used, thereby predicting an amount of electric power that will be consumed by the device of the ID in the image capturing process to be carried out.

In step S124, the amount-of-supplied-electric-power setting unit 372 sets the amount of electric power predicted by the amount-of-consumed-electric-power predictor 414, as an amount of re-supplied electric power, and supplies information concerning the set amount of re-supplied electric power to the electric power supply controller 374 of the corresponding device.

In step S125, if the electric power supply controller 374 is supplied with a supply source instruction signal, then the electric power supply controller 374 controls the battery 308 to output electric power. If the electric power supply controller 374 is supplied with a supply destination instruction signal, then the electric power supply controller 374 controls the battery 308 so as to be supplied with electric power. When supply of electric power to the battery 308 or supply of electric power from the battery 308 is completed, the electric power supply controller 374 outputs a supply termination signal.

In step S126, the electric power supply completion output unit 388 outputs an electric power supply completion signal, based on supply termination signals input from the electric power supply controllers 374 of all of the devices to which electric power has been re-supplied.

In step S127, the image capture permission instructing unit 384 outputs a message to the mobile terminal 42 representing permission to capture images, based on the electric power supply completion signal input from the electric power supply completion output unit 388. Thereafter, control returns to step S116 and steps subsequent thereto.

Figure 27:
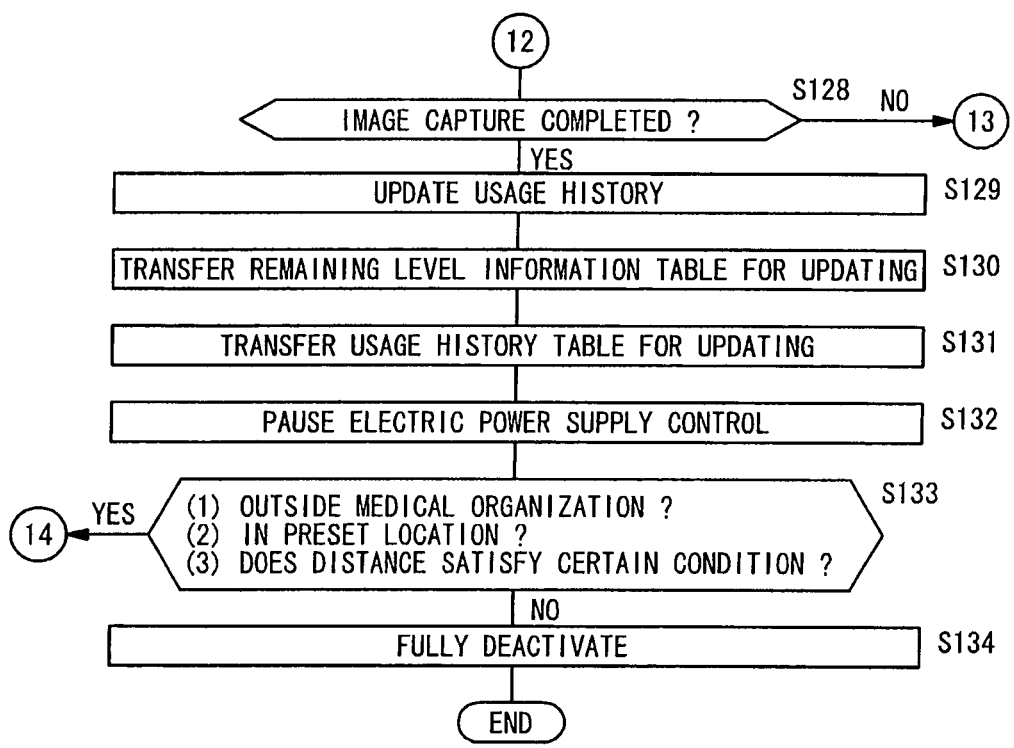
FIG. 27 is a third flowchart of an operation sequence of the first radiographic image capturing apparatus, operated under supply timing conditions for supplying electric power before capturing of radiographic images.

If the electric power controller 334 judges that no electric power needs to be re-supplied in step S119, then control proceeds to step S128 shown in FIG. 27, in which the image capture completion determiner 386 determines whether or not the image capturing process is completed by comparing the number of times that radiographic images have been captured in the image capturing conditions with the count of the counter 380. If the count is smaller than the number of times that radiographic images have been captured, then control returns to step S116 shown in FIG. 26, and step S116 and steps subsequent thereto are repeated until the image capturing process is brought to an end. If the image capturing process is completed, control proceeds to step S129 shown in FIG. 27, in which the usage history updater 394 adds the number of times that the exposure switch 48 has been turned on to the number of times recorded in the usage history table, i.e., the number of times that the radiation source device 18 and the cassette 12 have been used to capture radiographic images.

In step S130, the remaining level information transfer unit 396 transfers the remaining level information table via the network to the database of the data center for updating.

In step S131, the usage history transfer unit 398 transfers the usage history table via the network to the database of the data center for updating.

In step S132, the electric power controller 334 is temporarily shut down. More specifically, the image capture completion determiner 386 outputs an image capture completion signal. Based on the image capture completion signal input from the image capture completion determiner 386, the pause processor 340 outputs a pause signal to the electric power controller 334. Based on the pause signal input from the pause processor 340, the electric power controller 334 stops controlling supply of electric power, and waits to be activated at a subsequent time by the electric power supply activator 336.

In step S133, the activator/deactivator 332 performs a determining process. More specifically, if the activator/deactivator 332 is the first activator/deactivator 332A, then the first activator/deactivator 332A determines whether or not the first present position is outside of the medical organization. If the first present position remains outside of the medical organization, then control returns to step S104 shown in FIG. 25, and step S104 and steps subsequent thereto are repeated. If the operator 38 carries the first radiographic image capturing apparatus 10A, the devices of which are coupled together, into the medical organization while gripping the grip 24, then control proceeds to step S134 shown in FIG. 27, in which the electric power supply activator 336 is fully deactivated. More specifically, when the first radiographic image capturing apparatus 10A is carried into the medical organization, the first activator/deactivator 332A outputs a full deactivation signal. Based on the full deactivation signal, the electric power supply activator 336 is shut down and waits to be activated at a subsequent time by the first activator/deactivator 332A. At this stage, the operation sequence of the first radiographic image capturing apparatus 10A is brought to an end. However, when the first radiographic image capturing apparatus 10A is carried outside of the medical organization again, then step S102 shown in FIG. 25 and steps subsequent thereto are repeated.

If the activator/deactivator 332 is the second activator/deactivator 332B, then in step S133, the second activator/deactivator 332B determines whether or not the second present position is in the preset location. If the second present position remains in the preset location, then control returns step S104 shown in FIG. 25, and step S104 and steps subsequent thereto are repeated. If the operator 38 carries the first radiographic image capturing apparatus 10A, the devices of which are coupled together, outside of the preset location while gripping the grip 24, then control proceeds to step S134 shown in FIG. 27, in which the electric power supply activator 336 is fully deactivated. More specifically, when the first radiographic image capturing apparatus 10A is carried outside of the preset location, the second activator/deactivator 332B outputs a full deactivation signal. Based on the full deactivation signal, the electric power supply activator 336 is shut down and waits to be activated at a subsequent time by the second activator/deactivator 332B. At this stage, the operation sequence of the first radiographic image capturing apparatus 10A is brought to an end. However, when the first radiographic image capturing apparatus 10A is carried into the preset location again, or into a new preset location, step S102 shown in FIG. 25 and steps subsequent thereto are repeated.

If the activator/deactivator 332 is the third activator/deactivator 332C, then in step S133, the third activator/deactivator 332C determines whether or not the distance between the aforesaid device and another device satisfies the certain condition. If the distance between the aforesaid device and another device still satisfies the certain condition, then control returns to step S104 shown in FIG. 25, and step S104 and steps subsequent thereto are repeated. If the operator 38 separates the radiation source device 18 and the cassette 12 of the first radiographic image capturing apparatus 10A from each other, whereby the linear distance between the devices exceeds the reference distance, if the distance between the devices falls outside of the communication range, or if the distance between the devices is too large for the devices to be connected in a wired or wireless fashion, then control proceeds to step S134 shown in FIG. 27, in which the electric power supply activator 336 is fully deactivated. More specifically, the third activator/deactivator 332C outputs a full deactivation signal. Based on the full deactivation signal, the electric power supply activator 336 is shut down and waits to be activated at a subsequent time by the third activator/deactivator 332C. At this stage, the operation sequence of the first radiographic image capturing apparatus 10A is brought to an end. However, when the distance between the aforesaid device and another device again satisfies the certain condition, step S102 shown in FIG. 25 and steps subsequent thereto are repeated.

An operation sequence of the first radiographic image capturing apparatus 10A, if the supply timing conditions indicate supply of electric power after capturing of radiographic images, will be described below with reference to the flowcharts shown in FIGS. 28 and 29. Although the electric power manager 390 mainly is involved in the operation sequence to be described below, the cassette selector 364 and the integrated supply 368 may also be included in the operation sequence.

Figure 28:
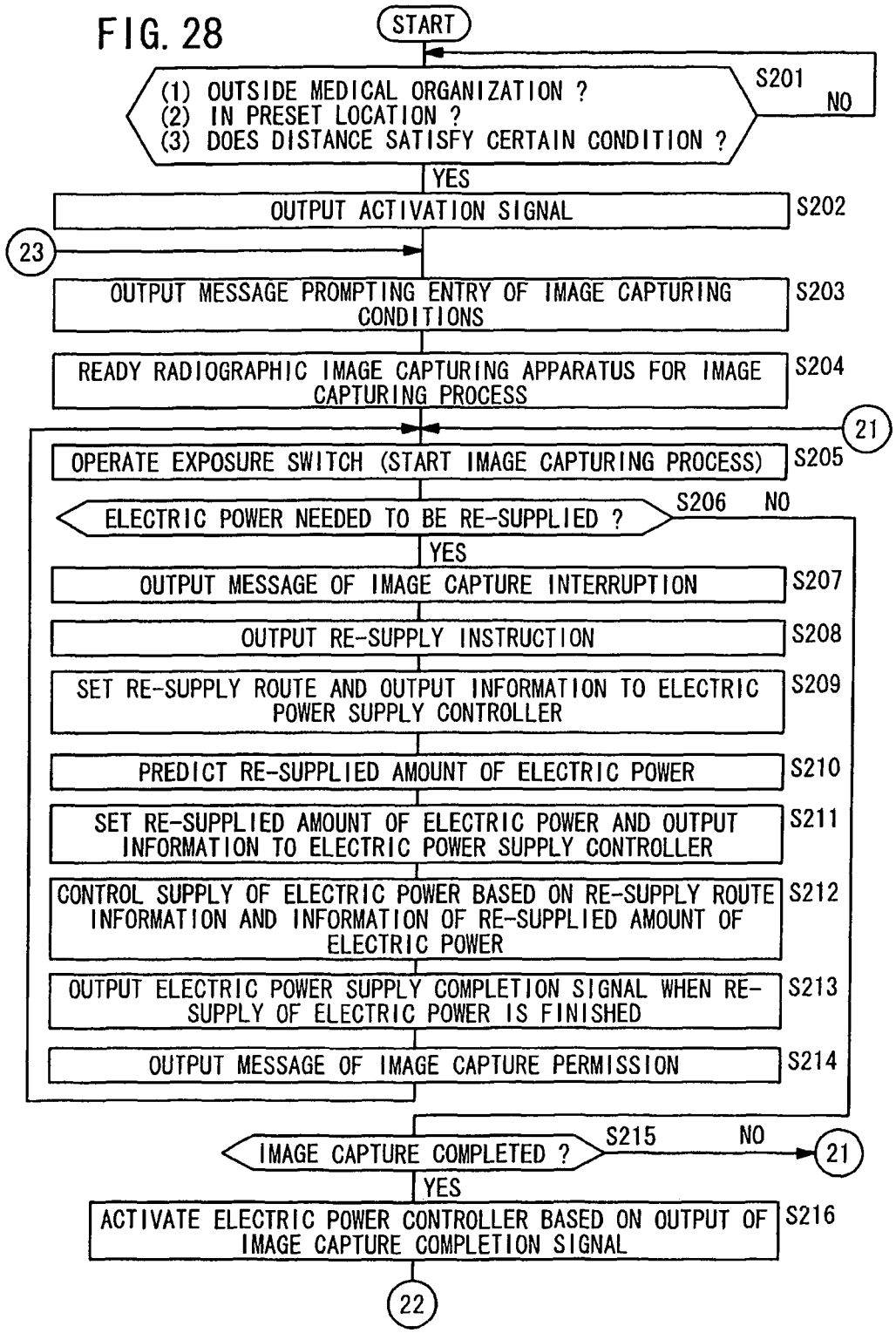
FIG. 28 is a first flowchart of an operation sequence of the first radiographic image capturing apparatus, operated under supply timing conditions for supplying electric power after capturing of radiographic images.

In step S201 shown in FIG. 28, the activator/deactivator 332 performs a determining process. More specifically, if the activator/deactivator 332 is the first activator/deactivator 332A, then the first activator/deactivator 332A determines whether or not the first present position is outside of a medical organization. If the operator 38 carries the first radiographic image capturing apparatus 10A, the devices of which are coupled together, outside of the medical organization while gripping the grip 24, then control proceeds to step S202, in which the first activator/deactivator 332A outputs an activation signal.

If the activator/deactivator 332 is the second activator/deactivator 332B, then the second activator/deactivator 332B determines whether or not the second present position is in a preset location, i.e., at a location indicated by area information registered in the second location information table 331B. If the operator 38 carries the first radiographic image capturing apparatus 10A, the devices of which are coupled together, into the preset location while gripping the grip 24, then control proceeds to step S202, in which the second activator/deactivator 332B outputs an activation signal.

If the activator/deactivator 332 is the third activator/deactivator 332C, then the third activator/deactivator 332C determines whether or not the distance between the aforesaid device and another device satisfies a certain condition. The determining process is the same as the determining process described above in step S1, and will not be described below. When the operator 38 approaches the radiation source device 18 and the cassette 12 of the first radiographic image capturing apparatus 10A toward each other until the linear distance between the devices is equal to or smaller than the reference distance, when the distance between the devices enters within the communication range, or when the distance between the devices allows them to be connected in a wired or wireless fashion, the third activator/deactivator 332C outputs an activation signal in step S202.

Thereafter, in step S203, the electric power supply permission instructing unit 350 outputs a message for prompting the operator 38 to enter image capturing conditions to the mobile terminal 42.

In step S204, the operator 38 prepares the first radiographic image capturing apparatus 10A for capturing radiographic images at a site where the first radiographic image capturing apparatus 10A has been carried. In step S205, the operator 38 turns on the exposure switch 48 to start capturing radiographic images of the subject 50.

In step S206, the electric power controller 334 determines whether or not electric power needs to be re-supplied, based on whether the electric power supply controller 374 of any given device has output an imaging disabled signal.

If the electric power controller 334 judges that electric power needs to be re-supplied, then control proceeds to step S207, in which the image capture interruption instructing unit 378 outputs a message indicating interruption of image capturing to the mobile terminal 42. Thereafter, in step S208, the re-supply instructing unit 382 outputs a re-supply instruction signal to the electric power supply route setting unit 370, the amount-of-supplied-electric-power setting unit 372, and the electric power manager 390, thereby activating the electric power supply route setting unit 370, the amount-of-supplied-electric-power setting unit 372, and the electric power manager 390 in an interrupt routine.

In step S209, the electric power supply route setting unit 370 sets a route for supplying electric power to the device having the ID included in the input re-supply instruction signal, as a re-supply route, and based on the set re-supply route, outputs a supply source instruction signal or a supply destination instruction signal to the electric power supply controller 374 of each device.

In step S210, the amount-of-consumed-electric-power predictor 414 calculates amounts of electric power that are consumed by the device having the ID, i.e., the radiation source device 18 or the cassette 12 that are re-supplied with electric power, from image capturing conditions for an image capturing process to be carried out, from which image capturing conditions for radiographic images already captured (indicated by the count) are excluded, from among the battery charging conditions stored in the memory 330, and the present image capturing conditions representative of the number of radiographic images to be captured, mAs values, etc. The amount-of-consumed-electric-power predictor 414 also corrects the calculated amounts of electric power by multiplying the calculated amounts by a usage history of the device of the ID, i.e., a coefficient corresponding to the number of times that the device of the ID has been used, thereby predicting an amount of electric power to be consumed by the device of the ID in the image capturing process to be carried out.

In step S211, the amount-of-supplied-electric-power setting unit 372 sets the amount of electric power predicted by the amount-of-consumed-electric-power predictor 414 as an amount of re-supplied electric power, and outputs the information concerning the set amount of re-supplied electric power to the electric power supply controller 374 of the corresponding device.

In step S212, if the electric power supply controller 374 is supplied with a supply source instruction signal, then the electric power supply controller 374 controls the battery 308 to output electric power. Further, if the electric power supply controller 374 is supplied with a supply destination instruction signal, then the electric power supply controller 374 controls the battery 308 so as to be supplied with electric power. When supply of electric power to the battery 308 or supply of electric power from the battery 308 is completed, then the electric power supply controller 374 outputs a supply termination signal.

In step S213, the electric power supply completion output unit 388 outputs an electric power supply completion signal based on supply termination signals, which are input from the electric power supply controllers 374 of all of the devices to which electric power has been re-supplied.

In step S214, the image capture permission instructing unit 384 outputs a message representing permission to capture an image to the mobile terminal 42, based on the electric power supply completion signal input from the electric power supply completion output unit 388. Thereafter, control returns to step S205 and steps subsequent thereto.

If the electric power controller 334 judges that no electric power needs to be re-supplied in step S206, then control proceeds to step S215, in which the image capture completion determiner 386 determines whether or not the image capturing process is completed. If the image capturing process is not completed, then control returns to step S205, and step S205 and steps subsequent thereto are repeated until the image capturing process is brought to an end. If the image capturing process has finished, control proceeds to step S216, in which the electric power supply activator 336 activates the electric power controller 334 based on an image capture completion signal input from the image capture completion determiner 386. At this time, only the electric power supply activator 336 of a device having an ID that is the same as the ID of the radiation source device 18 or the cassette 12 that is used to capture radiation images, which has been registered in advance in the image capturing conditions, activates the corresponding electric power controller 334.

Figure 29:
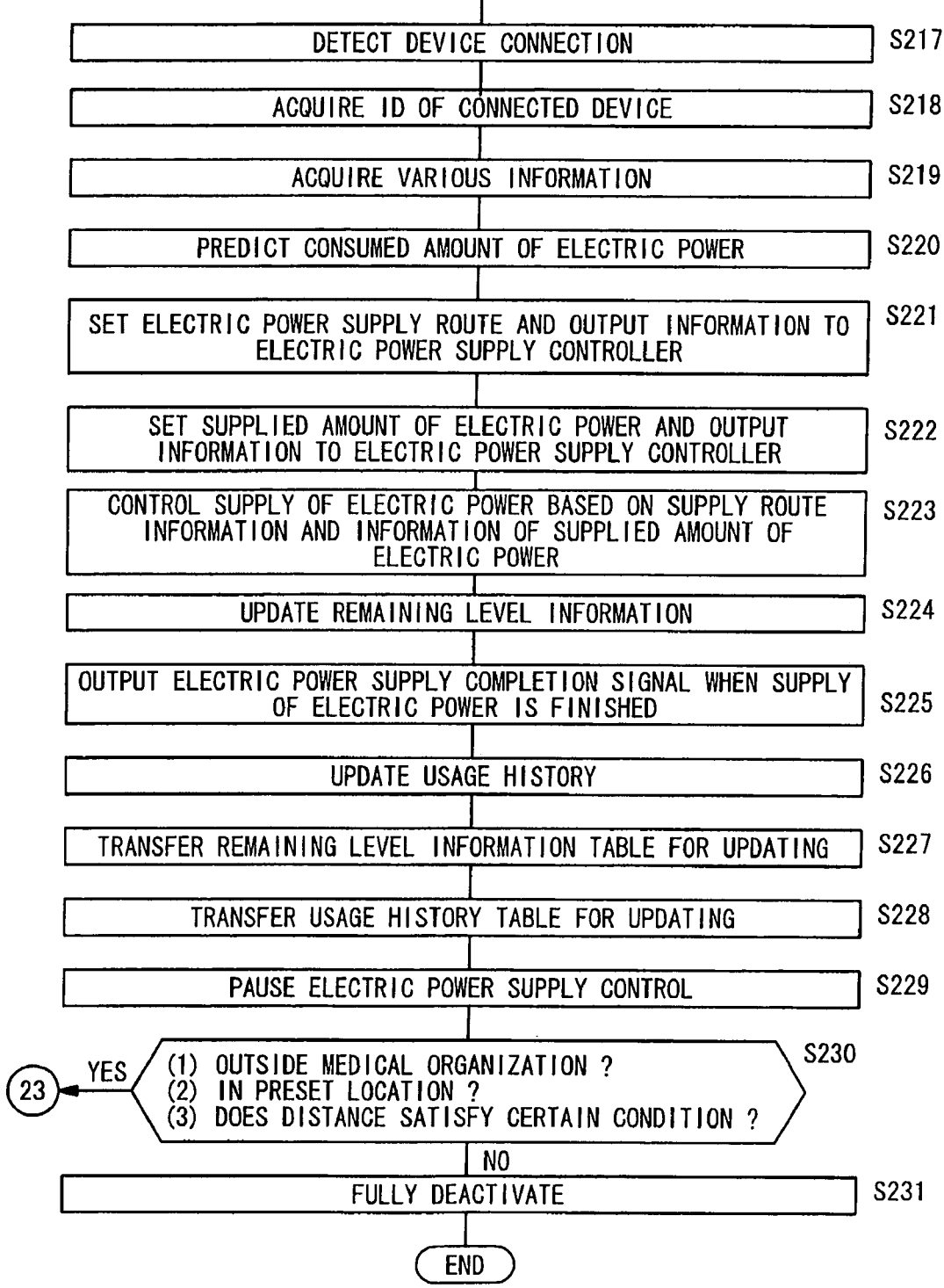
FIG. 29 is a second flowchart of an operation sequence of the first radiographic image capturing apparatus, operated under supply timing conditions for supplying electric power after capturing of radiographic images.

In step S217 shown in FIG. 29, the device connection detector 360 detects whether or not the device is connected to the first energy input/output unit 300 or the second energy input/output unit 302. If the activator/deactivator 332 is the third activator/deactivator 332C (see FIG. 17C) according to the third mode, then since the device connection detector 360 has already detected the connection in step S201, control proceeds from step S216 to step S218, while skipping step S217.

After the device connection detector 360 has detected the connection in step S217, control proceeds to step S218, in which the ID acquirer 410 of the electric power manager 390 acquires the ID of the connected device. Thereafter, in step S219, the information acquirer 412 for acquiring various information acquires the present image capturing conditions, which have already been stored in the memory 330, a remaining level-of-electric-energy information table corresponding to the ID, previous image capturing conditions corresponding to the ID, and a usage history table corresponding to the ID, and stores such information in the memory 330.

In step S220, the amount-of-consumed-electric-power predictor 414 calculates amounts of electric power to be consumed by the radiation source device 18 and the cassette 12, which are used to capture radiographic images, from a condition concerning the amount of electric power to be supplied, and the present or previous image capturing conditions representative of the number of radiographic images to be captured, mAs values, etc., from among the battery charging conditions.

In step S221, the electric power supply route setting unit 370 sets a route for supply of electric power, based on the predicted amounts of electric power and the remaining levels of electric power in the batteries 308 of the radiation source device 18 and the cassette 12 (remaining level-of-electric-energy information tables).

Thereafter, in step S222, the amount-of-supplied-electric-power setting unit 372 sets an amount of electric power to be supplied (supplied amount of electric power), based on the predicted amount of electric power, and the remaining levels of electric power in the batteries 308 of the radiation source device 18 and the cassette 12 (remaining level-of-electric-energy information tables).

In step S223, if the electric power supply controller 374 is supplied with a supply source instruction signal, then the electric power supply controller 374 controls the battery 308 to output electric power. Further, if the electric power supply controller 374 is supplied with a supply destination instruction signal, then the electric power supply controller 374 controls the battery 308 so as to be supplied with electric power. When supply of electric power to the battery 308 or supply of electric power from the battery 308 is completed, the electric power supply controller 374 outputs a supply termination signal.

In step S224, the information updater 416, in the remaining level-of-electric-energy information table, subtracts the amount of supplied electric power from the remaining level of electric power of the device that serves as an electric power supply source, and adds the amount of supplied electric power to the remaining level of electric power of the device that serves as an electric power supply destination.

In step S225, the electric power supply completion output unit 388 outputs an electric power supply completion signal, based on supply termination signals input from the electric power supply controllers 374 of all of the devices to which electric power has been supplied.

In step S226, the usage history updater 394 adds the number of times that the exposure switch 48 has been turned on to the number of times recorded in the usage history table, i.e., the number of times that the radiation source device 18 and the cassette 12 have been used to capture radiographic images.

In step S227, the remaining level information transfer unit 396 transfers the remaining level information table via the network to the database of the data center for updating. In step S228, the usage history transfer unit 398 transfers the usage history table via the network to the database of the data center for updating. Thereafter, in step S229, the pause processor 340 temporarily shuts down the electric power controller 334.

In step S230, the activator/deactivator 332 performs a determining process. More specifically, if the activator/deactivator 332 is the first activator/deactivator 332A, then the first activator/deactivator 332A determines whether or not the first present position lies outside of the medical organization. If the first present position remains outside of the medical organization, then control returns to step S203 shown in FIG. 28, and step S203 and steps subsequent thereto are repeated. If the operator 38 carries the first radiographic image capturing apparatus 10A, the devices of which are coupled together, into the medical organization while gripping the grip 24, then control proceeds to step S231 shown in FIG. 29, in which the electric power supply activator 336 is fully deactivated. More specifically, when the first radiographic image capturing apparatus 10A is carried into the medical organization, the first activator/deactivator 332A outputs a full deactivation signal. Based on the full deactivation signal, the electric power supply activator 336 is shut down and waits to be activated at a subsequent time by the first activator/deactivator 332A. At this stage, the operation sequence of the first radiographic image capturing apparatus 10A is brought to an end. However, when the first radiographic image capturing apparatus 10A again is carried outside of the medical organization, step S202 shown in FIG. 28 and steps subsequent thereto are repeated.

If the activator/deactivator 332 is the second activator/deactivator 332B, then the second activator/deactivator 332B determines whether or not the second present position is in the preset location in step S230. If the second present position remains in the preset location, then control returns to step S203 shown in FIG. 28, and step S203 and steps subsequent thereto are repeated. If the operator 38 carries the first radiographic image capturing apparatus 10A, the devices of which are coupled together, outside of the preset location while gripping the grip 24, then control proceeds to step S231 shown in FIG. 29, in which the electric power supply activator 336 is fully deactivated. More specifically, when the first radiographic image capturing apparatus 10A is carried outside of the preset location, the second activator/deactivator 332B outputs a full deactivation signal. Based on the full deactivation signal, the electric power supply activator 336 is shut down and waits to be activated at a subsequent time by the second activator/deactivator 332B. At this stage, the operation sequence of the first radiographic image capturing apparatus 10A is brought to an end. However, when the first radiographic image capturing apparatus 10A is carried again into the preset location or into a new preset location, step S202 shown in FIG. 28 and steps subsequent thereto are repeated.

If the activator/deactivator 332 is the third activator/deactivator 332C, then in step S230, the third activator/deactivator 332C determines whether or not the distance between the aforesaid device and another device satisfies the certain condition. If the distance between the aforesaid device and another device still satisfies the certain condition, then control returns to step S203 shown in FIG. 28, and step S203 and steps subsequent thereto are repeated. If the operator 38 separates the radiation source device 18 and the cassette 12 of the first radiographic image capturing apparatus 10A from each other, and the linear distance between the devices exceeds the reference distance, if the distance between the devices falls outside of the communication range, or if the distance between the devices is too large for the devices to be connected in a wired or wireless fashion, then control proceeds to step S231 shown in FIG. 29, in which the electric power supply activator 336 is fully deactivated. The third activator/deactivator 332C outputs a full deactivation signal. Based on the full deactivation signal, the electric power supply activator 336 is shut down, and the electric power supply activator 336 waits to be activated at a subsequent time by the third activator/deactivator 332C. At this stage, the operation sequence of the first radiographic image capturing apparatus 10A is brought to an end. However, when the distance between the aforesaid device and another device again satisfies the certain condition, step S202 shown in FIG. 28 and steps subsequent thereto are repeated.

Since the first radiographic image capturing apparatus 10A, which includes the first activator/deactivator 332A, is prevented from being supplied with electric power within a medical organization, the first radiographic image capturing apparatus 10A can reduce consumption of electric power.

Furthermore, since the first radiographic image capturing apparatus 10A, which includes the second activator/deactivator 332B, is prevented from being supplied with electric power in places other than the preset location, the first radiographic image capturing apparatus 10A can reduce consumption of electric power.

If a home-care service site is registered as the preset location, then the first radiographic image capturing apparatus 10A can easily capture radiographic images of examinees at their homes.

When needs arise for capturing radiographic images at accident sites, disaster sites, or medical organizations such as clinics that do not have radiation facilities, the first radiographic image capturing apparatus 10A can be carried to such a site, and the site can quickly be registered as a preset location using GPS or the like. Once the site has been registered as the preset location, the first radiographic image capturing apparatus 10A can quickly start capturing radiographic images of an examinee, such as an accident victim, a disaster victim, or a patient, without requiring the examinee to be moved to a mobile medical checkup motor vehicle or an image capturing chamber.

The first radiographic image capturing apparatus 10A, which includes the second activator/deactivator 332B, is capable of presetting a location by way of absolute positioning, and also of presetting a location by way of relative positioning. Presetting a location by way of relative positioning offers the following advantages. While the operator of the first radiographic image capturing apparatus 10A is on board a transport vehicle, the operator designates the transport vehicle as a preset location. Then, the present position of the transport vehicle is registered as area information, which is representative a relative position, in a location information table. Inasmuch as the area information varies periodically as the transport vehicle moves, the present position and the area information, which is representative of the relative position, can be compared with each other in the same manner as the present position and the area information, which is representative of the absolute position, are compared with each other, as described above. Since fixed locations such as buildings, land, etc., and also moving objects (locations) such as transport vehicles including ambulances, mobile medical checkup motor vehicles, railway cars, ships, aircrafts, etc., can be registered as preset locations, it is possible for the first radiographic image capturing apparatus 10A to quickly start capturing radiographic images of an examinee, such as an accident victim, a disaster victim, or a patient in a transport vehicle, without requiring the examinee to be moved to a hospital having a radiation facility.

Since the first radiographic image capturing apparatus 10A, which includes the third activator/deactivator 332C, is prevented from being supplied with electric power until the distance between the cassette 12 and the radiation source device 18 of the first radiographic image capturing apparatus 10A satisfies a certain condition, the first radiographic image capturing apparatus 10A can reduce consumption of electric power.

As soon as the distance between the cassette 12 and the radiation source device 18 satisfies the certain condition, the first radiographic image capturing apparatus 10A is made capable of capturing radiographic images of examinees. Consequently, the first radiographic image capturing apparatus 10A is convenient to use.

If the cassette 12 and the radiation source device 18 are separately stored and carried, then the cassette 12 and the radiation source device 18 are protected against being stolen as a set.

The first radiographic image capturing apparatus 10A, which incorporates therein any one of the first activator/deactivator 332A, the second activator/deactivator 332B, and the third activator/deactivator 332C, offers the following common advantages:

(1) The first radiographic image capturing apparatus 10A requires only the batteries 308 of the radiation source device 18 and the cassette 12 as power supplies thereof. Therefore, the first radiographic image capturing apparatus 10A is small in size and weight when carried, and is convenient to use (e.g., is portable).

(2) If the electric power controller 334 controls electric power supplied only along a route from the radiation source device 18 to the cassette 12, then a built-in capacitor may be used as the battery 308 of the cassette 12. In such a case, since a separate battery is not required as the battery 308 for the cassette 12, the user is able to carry the first radiographic image capturing apparatus 10A easily.

(3) Similarly, if the electric power controller 334 controls electric power so as to be supplied with power only along a route from the cassette 12 to the radiation source device 18, then a built-in capacitor may be used as the battery 308 of the radiation source device 18. In such a case, since a separate battery is not required as the battery 308 for the radiation source device 18, the user is able to carry the first radiographic image capturing apparatus 10A easily.

(4) When an unexpected need arises to capture radiographic images, e.g., when it is necessary to recapture radiographic images, or if an additional order comes up to capture radiographic images, while radiographic images are being captured on a medical checkup vehicle, the first radiographic image capturing apparatus 10A can meet such a need. Instead of the medical checkup vehicle, the first radiographic image capturing apparatus 10A itself may be used.

(5) For capturing radiographic images in a region where a home power supply is provided by a new form of energy, the first radiographic image capturing apparatus 10A can be used in order to minimize consumption of electric power generated from such a new form of energy.

(6) When a need arises to capture radiographic images of examinees at accident sites, disaster sites, or on transport vehicles such as ambulances (while in movement or at rest), railway cars, ships, aircrafts, or the like, the first radiographic image capturing apparatus 10A can be used quickly to start capturing radiographic images of an examinee, such as an accident victim or a disaster victim, without requiring the examinee to be moved unduly to a mobile medical checkup motor vehicle. While on a transport vehicle, the first radiographic image capturing apparatus 10A can quickly begin capturing radiographic images of the examinee, without having to wait for the transport vehicle to arrive at a station, a port, or an airport. While on an ambulance, the first radiographic image capturing apparatus 10A can send captured radiographic image information to a medical organization such as a hospital before the ambulance reaches the hospital. As a consequence, a doctor at the hospital can recognize the condition of the examinee in advance, and hence can quickly prepare the examinee for treatment.

(7) It is possible to carry several first radiographic image capturing apparatus 10A on a mobile medical checkup motor vehicle to perform periodic or temporary medical checkups at schools or large corporations where the number of examinees is large. Usually, since a single mobile medical checkup motor vehicle, which is equipped with a single ordinary radiographic image capturing apparatus, is dispatched to such locations, it has been customary for such examinees to have to wait a very long time before radiographic images of the examinees can be captured. According to the present invention, several first radiographic image capturing apparatus 10A can be used simultaneously in order to minimize the waiting time before radiographic images of examinees can be captured.

(8) Electric power can be supplied along a wired route or a wireless route. For example, electric power can be supplied along a route from a radiation source device 18 used in an image capturing process to a cassette 12 used in the image capturing process, along a route from another radiation source device 18, which is not used in an image capturing process, to the cassette 12 that is used in the image capturing process, or along a route from another cassette 12, which is not used in an image capturing process, to the cassette 12 that is used in the image capturing process.

(9) In addition, electric power can be supplied along a route from a cassette 12 used in an image capturing process to a radiation source device 18 used in the image capturing process, or along a route from another radiation source device 18, which is not used in an image capturing process, to the radiation source device 18 that is used in the image capturing process. Electric power can be supplied to a device, e.g., the radiation source device 18 or the cassette 12, in a wireless fashion, when the device enters into an area enabling wireless feeding of power thereto.

(10) If an electric power supply route is fixed to a route from the radiation source device 18 to the cassette 12, or from the cassette 12 to the radiation source device 18, then since a user is required to confirm only the level of electric power in the supply source, a preparatory process for supplying electric power can be simplified, and radiographic images can be captured quickly.

(11) If the first energy input/output unit 300 is used via a wired connection and the second energy input/output unit 302 is used via a wireless connection, then composite connections are made available for supplying electric power. For example, electric power can be supplied along a route from the radiation source device 18 to the cassette 12 and another radiation source device 18, along a route from the radiation source device 18 to the cassette 12 and another cassette 12, along a route from the cassette 12 to the radiation source device 18 and another cassette 12, or along a route from the cassette 12 to the radiation source device 18 and another radiation source device 18.

(12) The radiation source device 18 is supplied with electric power preferentially from a cassette 12 that has been deteriorated greatly, or from a cassette 12 having a small remaining built-in memory capacity. Therefore, electric power stored in a cassette 12, which has not been deteriorated greatly, or in a cassette 12 having a large remaining built-in memory capacity, can be saved, thereby enabling the first radiographic image capturing apparatus 10A to be readily available for emergencies.

(13) The radiation source device 18 is supplied with electric power preferentially from a cassette 12 that is located closer to the radiation source device 18. Therefore, the time required to supply electric power to the radiation source device 18 is shortened, thereby making the first radiographic image capturing apparatus 10A readily available for emergencies.

(14) The radiation source device 18 is supplied with electric power preferentially from a cassette 12 that is smaller in size. Therefore, electric power stored in a cassette 12, which is larger in size and hence more versatile, can be saved, thereby making the first radiographic image capturing apparatus 10A readily available for emergencies.

(15) Since the first radiographic image capturing apparatus 10A includes the electric power manager 390, the level of electric power required to capture a desired number of radiographic images is managed, so as to supply electric power from a device, the battery of which stores excessive electric power to a device having a battery with insufficient electric power, for example, up to the level of the required electric power. Therefore, the radiation source device 18 and the cassette 12 can be supplied efficiently with electric power, thereby making the first radiographic image capturing apparatus 10A readily available in an emergency. Further, since electric power required to capture radiographic images can flexibly be supplied from another device, which is not used in the image capturing process, the first radiographic image capturing apparatus 10A can be made readily available for emergencies.

(16) The timing at which electric power is supplied can be determined as desired. For example, the timing at which electric power is supplied can be determined in order to supply electric energy before an image capturing process is carried out. In this manner, electric power required to capture radiographic images can be ensured without wasteful electric power consumption. Since electric power required to capture radiographic images is predicted and supplied in accordance therewith, electric power is supplied efficiently. If the timing at which electric power is supplied is determined in order to supply electric energy after an image capturing process has been performed, then since the amount of electric power required to capture at least one radiographic image is ensured, the first radiographic image capturing apparatus 10A can quickly be readied to perform a next image capturing process.

(17) Supply of electric power is stopped during a period in which noise is likely to be added to radiographic image information being captured. Consequently, wasteful consumption of electric power is minimized for enabling low electric power consumption, while at the same time the quality of the radiographic image information is prevented from becoming degraded.

In the above embodiment, the battery controller 306 is provided in each of the devices, e.g., the radiation source device 18 and the cassette 12. However, among the components that make up the battery controller 306, the electric power supply controller 374 and the remaining level detector 376 may be provided in each of the devices, whereas the other components thereof may be provided only in the radiation source device 18 or in the cassette 12 that is used in an image capturing process, e.g., in any one of a radiation source device 18, a cassette 12, and a PC 280, which are used in an image capturing process of a third radiographic image capturing apparatus 10C, to be described later. Among the components of the electric power controller 334, only the electric power manager 390 may be provided in either one of the radiation source device 18 or the cassette 12 that is used in an image capturing process, e.g., in any one of the radiation source device 18, the cassette 12, and the PC 280, which are used in an image capturing process of the third radiographic image capturing apparatus 10C, to be described later.

While the first radiographic image capturing apparatus 10A is transported, the radiation source device 18 and the cassette 12 are coupled integrally to each other by the joining mechanism 82. While the first radiographic image capturing apparatus 10A operates to capture radiographic images, the radiation source device 18 and the cassette 12 are separated from each other, and then the radiation source 44 of the radiation source device 18 emits radiation 46 that is applied to the subject 50. Therefore, the first radiographic image capturing apparatus 10A of a portable type, which is small in size and weight, can simply and quickly be readied for capturing radiographic images.

The radiation detector 86 may comprise a light readout type of radiation detector for acquiring radiographic image information. When radiation is applied through a subject to solid-state detecting elements of the light readout type of radiation detector, the solid-state detecting elements store respective electrostatic latent images of the subject depending on the applied dose of the radiation. For reading the stored electrostatic latent images, reading light is applied to the radiation detector in order to cause the solid-state detecting elements to generate currents that depend on the stored electrostatic latent images. The generated currents are detected as representative of radiographic image information of the subject. Thereafter, erasing light is applied to the radiation detector in order to erase remaining electrostatic latent images from the solid-state detecting elements, so that the radiation detector can be reused. For details, reference should be made to Japanese Laid-Open Patent Publication No. 2000-105297.

The first radiographic image capturing apparatus 10A may comprise a water-resistant, hermetically sealed structure, thereby making the first radiographic image capturing apparatus 10A resistant to contamination by blood and bacteria. When necessary, the first radiographic image capturing apparatus 10A may be cleaned and sterilized for enabling repetitive use.

The first radiographic image capturing apparatus 10A may perform wireless communications with an external device by way of ordinary wireless communications using radio waves, or by way of optical wireless communications using infrared rays or the like.

Figure 30:
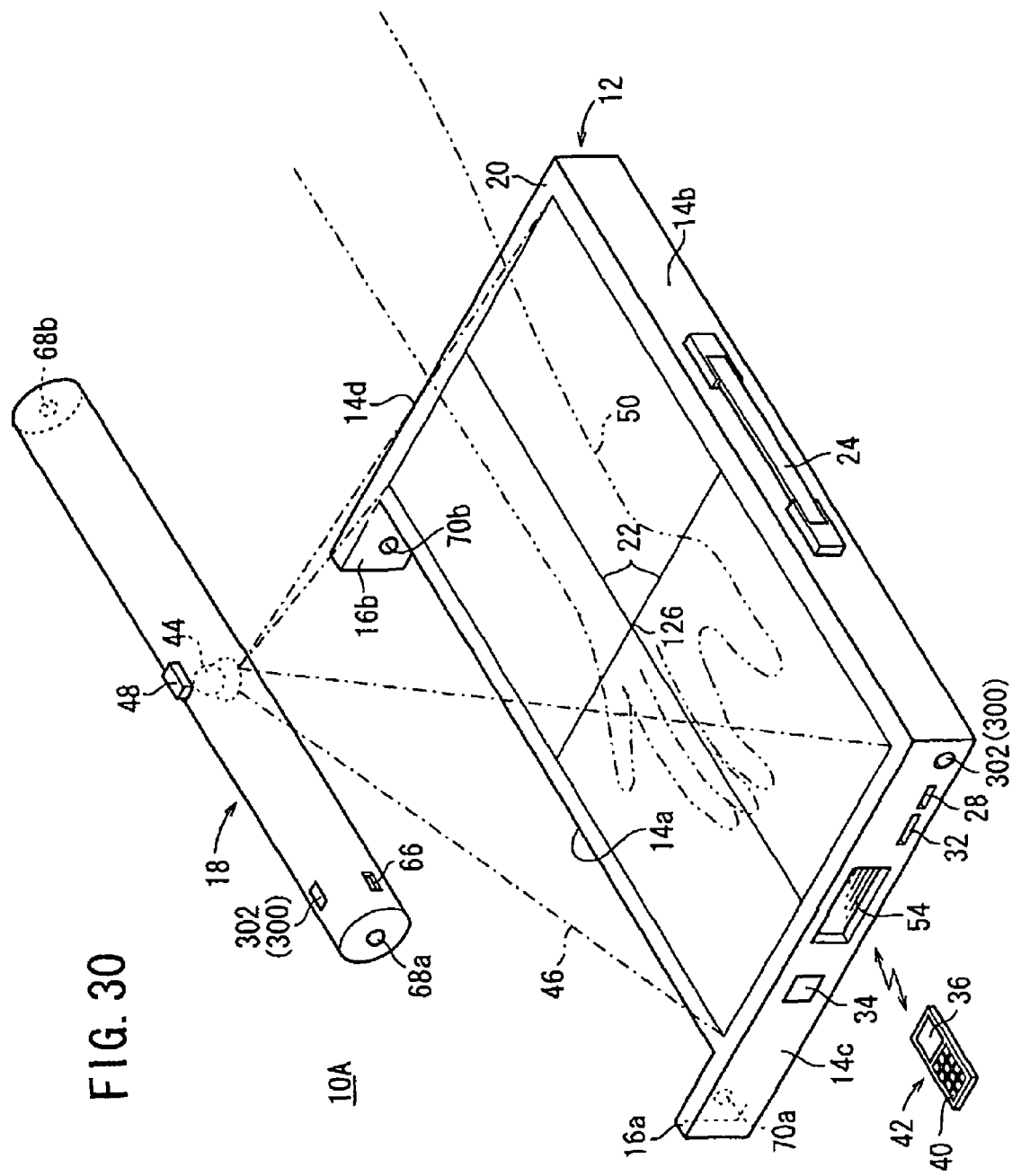
FIG. 30 is a perspective view of a modification of the first radiographic image capturing apparatus.

In the first embodiment, as shown in FIG. 30, the first radiographic image capturing apparatus 10A may be devoid of the tape measure 72. Without the tape measure 72, the first radiographic image capturing apparatus 10A provides the same advantages offered by components thereof other than the tape measure 72.

As described above, major components of the joining mechanism 82 are provided in the cassette 12. However, the joining mechanism 82 may be provided in the radiation source device 18. Such a modification offers the same advantages as those referred to above.

The first radiographic image capturing apparatus 10A may be modified as described below.

Figure 31:
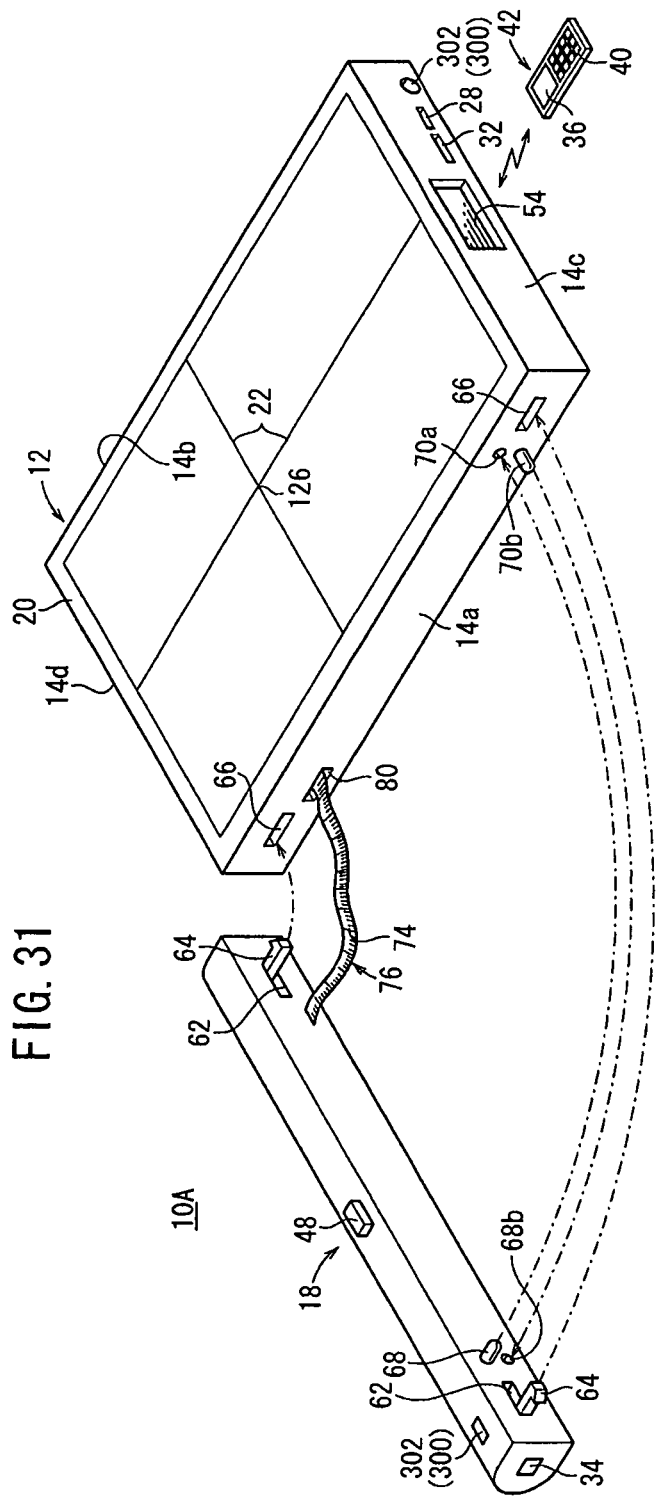
FIG. 31 is a perspective view of another modification of the first radiographic image capturing apparatus.

FIG. 31 shows a first radiographic image capturing apparatus 10A according to a modification, in which the unlocking button 34, the hook 64, etc., are provided in the radiation source device 18.

As shown in FIG. 31, the side 14a of the cassette 12 does not include the aforementioned holders 16a, 16b, and the radiation source device 18 has a flat side, which faces the side 14a of the cassette 12. Opposite ends of the radiation source device 18 have respective unlocking buttons 34. The radiation source device 18 also has through holes 62 and hooks 64 provided in the flat side thereof, which faces the side 14a of the cassette 12, near opposite ends of the radiation source device 18. Connection terminals 68a, 68b are disposed on the flat side of the radiation source device 18 near one of the ends of the radiation source device 18.

The side 14a of the cassette 12 has through holes 66 defined therein, which are in alignment with the respective through holes 62 and connection terminals 70a, 70b, which in turn are in alignment with the connection terminals 68a, 68b.

The first radiographic image capturing apparatus 10A shown in FIG. 31 operates in the following manner. While the flat side of the radiation source device 18 and the side 14a of the cassette 12 face toward each other, the hooks 64 are inserted into the respective through holes 66, and the connection terminals 68a, 68b and the connection terminals 70a, 70b are brought into engagement with each other. At this time, the radiation source device 18 and the cassette 12 are integrally joined to each other.

The first radiographic image capturing apparatus 10A shown in FIG. 31 offers the same advantages as the first radiographic image capturing apparatus 10A according to the first embodiment.

According to the modification shown in FIG. 31, since the unlocking buttons 34 are disposed on opposite ends of the radiation source device 18, an operator 38 can easily disconnect the radiation source device 18 from the cassette 12, simply by detaching the radiation source device 18 from the cassette 12 while pressing the unlocking buttons 34.

Figure 32:
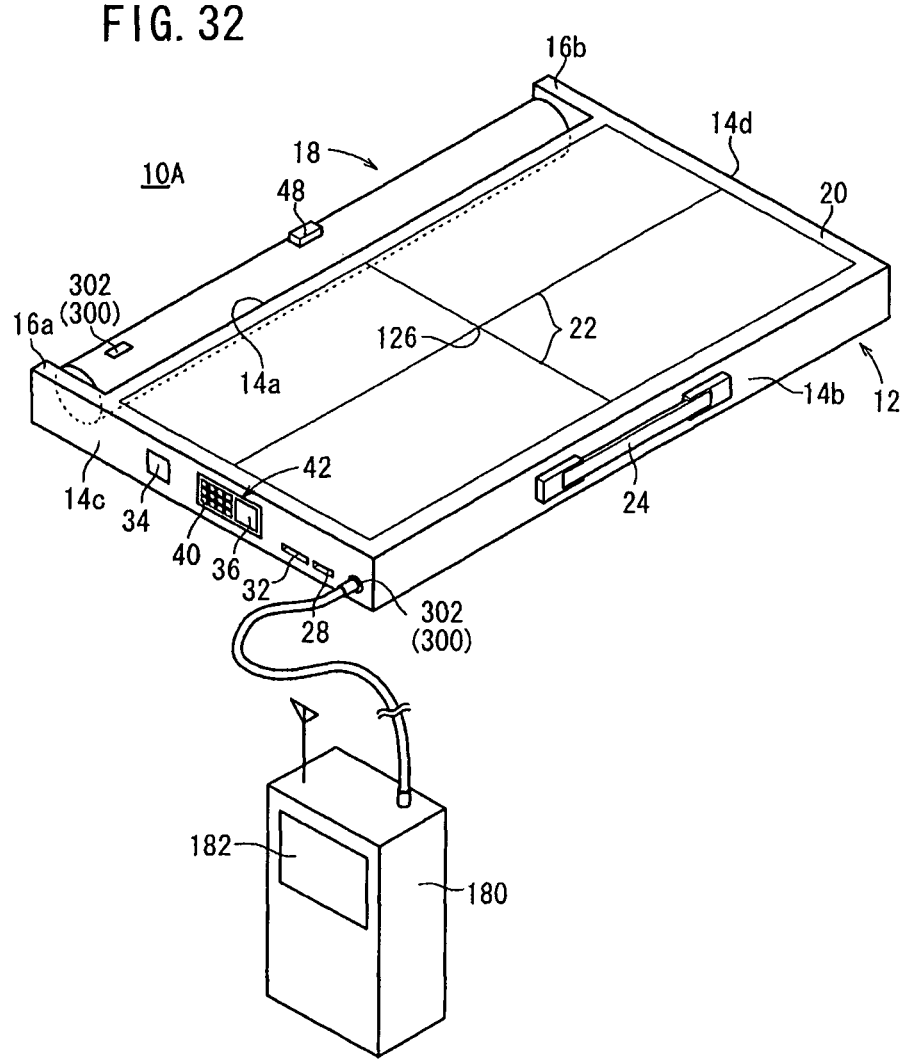
FIG. 32 is a perspective view of still another modification of the first radiographic image capturing apparatus.

In the first embodiment, as shown in FIG. 32, a cradle 180 for charging the batteries 308 of the first radiographic image capturing apparatus 10A may be positioned at a desired location in the hospital. The cradle 180 is not only capable of charging the batteries 308, but may also have a wireless or wired communication function for sending and receiving necessary information to and from an external device in the hospital. Information sent from the cradle 180 may include radiation image information recorded in the first radiographic image capturing apparatus 10A, which is connected to the cradle 180.

The cradle 180 has a display unit 182 for displaying the charged state of the first radiographic image capturing apparatus 10A, which is connected to the cradle 180, and other necessary information, including radiation image information acquired from the first radiographic image capturing apparatus 10A.

A plurality of cradles 180 may be connected through a network, and charged states of respective first radiographic image capturing apparatus 10A, which are connected to the cradles 180, may be retrieved through the network, so that the user can confirm the locations of first radiographic image capturing apparatus 10A that are sufficiently charged, based on the retrieved charged states.

A radiographic image capturing apparatus 10B according to a second embodiment of the present invention, which will hereinafter be referred to as a "second radiographic image capturing apparatus 10B," will be described below with reference to FIGS. 33 through 40.

The second radiographic image capturing apparatus 10B essentially is identical in structure to the first radiographic image capturing apparatus 10A according to the first embodiment, but differs therefrom in that a detecting screen 250 is drawn out slightly from the cassette 12 through the side 14b thereof that is remote from the side 14a on which the holders 16a, 16b project, and a weight bar 252 is coupled to a distal end of the detecting screen 250. Among the other sides 14c, 14d of the cassette 12, side 14c has the first energy input/output unit 300 or the second energy input/output unit 302 (see FIG. 13) for inputting and outputting electric power through a wired or wireless link, for example, a USB terminal 28 that serves as an interface means for sending and receiving information to and from an external device, a card slot 32 for inserting the memory card 30 therein, and the unlocking button 34, to be described later. On an upper surface 254 of the cassette 12, the mobile terminal 42 is mounted, which is detachable from the cassette 12 and includes the display unit 36 and the operating unit 40, which is operated by the operator 38. The radiation source device 18 has an exposure switch 48, which can be operated by the operator 38 in order to cause the radiation source 44, which shall be descried later, to start emitting radiation 46.

Figure 33:
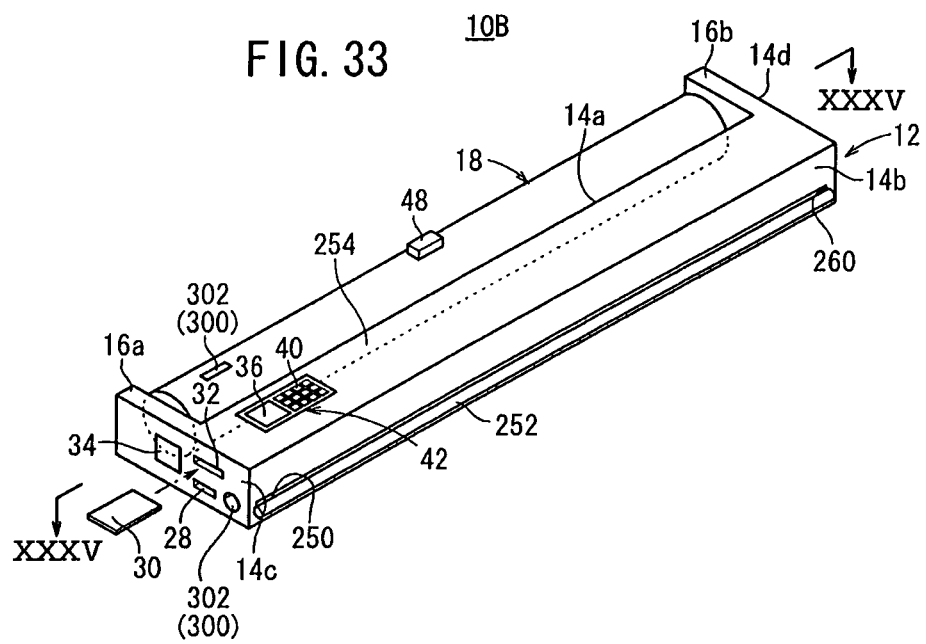
FIG. 33 is a perspective view of a radiographic image capturing apparatus (second radiographic image capturing apparatus) according to a second embodiment of the present invention.
Figure 34:
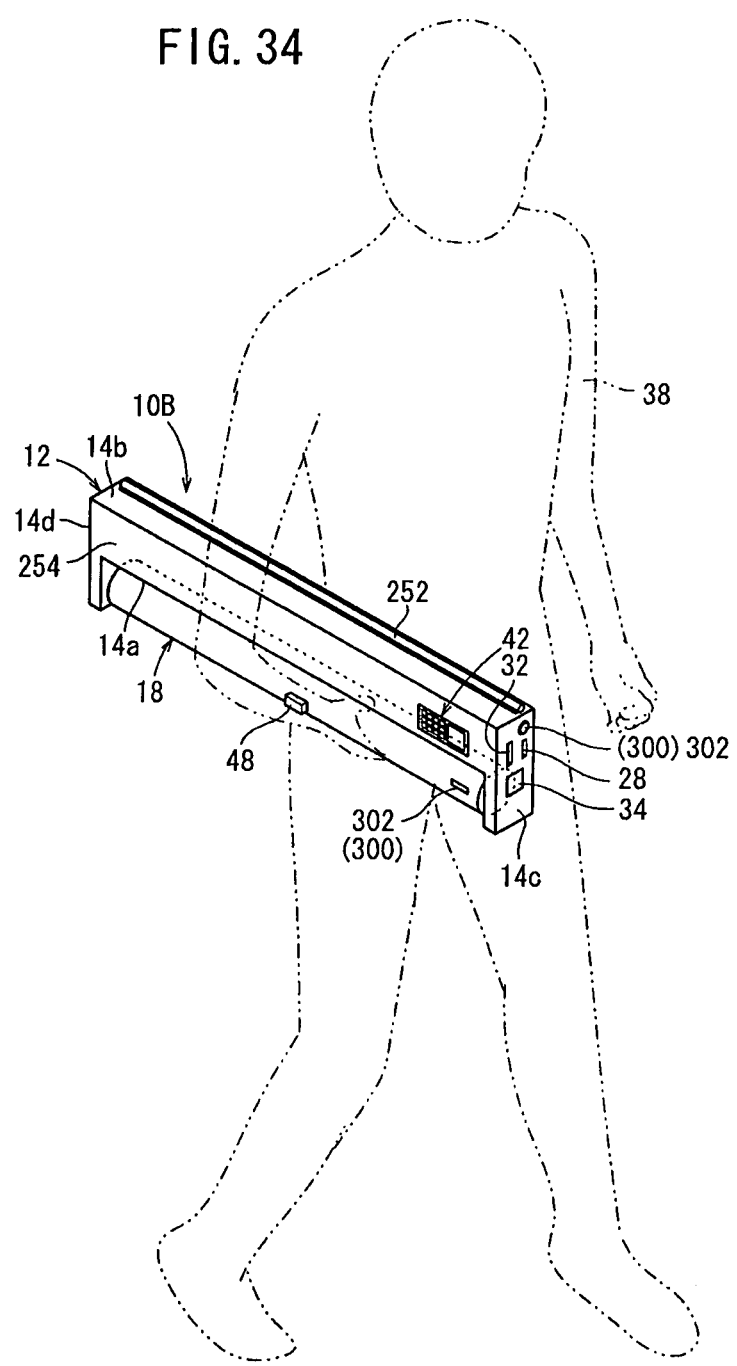
FIG. 34 is a perspective view showing the manner in which the second radiographic image capturing apparatus is carried.

FIGS. 33 and 34 show the second radiographic image capturing apparatus 10B in a state of being carried by the operator 38. When the second radiographic image capturing apparatus 10B is carried by the operator 38, the radiation source device 18 and the cassette 12 are joined integrally to each other.

When the second radiographic image capturing apparatus 10B is brought to a site, such as a disaster site, a home-care service site, or the like, the second radiographic image capturing apparatus 10B is expanded to result in the state shown in FIGS. 35 through 40.

Figure 35:
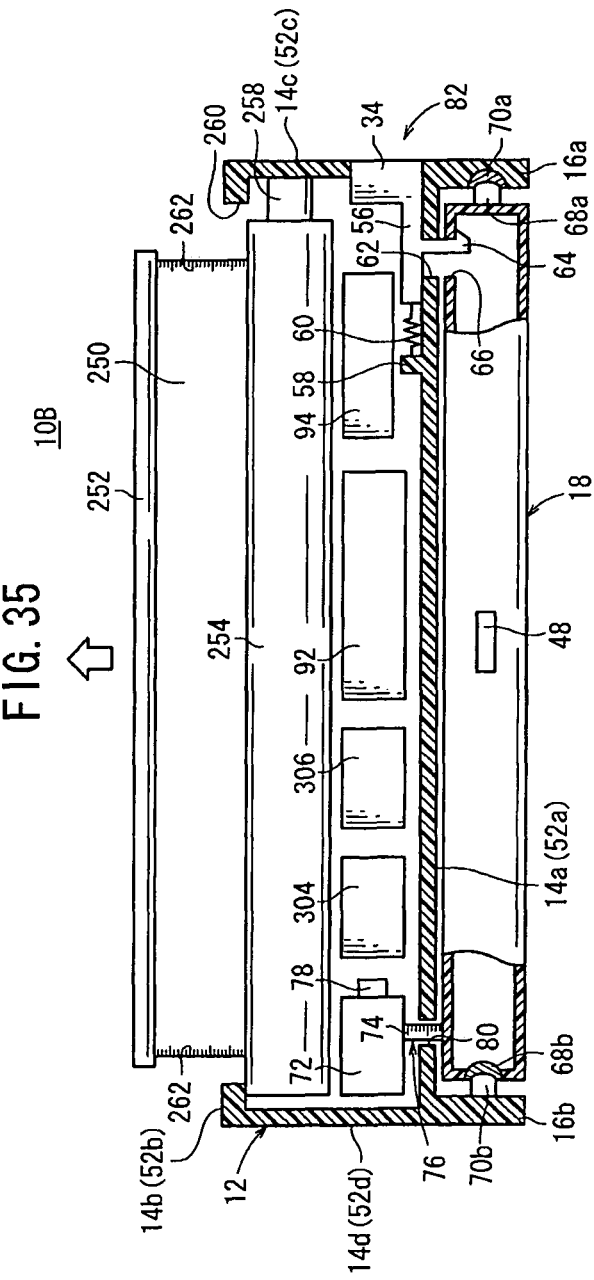
FIG. 35 is a horizontal cross-sectional view taken along line XXXV-XXXV of FIG. 33.
Figure 36:
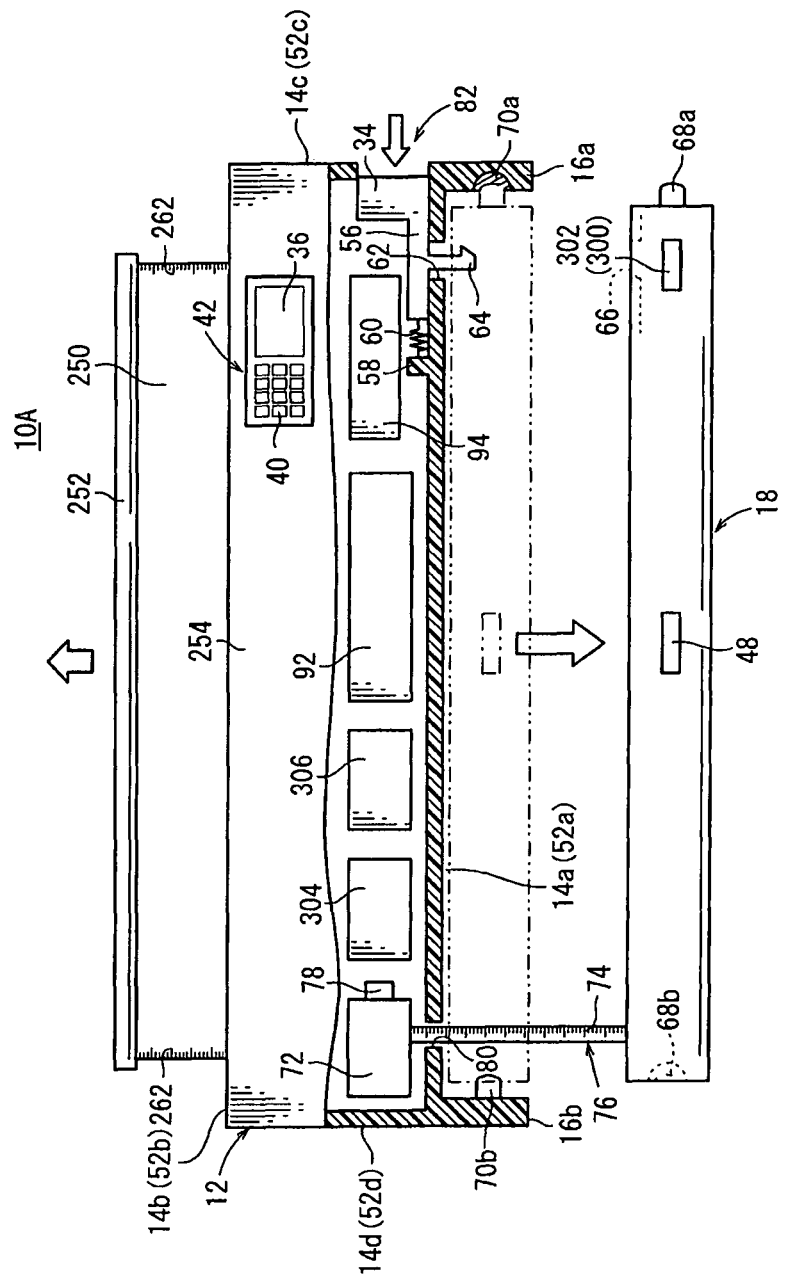
FIG. 36 is a plan view of the second radiographic image capturing apparatus, showing a radiation source device separated from a cassette shown in FIG. 33.
Figure 37:
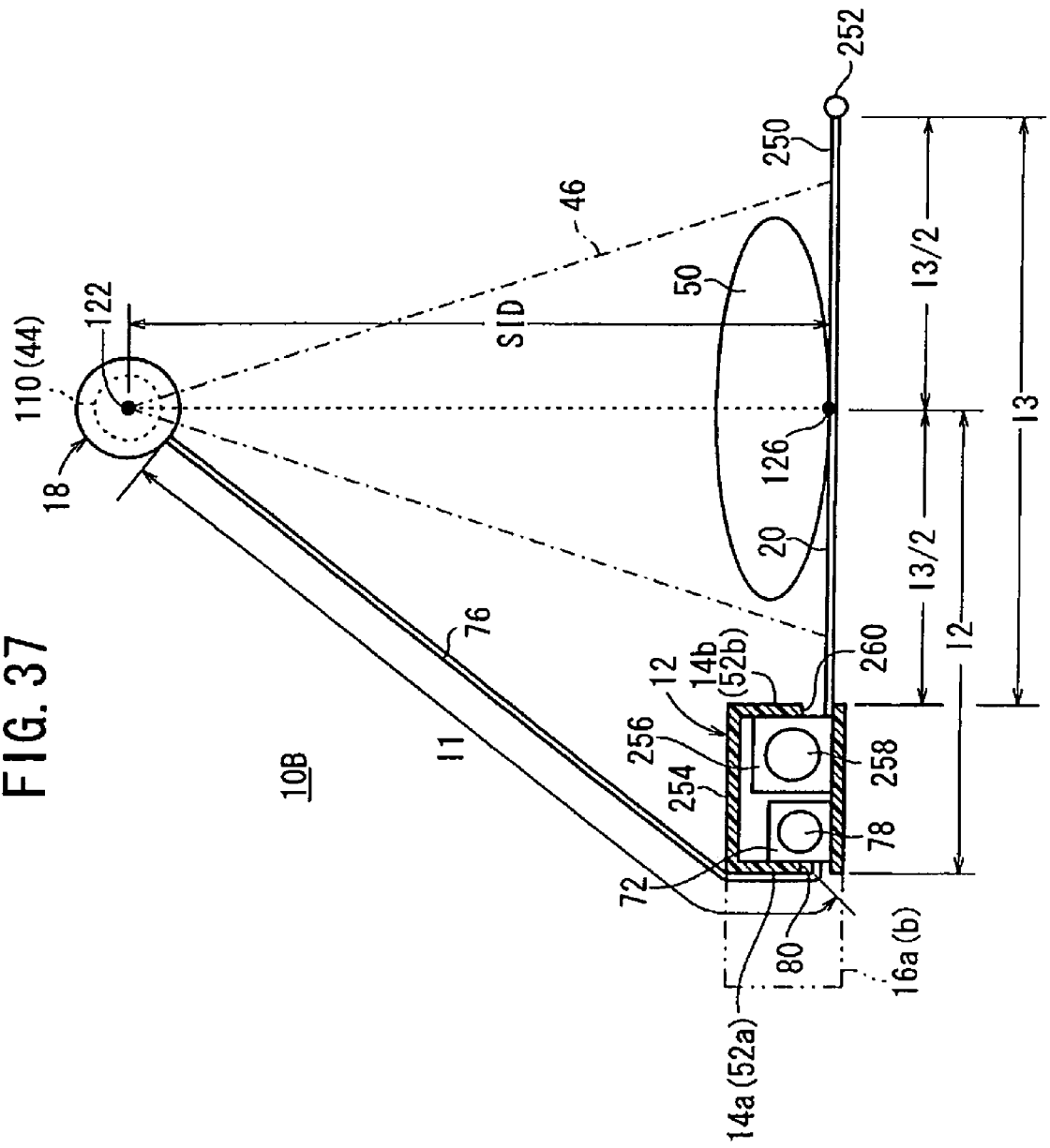
FIG. 37 is a cross-sectional view showing the manner in which the second radiographic image capturing apparatus captures a radiographic image.
Figure 39:
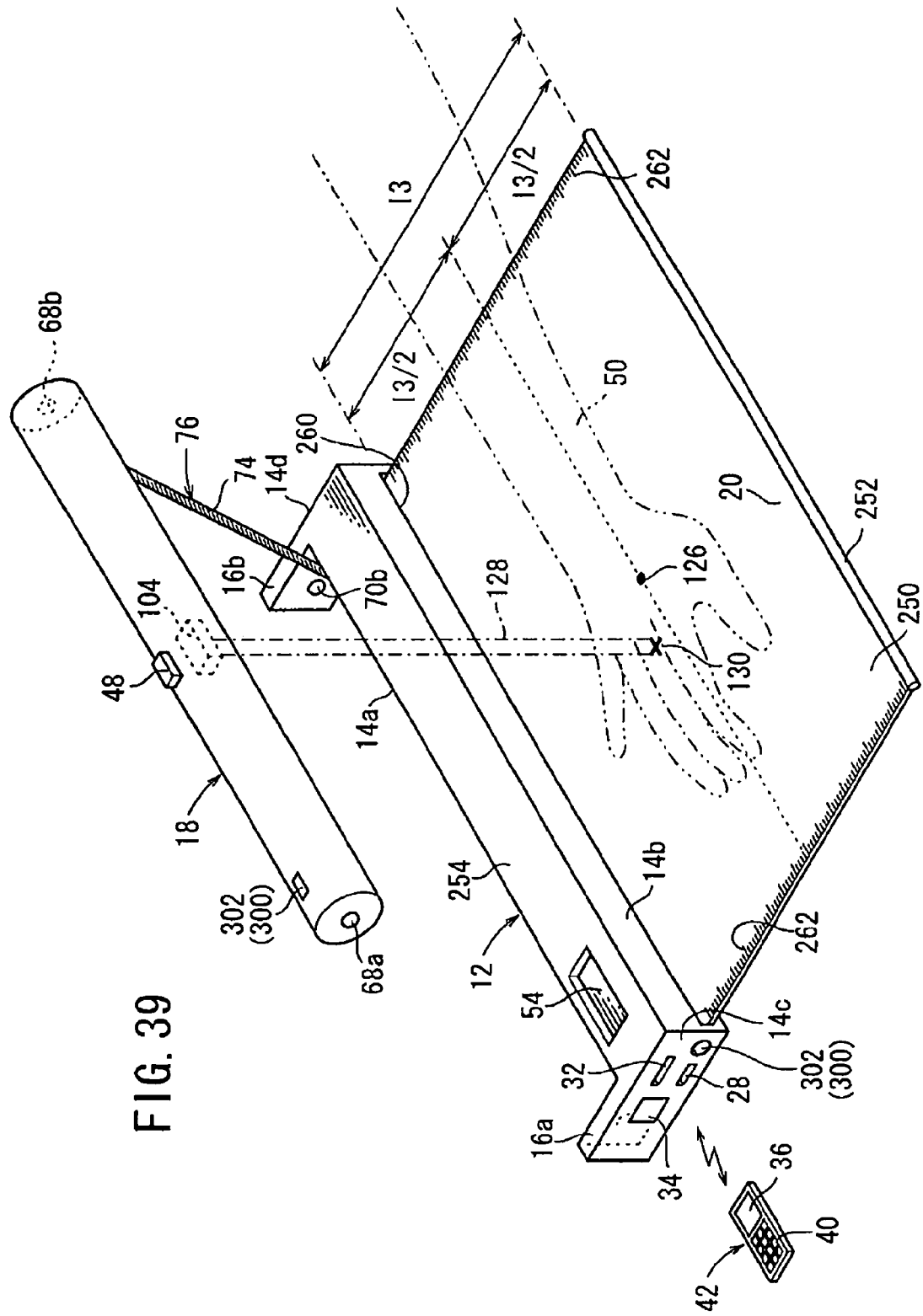
FIG. 39 is a perspective view showing the manner in which the second radiographic image capturing apparatus is readied to capture radiographic images.

As shown in FIG. 39, the upper surface 254 of the cassette 12 has the recess 54, which accommodates the mobile terminal 42 therein. As shown in FIGS. 35 and 37, the cassette 12 houses therein a storage box 256, accommodating therein a roll screen, which constitutes a rolled form of the detecting screen 250 and is made of a flexible material permeable to radiation 46. The storage box 256 supports on a side thereof a rotary encoder 258 for detecting the length by which the detecting screen 250 has been reeled out from the storage box 256. The side wall 52b of the cassette 12, which makes up the side 14b, has a slot 260 defined therein, through which the detecting screen 250 can be reeled out from the storage box 256.

Figure 40:
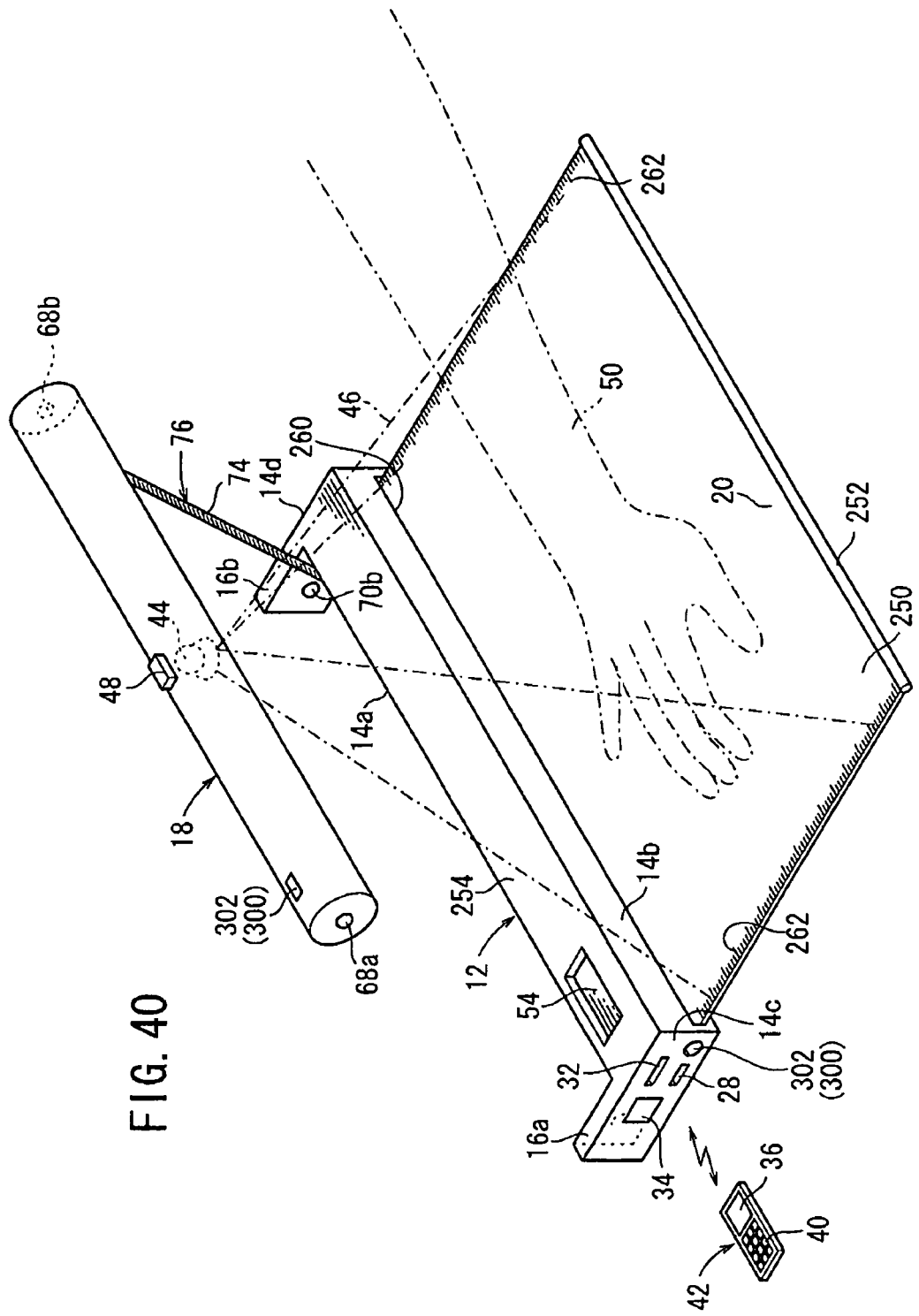
FIG. 40 is a perspective view showing the manner in which the second radiographic image capturing apparatus captures a radiographic image.

When the operator 38 pulls the weight bar 252 in a direction away from the cassette 12, the detecting screen 250 is drawn or extended out from the storage box 256 through the slot 260. At times when the second radiographic image capturing apparatus 10B is being carried, the detecting screen 250 is rolled up inside the storage box 256. When the second radiographic image capturing apparatus 10B is operated to capture radiographic images, as shown in FIGS. 37, 39 and 40, the detecting screen 250 is drawn out or extended substantially flatwise underneath the radiation source device 18 by the operator 38 pulling the weight bar 252. The detecting screen 250 has gradations 262 on both side edges thereof along the direction in which the detecting screen 250 is pulled.

Figure 38:
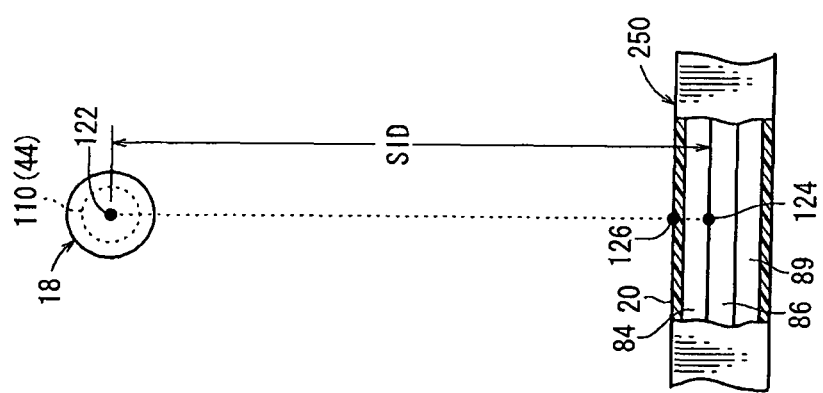
FIG. 38 is a view showing in greater detail a source-to-image distance (SID) that is illustrated in FIG. 37.

As shown in FIG. 38, the detecting screen 250 houses therein a grid 84 for removing scattered rays of radiation 46 from the subject 50 when the radiation source 44 applies radiation 46 to the subject 50, a radiation detector 86 for detecting radiation 46 that has passed through the subject 50, and a lead sheet 89 for absorbing back scattered rays of radiation 46, which are successively arranged in this order from the irradiated surface 20 of the detecting screen 250, i.e., the upper surface of the detecting screen 250, as shown in FIGS. 37 through 40. The irradiated surface 20 may be constructed as the grid 84. The grid 84, the radiation detector 86, and the lead sheet 89 are flexible.

For irradiating the subject 50 with radiation 46 in order to capture radiographic images of the subject 50, a preparatory procedure must first be performed for readying the second radiographic image capturing apparatus 10B for capturing radiographic images. Such a preparatory procedure includes a process for presetting a source-to-image distance (SID), which represents an distance (imaging distance) between the focus point 122 of the radiation source 44 and a position 124 (see FIG. 38) on the radiation detector 86 that lies straight below the focus point 122, and a process for bringing the central position 126 of the irradiated surface 20 of the detecting screen 250 into alignment with the center of a range within which the irradiated surface 20 is irradiated with radiation 46.

The preparatory procedure is carried out as follows. As shown in FIGS. 37 through 39, while the radiation source device 18 is separated from the cassette 12, the operator 38 pulls the ribbon 76 from the tape measure 72 until the length of the ribbon 76, which is reeled out from the tape measure 72, becomes equal to the reeled-out length 11 depending on the SID. The laser pointer 104 is controlled by the radiation source controller 102 in order to apply a laser beam 128 to the irradiated surface 20, thereby displaying a crisscross mark 130 on the irradiated surface 20, which represents the center of a range within which the irradiated surface 20 is irradiated with radiation 46.

The operator 38 determines the central position of the irradiated surface 20 by observing the gradations 262 thereon. The SID, the reeled-out length 11 depending on the SID, and a distance 12 between the position 124 or the central position 126 and the side 14a having the hole 80 through which the ribbon 76 is pulled out, are related to each other according to the equation $SID \approx (11^2 - 12^2)^{1/2}$.

After the ribbon 76 has been pulled from the tape measure 72 by the reeled-out length 11, the operator 38 adjusts the position of the radiation source device 18 so as to bring the mark 130 displayed on the irradiated surface 20 into alignment with the central position 126. Thereafter, the operator 38 turns on the exposure switch 48 in order to enable the radiation source 44 to apply radiation 46 with respect to the subject 50 on the irradiated surface 20, thereby capturing radiographic images of the subject 50, as shown in FIG. 40. In FIG. 40, an example is shown in which a radiographic image of a hand of the subject 50 is captured.

The second radiographic image capturing apparatus 10B also operates according to the operation sequences shown in FIGS. 23 through 29. The second radiographic image capturing apparatus 10B is operated according to a preparatory procedure and an image capturing process as follows.

First, the operator performs operations to ready the second radiographic image capturing apparatus 10B for capturing radiographic images at a site where the second radiographic image capturing apparatus 10B has been carried. The operator 38 operates the operating unit 40 of the mobile terminal 42 in order to register image capturing conditions, including subject information (e.g., SID) of the subject 50 to be imaged.

The operator 38 pulls the weight bar 252 in order to draw or extend the detecting screen 250 from the storage box 256 by a given length (drawn-out length 13), which is required to capture radiographic images of a body region of the subject 50 to be imaged. The rotary encoder 258 detects the drawn-out length 13 of the detecting screen 250, and sends a signal representative of the detected drawn-out length 13 to the SID determining unit 168.

When the unlocking button 34 is pressed by the operator 38, the hook 64 and the slide 56 are displaced against the resiliency of the spring 60 and along the side wall 52a toward the side wall 52d, thereby bringing the hook 64 out of engagement with the edge of the through hole 66.

While the hook 64 is kept out of engagement with the edge of the through hole 66, i.e., while the operator 38 presses the unlocking button 34, the operator 38 removes or separates the radiation source device 18 from the cassette 12. The connection terminal 68a becomes disengaged from the connection terminal 70a, and the connection terminal 68b becomes disengaged from the connection terminal 70b, thereby releasing the radiation source device 18 and the cassette 12 from each other. The operator 38 sets the imaging distance and brings the mark 130, which is displayed on the irradiated surface 20, into alignment with the central position 126. Thereafter, the operator 38 places and positions the subject 50 between the irradiated surface 20 and the radiation source device 18. The operator 38 moves the radiation source device 18 in order to reel out the ribbon 76 from the tape measure 72, until the actual reeled-out length of the ribbon 76 reaches the reeled-out length 11 depending on the SID.

After having adjusted the position of the radiation source device 18 until the mark 130 and the central position 126 are aligned with, each other, the operator 38 places or positions the subject 50 on the irradiated surface 20, so that the center of a body region of the subject 50 to be imaged is aligned with the central position 126, i.e., the position of the mark 130.

After the above positional adjustment has been carried out, the radiation source device 18 is secured to the adjusted position by a holder, not shown, for example.

After the subject 50 is positioned, the operator 38 turns on the exposure switch 48 in order to start capturing radiographic images of the subject 50.

The second radiographic image capturing apparatus 10B offers the same advantages as the first radiographic image capturing apparatus 10A.

While the second radiographic image capturing apparatus 10B is transported, the radiation source device 18 and the cassette 12 are coupled to each other integrally by the joining mechanism 82. While the second radiographic image capturing apparatus 10B is operated to capture radiographic images, the radiation source device 18 and the cassette 12 are separated from each other, and the detecting screen 250 is drawn and extended from the cassette 12. Thereafter, the radiation source 44 of the radiation source device 18 emits radiation 46, which is applied to the subject 50. Therefore, the second radiographic image capturing apparatus 10B of a portable type, which is small in size and weight, can simply and quickly be readied for capturing radiographic images.

The storage box 256, which is disposed in the cassette 12, accommodates therein the detecting screen 250 in a rolled-up form, so as to be flexible and capable of being extended in sheet form. When the second radiographic image capturing apparatus 10B is carried to a site, such as a disaster site, a home-care service site, or the like, the detecting screen 250 is stored in a rolled-up form inside the storage box 256. When the second radiographic image capturing apparatus 10B is operated to capture radiographic images, the detecting screen 250 is drawn out from the storage box 256 in a flat sheet form. Therefore, the second radiographic image capturing apparatus 10B is small in overall size.

A portable radiographic image capturing apparatus according to a third embodiment of the present invention, which hereinafter will be referred to as a "third radiographic image capturing apparatus 10C," will be described in detail below with reference to FIGS. 41 through 47.

The third radiographic image capturing apparatus 10C includes the radiation source device 18, the cassette 12, and a personal computer (controller, PC) 280, which is electrically connected to the radiation source device 16 by a wired or wireless input/output unit, as well as being electrically connected to the cassette 12 by a wired or wireless input/output unit. Further, the third radiographic image capturing apparatus 10C incorporates therein a digital camera 270 for capturing an image of a predetermined imaging area. The PC 280 can be operated by the operator 38 (see FIG. 44) of the third radiographic image capturing apparatus 10C. The PC 280 is capable of sending signals to and receiving signals from a medical organization to which the operator 38 belongs, by way of wireless communications via a network such as a public network or the like.

Figure 41:
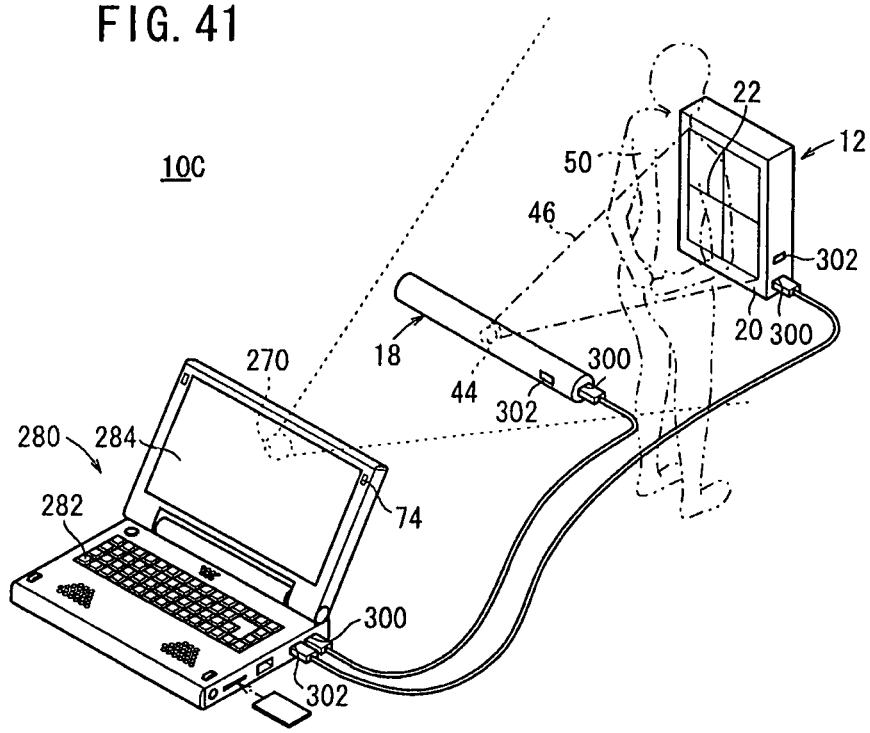
FIG. 41 is a perspective view of a radiographic image capturing apparatus (third radiographic image capturing apparatus) according to a third embodiment of the present invention.
Figure 42:
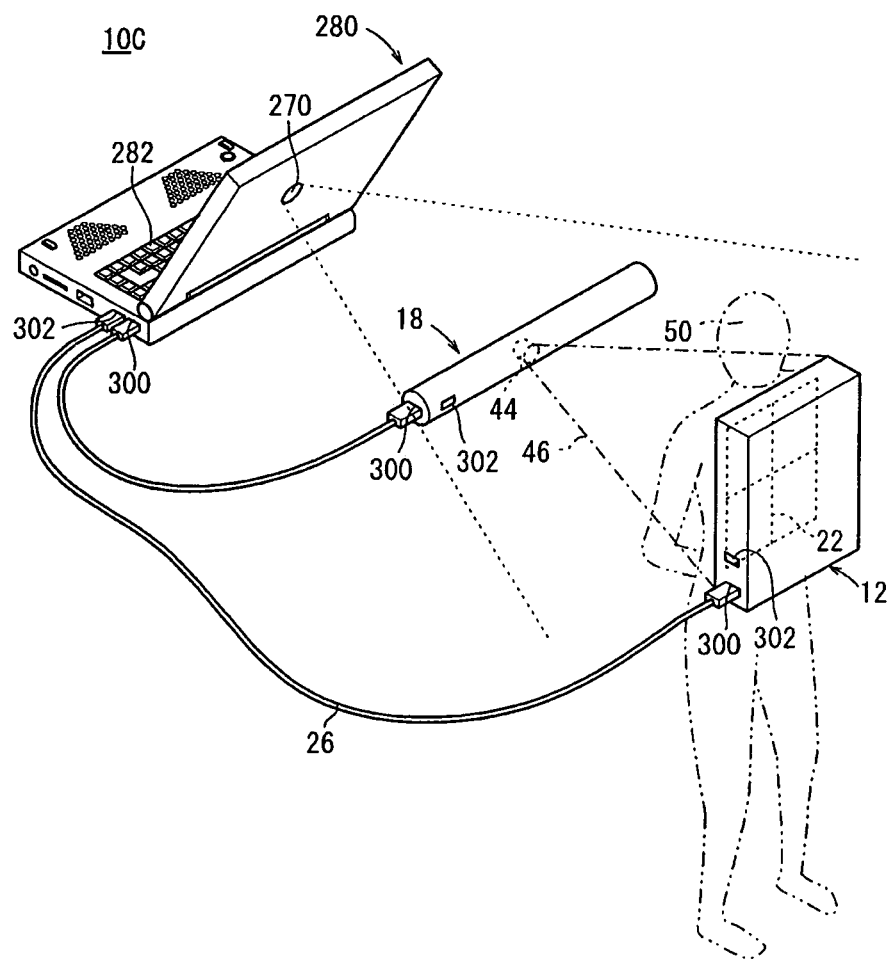
FIG. 42 is a perspective view of the third radiographic image capturing apparatus.
Figure 43:
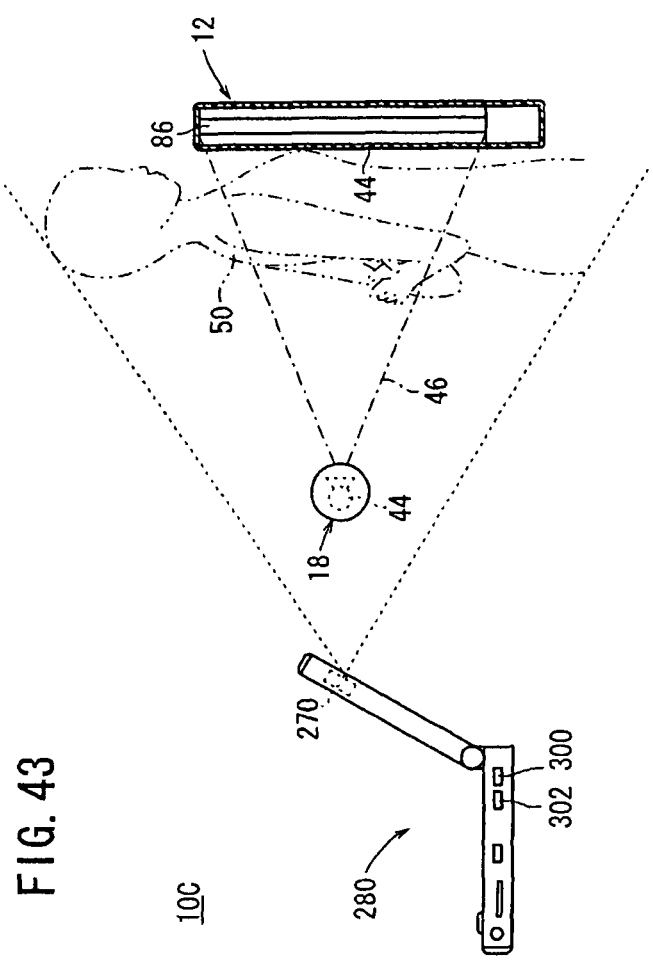
FIG. 43 is a side elevational view of the third radiographic image capturing apparatus.

The cassette 12 includes the battery unit 304, a battery controller 306, a radiation detector 86, a cassette controller 92, and a transceiver 94, which are identical to those shown in FIG. 11. As shown in FIG. 41, the cassette 12 has a first energy input/output unit 300 and a second energy input/output unit 302 located on a side wall of the casing. The radiation source device 18 includes a battery unit 304, a battery controller 306, a transceiver 100, a radiation source controller 102 for controlling the radiation source 44, and a laser pointer 104, which are identical to those shown in FIG. 11. A first energy input/output unit 300 and a second energy input/output unit 302, which are identical to those of the cassette 12, are mounted respectively on a side wall and a circumferential wall of the casing of the radiation source device 18, as shown in FIG. 41.

As shown in FIG. 41, the PC 280 comprises a notebook-shaped personal computer, including an operating unit 282 such as a keyboard, a mouse, or the like, and a display unit 284. Alternatively, the PC 280 may be replaced with a mobile phone or a PDA (Personal Digital Assistant).

The PC 280 has a power supply switch, speakers, a microphone, and other accessories, similar to those of ordinary notebook-shaped personal computers. The PC 280 incorporates therein a transceiver 288 (see FIG. 45) for sending information to and receiving information from an external device such as a network, the radiation source device 18, the cassette 12, or the like. The PC 280 also includes, on a side wall thereof, a first energy input/output unit 300, and a second energy input/output unit 302. In FIG. 41, the first energy input/output unit 300 of the PC 280 is connected by a cable to the first energy input/output unit 300 of the radiation source device 18, while the second energy input/output unit 302 of the PC 280 is connected by a cable to the first energy input/output unit 300 of the cassette 12. However, the first energy input/output unit 300 and the second energy input/output unit 302 may be connected wirelessly.

Figure 45:
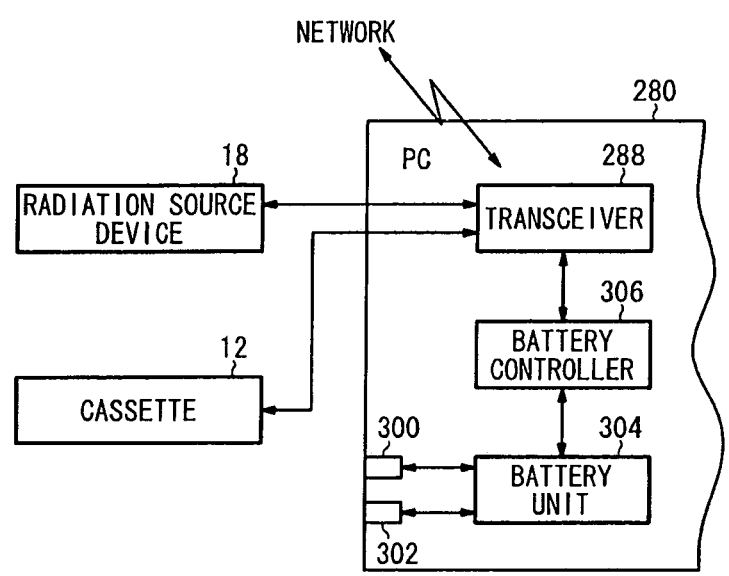
FIG. 45 is a block diagram of a portion of a PC (Personal Computer), which is used with the third radiographic image capturing apparatus.

As shown in FIG. 45, the PC 280 includes a battery unit 304 and a battery controller 306, which are identical to those of the radiation source device 18.

Figure 44:
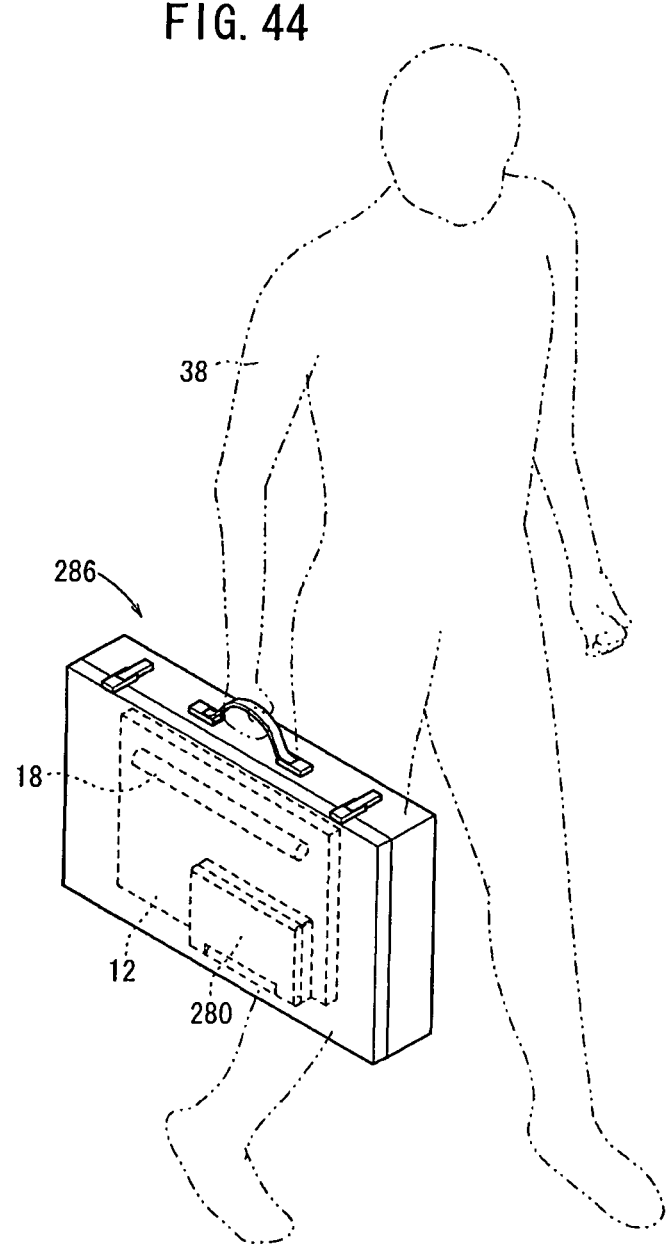
FIG. 44 is a perspective view showing the manner in which the third radiographic image capturing apparatus is carried.

FIG. 44 shows the manner in which the third radiographic image capturing apparatus 10C is carried by an operator 38.

When the third radiographic image capturing apparatus 10C is carried by the operator 38, the radiation source device 18, the cassette 12, and the folded PC 280 are electrically disconnected and housed in an attaché case 286. The operator 38 can grip a grip 24 of the attaché case 286 and carry the attaché case 286 from the medical organization to a desired site, e.g., a disaster site or a home-care service site. At the site where the attaché case 286 has been carried, the operator 38 can take out the radiation source device 18, the cassette 12, and the folded PC 280 from the attaché case 286, and assemble them into the configuration shown in FIGS. 41 through 43. The operator 38 then can perform a preparatory procedure in order to ready the third radiographic image capturing apparatus 10C for capturing radiographic images of a person at a disaster site or a home-care service site.

The third radiographic image capturing apparatus 10C also operates according to the operation sequences shown in FIGS. 23 through 29. In accordance with a preparatory procedure, the third radiographic image capturing apparatus 10C operates in the following manner.

The operator 38 takes the radiation source device 18, the cassette 12, etc., out of the attaché case 286, and electrically connects the radiation source device 18 and the cassette 12 to the PC 280 in a wired or wireless fashion. The operator 38 places the PC 280, the radiation source device 18, and the cassette 12 in the positional relationship shown in FIGS. 41 through 43.

Then, the operator 38 starts up the PC 280, thereby readying the third radiographic image capturing apparatus 10C for capturing radiographic images. Thereafter, the operator 38 turns on the exposure switch 48 to begin capturing radiographic images.

In the operation sequences shown in FIGS. 23 through 29, if the distance between any two of the devices that incorporate the battery controller 306 therein, i.e., the radiation source device 18, the cassette 12, the PC 280, etc., of the third radiographic image capturing apparatus 100, and which belong to the third radiographic image capturing apparatus 100, satisfies the certain condition referred to above, then the third activator/deactivator 332C outputs an activation signal. If the distance does not satisfy the certain condition after the third activator/deactivator 332C has output the activation signal, then the third activator/deactivator 332C outputs a full deactivation signal.

More specifically, the third activator/deactivator 332C (see FIG. 17A) according to the first mode outputs an activation signal if the linear distance between at least two of the radiation source device 18, the cassette 12, and the PC 280 becomes equal to or smaller than the preset reference distance. The third activator/deactivator 332C (see FIG. 17B) according to the second mode outputs an activation signal if the linear distance between at least two of the radiation source device 18, the cassette 12, and the PC 280 lies within the communication range of each of the devices. The third activator/deactivator 332C (see FIG. 17C) according to the third mode outputs an activation signal if the linear distance between at least two of the radiation source device 18, the cassette 12, and the PC 280 lies within a range in which the devices can be connected in a wired or wireless fashion.

If the distance between the cassette 12 and the radiation source device 18, for example, satisfies the certain condition, then the third activator/deactivator 332C outputs an activation signal in the cassette 12 and the radiation source device 18. Thereafter, if the distance between the cassette 12 and the PC 280 and the distance between the radiation source device 18 and the PC 280 also satisfy the certain condition, then the third activator/deactivator 332C outputs an activation signal in the PC 280. Thereafter, only if the PC 280 moves away, whereby the distance between the cassette 12 and the PC 280 and the distance between the radiation source device 18 and the PC 280 fail to satisfy the certain condition, then the third activator/deactivator 332C outputs a full deactivation signal in the PC 280. Although the third activator/deactivator 332C outputs a full deactivation signal also in the cassette 12 and the radiation source device 18, since the distance between the cassette 12 and the radiation source device 18 satisfies the certain condition, the third activator/deactivator 332C immediately outputs an activation signal, thus making it possible to supply electric power.

If the distance between any two of the cassette 12, the radiation source device 18, and the PC 280 of the third radiographic image capturing apparatus 10C satisfies the certain condition, then since it becomes possible to supply electric power using such devices, it also is possible to supply electric power between either one of the devices and another device of another third radiographic image capturing apparatus 10C.

For example, if from among the cassette 12, the radiation source device 18, and the PC 280 of the third radiographic image capturing apparatus 10C that is used to capture radiographic images, the distance between the cassette 12 and the radiation source device 18 satisfies the certain condition, then it becomes possible to supply electric power between the aforesaid cassette 12 and the aforesaid radiation source device 18 that are used to capture radiographic images, and also to supply electric power between the aforesaid cassette 12 and another radiation source device 18 that is not used to capture radiographic images. It also is possible to supply electric power between the aforesaid cassette 12 and another cassette 12 that is not used to capture radiographic images, between the aforesaid radiation source device 18 and another radiation source device 18 that is not used to capture radiographic images, and between the aforesaid radiation source device 18 and another cassette 12 that is not used to capture radiographic images.

If from among the cassette 12, the radiation source device 18, and the PC 280 of the third radiographic image capturing apparatus 10C that is used to capture radiographic images, the distance between the cassette 12 and the PC 280 satisfies the certain condition, then it is possible to supply electric power between the aforesaid cassette 12 and the PC 280 that are used to capture radiographic images, and also to supply electric power between the aforesaid cassette 12 and another radiation source device 18 that is not used to capture radiographic images. It also is possible to supply electric power between the aforesaid cassette 12 and another cassette 12 that is not used to capture radiographic images, between the PC 280 and another radiation source device 18 that is not used to capture radiographic images, and between the PC 280 and another cassette 12 that is not used to capture radiographic images.

Similarly, if from among the cassette 12, the radiation source device 18, and the PC 280 of the third radiographic image capturing apparatus 10C that is used to capture radiographic images, the distance between the radiation source device 18 and the PC 280 satisfies the certain condition, then it is possible to supply electric power between the aforesaid radiation source device 18 and the PC 280 that are used to capture radiographic images, and also to supply electric power between the aforesaid radiation source device 18 and another radiation source device 18 that is not used to capture radiographic images. It also is possible to supply electric power between the aforesaid radiation source device 18 and another cassette 12 that is not used to capture radiographic images, between the PC 280 and another radiation source device 18 that is not used to capture radiographic images, and between the PC 280 and another cassette 12 that is not used to capture radiographic images.

If the distances between the cassette 12, the radiation source device 18, and the PC 280 of the third radiographic image capturing apparatus 10C that is used to capture radiographic images satisfy the certain condition, then it is possible to supply electric power between the aforesaid cassette 12 and the aforesaid radiation source device 18 via the PC 280, and also to supply electric power between the aforesaid cassette 12 and another radiation source device 18 that is not used to capture radiographic images via the PC 280. It also is possible to supply electric power between the aforesaid cassette 12 and another cassette 12 that is not used to capture radiographic images via the PC 280, between the aforesaid radiation source device 18 and another radiation source device 18 that is not used to capture radiographic images via the PC 280, and between the aforesaid radiation source device 18 and another cassette 12 that is not used to capture radiographic images via the PC 280.

Electric power may be supplied via the PC 280 according to a process that differs from the process carried out by the first radiographic image capturing apparatus 10A and the second radiographic image capturing apparatus 10B. The different process comprises an electric power collecting process for collecting all or part of the electric power stored in the battery 308 of the radiation source device 18, and all or part of the electric power stored in the battery 308 of the cassette 12, for the battery unit 304 of the PC 280.

Figure 46:
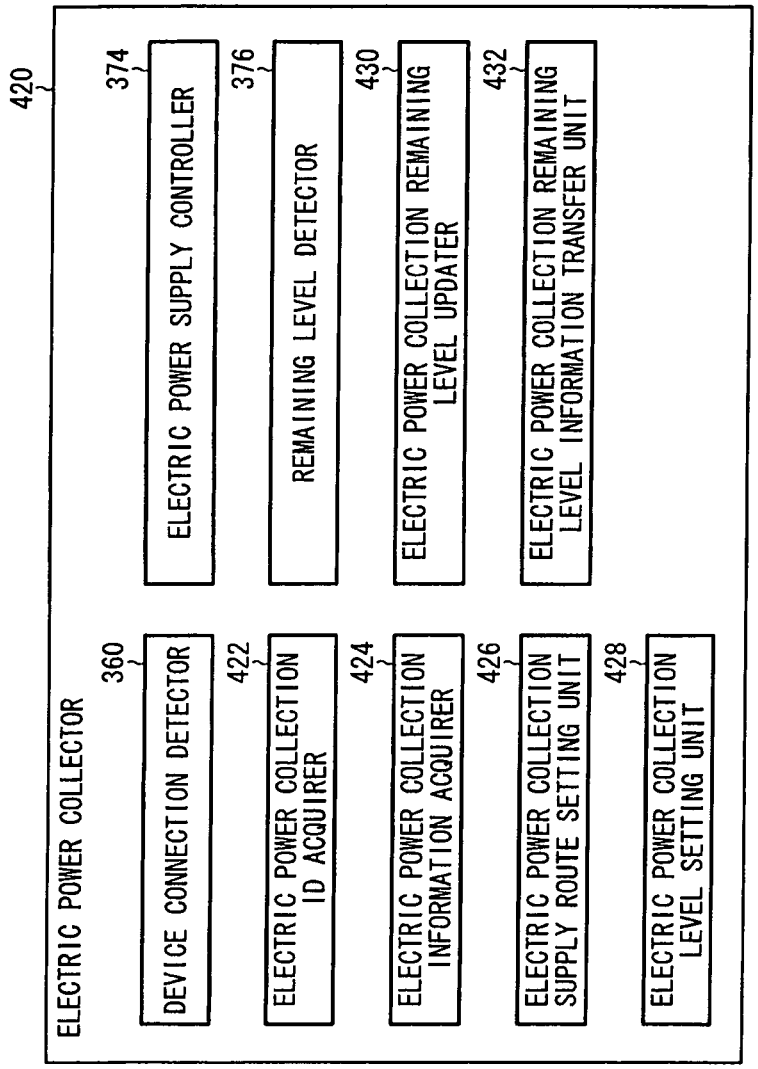
FIG. 46 is a block diagram of an electric power collector of the third radiographic image capturing apparatus.

An electric power collector 420 for carrying out the above electric power collecting process will be described below with reference to FIGS. 46 and 47.

The electric power collector 420 is incorporated in the battery controller 306. The electric power collector 420 is activated by an operation made by the operator 38 in order to instruct collection of electric power, e.g., by left-clicking on an icon representing collection of electric power. As shown in FIG. 46, the electric power collector 420 comprises the device connection detector 360, an electric power collection ID acquirer 422, an electric power collection information acquirer 424, an electric power collection supply route setting unit 426, an electric power collection level setting unit 428, the electric power supply controller 374, the remaining level detector 376, an electric power collection remaining level updater 430, and an electric power collection remaining level information transfer unit 432.

Details of an operation sequence of the electric power collector 420 will be described below with reference to FIGS. 46 and 47.

Figure 47:
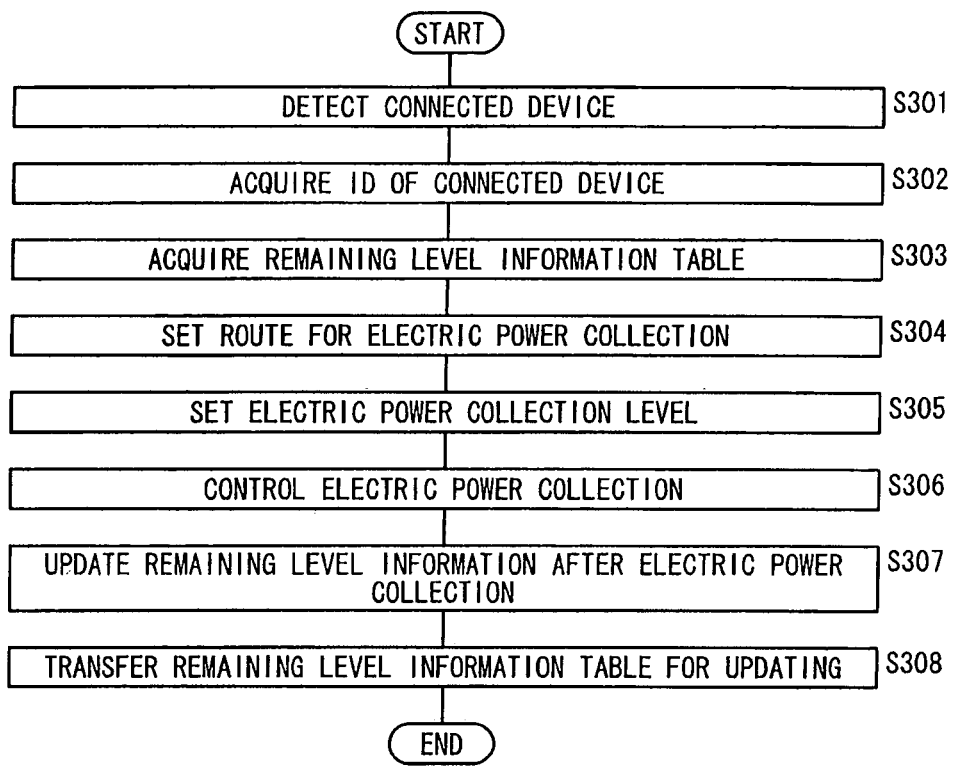
FIG. 47 is a flowchart of an operation sequence of the power collector shown in FIG. 46.

In step S301 shown in FIG. 47, the device connection detector 360 detects devices, i.e., the radiation source device 18 and the cassette 12, which are connected to the first energy input/output unit 300 and the second energy input/output unit 302 of the PC 280.

The electric power collection ID acquirer 422 sends a transfer request to the connected devices for transferring IDs. Based on the transfer request, the connected devices output IDs thereof to the electric power collector 420. The electric power collection ID acquirer 422 acquires the IDs from the connected devices, and registers the IDs in the memory 330 (see FIG. 14) in step S302.

The electric power collection information acquirer 424 acquires remaining level information tables corresponding to the IDs, and stores the acquired remaining level information tables in the memory 330 in step S303.

The electric power collection supply route setting unit 426 sets a supply route from the device connected to the first energy input/output unit 300 to the PC 280, and a supply route from the device connected to the second energy input/output unit 302 to the PC 280. Based on the set supply routes, in step S304, the electric power collection supply route setting unit 426 outputs supply source instruction signals to the electric power supply controllers 374 of the respective devices.

In step S305, the electric power collection level setting unit 428 sets an electric power collection level using the operating unit 282, e.g., a keyboard or a mouse, of the PC 280. The electric power collection level represents the sum of a first electric power level to be supplied from the device connected to the first energy input/output unit 300 to the battery 308 of the PC 280, and a second electric power level to be supplied from the device connected to the second energy input/output unit 302 to the battery 308 of the PC 280. The first electric power level and the second electric power level are supplied respectively to the electric power supply controllers 374 of the respective devices.

Based on the supply source instruction signals, the electric power supply controllers 374 of the devices control the batteries 308 thereof to output electric power. Further, based on a supply source instruction signal, the electric power supply controller 374 of the PC 280 controls the battery 308 thereof to input electric power in step S306. The electric power supply controllers 374 control the batteries 308 to supply electric power, and to be supplied with electric power, at a constant charging rate or at a discharging rate based on the remaining level sent from the remaining level detector 376. If the level of electric power to be supplied is low, then it is possible to charge and discharge the batteries 308 quickly.

In step S307, the electric power collection remaining level updater 430 updates the remaining battery level corresponding to the ID of the device that is connected to the first energy input/output unit 300, by subtracting the first electric power level from the remaining battery level. The electric power collection remaining level updater 430 also updates the remaining battery level corresponding to the ID of the device that is connected to the second energy input/output unit 302, by subtracting the second electric power level from the remaining battery level.

When the updating process of the electric power collection remaining level updater 430 is completed, then in step S308, the electric power collection remaining level information transfer unit 432 transfers the remaining level information tables via the network to the database of the data center for updating.

The electric power collector 420 may be activated by operations made by the operator 38 on the operating unit 282, for example, regardless of location and time. For example, when the third radiographic image capturing apparatus 10C is carried into a medical organization, the electric power collector 420 may be activated in order to collect electric power in the battery 308 of the PC 280. Then, when the third radiographic image capturing apparatus 10C is carried to a site outside of the medical organization, the radiation source device 18 and the cassette 12, which are used to capture radiographic images, may be supplied with electric power from the PC 280. At this time, the electric power manager 390 supplies an optimum electric power level for capturing radiographic images to the radiation source device 18 and to the cassette 12. Alternatively, the electric power collector 420 may be activated at a site outside of the medical organization, so as to collect into the PC 280 electric power from a radiation source device 18 and a cassette 12, which have deteriorated significantly and which cannot be used to capture radiographic images, and to supply the collected electric power to the radiation source device 18 and the cassette 12 that currently are being used to capture radiographic images.

Since the PC 280 can supply electric power to respective devices, it is possible to set a supply route from the PC 280 to a radiation source device 18 that is used to capture radiographic images, as well as a supply route from the PC 280 to a cassette 12 that is used to capture radiographic images. It also is possible to set a supply route from the PC 280 as a supply source to the aforesaid radiation source device 18, as well as a supply route from the PC 280 as a supply source to the aforesaid cassette 12. Furthermore, it is possible to set a supply route from the aforesaid radiation source device 18 via the PC 280 to the aforesaid cassette 12, as well as a supply route from the aforesaid cassette 12 via the PC 280 to the aforesaid radiation source device 18.

Since electric power can be supplied from the PC 280 to the radiation source device 18 and the cassette 12, or electric power can be supplied between the radiation source device 18 and the cassette 12 via the PC 280, the PC 280 can perform a centralized electric power management process for efficiently supplying electric power between the radiation source device 18 and the cassette 12. Inasmuch as electric power can be collected from one or more radiation source devices 18 and one or more cassettes 12 into the PC 280, the PC 280 can perform a battery function that enables efficient electric power management, so as to avoid power supply problems such as sudden power supply interruptions at times when electric power needs to be supplied to the radiation source device 18 and the cassette 12.

In each of the first radiographic image capturing apparatus 10A, the second radiographic image capturing apparatus 10B, and the third radiographic image capturing apparatus 10C, in order to determine whether the distance between the radiation source device 18 and the cassette 12, the distance between the radiation source device 18 and the PC 280, the distance between the cassette 12 and the PC 280, or distances between the radiation source device 18, the cassette 12, and the PC 280 are equal to or less than the reference distance, the radiation source device 18, the cassette 12, and the PC 280 may contain respective GPS receivers including GPS antennas therein, and such distances may be determined from the positions of the radiation source device 18, the cassette 12, and the PC 280, which are detected based on signals from the GPS receivers.

Although certain preferred embodiments of the present invention have been shown and described in detail, it should be understood that various changes and modifications may be made to the embodiments without departing from the scope of the invention as set forth in the appended claims.

Figure 48:
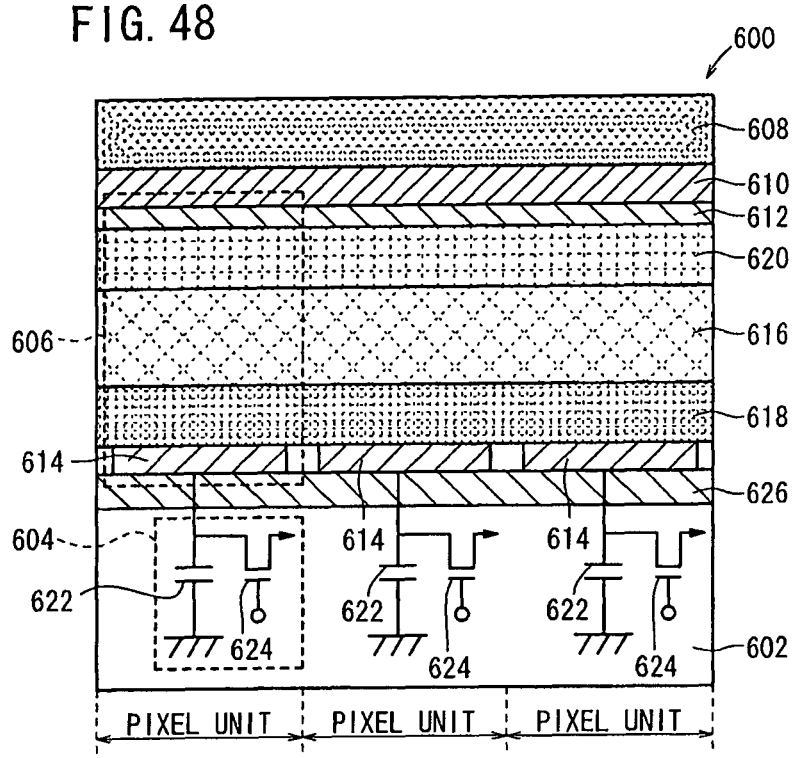
FIG. 48 is a cross-sectional view schematically illustrating the structure of three pixel units of a radiation detector according to a modified example of the invention.
Figure 49:
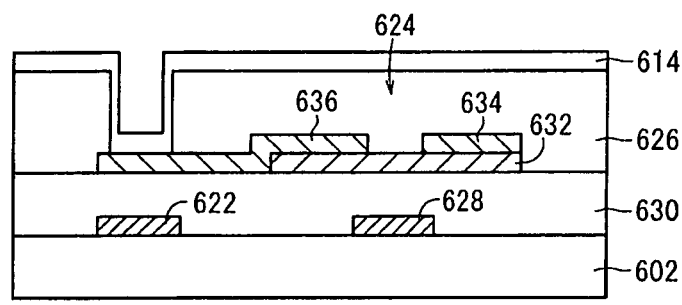
FIG. 49 is a view schematically illustrating the structure of a TFT and a charge storage unit shown in FIG. 48.

For example, the radiation detector 86 may be a radiation detector 600 according to a modified example shown in FIGS. 48 and 49. FIG. 48 is a cross-sectional view schematically illustrating the structure of three pixel units of the radiation detector 600 according to a modified example of the invention.

The radiation detector 600 includes a signal output unit 604, a sensor unit (photoelectric converter) 606, and a scintillator 608 that are sequentially laminated on an insulating substrate 602. The signal output unit 604 and the sensor unit 606 form a pixel unit. Plural pixel units are arranged in a matrix on the substrate 602, such as an array of pixel units arranged in rows and columns. In each pixel unit, the signal output unit 604 and the sensor unit 606 are arranged so as to overlap each other.

The scintillator 608 is formed on the sensor unit 606 with a transparent insulating film 610 interposed therebetween, and has a phosphor film that converts radiation 46 incident from the upper side (the side opposite to the substrate 602) into light and emits the light. It is preferable that the wavelength range of light emitted by the scintillator 608 be a visible light range (wavelength of 360 nm to 830 nm). It is more preferable that the wavelength range of light include a green wavelength range in order to capture a monochromatic image using the radiation detector 600.

Specifically, in a case in which imaging is performed using X-rays as radiation 46, it is preferable that the phosphor used for the scintillator 608 include cesium iodide (CsI). It is more preferable to use CsI(Tl) (thallium-added cesium iodide) having an emission spectrum of 420 nm to 700 nm during the emission of X-rays. The emission peak wavelength of CsI(Tl) in the visible light range is 565 nm.

The scintillator 608, for example, may be formed on a vapor deposition substrate by vapor deposition of a columnar crystal of CsI(Tl). As such, in a case in which the scintillator 608 is formed by vapor deposition, an Al plate is generally used as the vapor deposition substrate in terms of the transmittance of X-rays and manufacturing costs, but the vapor deposition substrate is not limited to the Al plate. In a case in which GOS is used as the scintillator 608, GOS may be applied onto the surface of a TFT active matrix substrate to form the scintillator 608, without using the vapor deposition substrate. Alternatively, after the scintillator 608 is formed by applying GOS to a resin base, the scintillator 608 may be attached to a TFT active matrix substrate. In this case, even if the application of GOS failed, the TFT active matrix substrate would not be damaged.

The sensor unit 606 includes an upper electrode 612, a lower electrode 614, and a photoelectric conversion film 616 provided between the upper and lower electrodes 612, 614.

The upper electrode 612 needs to make light generated by the scintillator 608 incident on the photoelectric conversion film 616. Therefore, it is preferable that the upper electrode 612 be made of a conductive material that is at least transparent with respect to the emission wavelength of the scintillator 608. Specifically, it is preferable that the upper electrode 612 be made of a transparent conducting oxide (TCO) having high transmittance with respect to visible light and a small resistance value. A metal thin film, such as an Au thin film, may be used as the upper electrode 612. However, when the transmittance increases to 90% or more, the resistance value is likely to increase. Therefore, it is preferable that the upper electrode 612 be made of TCO. For example, it is preferable that the upper electrode 612 be made of ITO, IZO, AZO, FTO, $SnO_2$, $TiO_2$, $ZnO_2$, etc. It is most preferable that the upper electrode 612 be made of ITO in terms of a simple process, low resistance, and transparency. One upper electrode 612 may be common to all pixel units, or the upper electrode 612 may be divided for each pixel unit.

The photoelectric conversion film 616 includes an organic photoconductor (OPC) and absorbs light emitted from the scintillator 608 and generates a charge corresponding to the absorbed light. When the photoelectric conversion film 616 includes an organic photoconductor (an organic photoelectric conversion material), it has a narrow absorption spectrum in the visible light range and absorbs little electromagnetic waves other than the light emitted from the scintillator 608. Therefore, it is possible to effectively reduce noise generated due to the absorption of radiation 46 by the photoelectric conversion film 616. For example, the photoelectric conversion film 616 may include amorphous silicon instead of an organic photoconductor. When the photoelectric conversion film 616 includes amorphous silicon, it has a wide absorption spectrum and can absorb light emitted from the scintillator 608 efficiently.

It is preferable that the absorption peak wavelength of the organic photoconductor forming the photoelectric conversion film 616 be close to the emission peak wavelength of the scintillator 608 in order to most effectively absorb light emitted from the scintillator 608. It is ideal that the absorption peak wavelength of the organic photoconductor is equal to the emission peak wavelength of the scintillator 608. However, when the difference between the absorption peak wavelength and the emission peak wavelength is small, it is possible to sufficiently absorb light emitted from the scintillator 608. Specifically, the difference between the absorption peak wavelength of the organic photoconductor and the emission peak wavelength of the scintillator 608 with respect to the radiation 46 is preferably equal to or less than 10 nm and more preferably, equal to or less than 5 nm.

Examples of the organic photoconductor capable of satisfying the above-mentioned conditions include a quinacridone-based organic compound and a phthalocyanine-based organic compound. For example, the absorption peak wavelength of quinacridone in the visible light range is 560 nm. Therefore, when quinacridone is used as the organic photoconductor and CsI(Tl) is used as the material forming the scintillator 608, it is possible to reduce the difference between the peak wavelengths to 5 nm or less and substantially maximize the amount of charge generated by the photoelectric conversion film 616.

The sensor unit 606 includes an organic layer that is formed by laminating or mixing, for example, an electromagnetic wave absorption portion, a photoelectric conversion portion, an electron transport portion, a hole transport portion, an electron blocking portion, a hole blocking portion, a crystallization prevention portion, an electrode, and an interlayer contact improvement portion. It is preferable that the organic layer include an organic p-type compound (organic p-type semiconductor) or an organic n-type compound (organic n-type semiconductor).

The organic p-type semiconductor is a donor-type organic semiconductor (compound) whose representative example is a hole-transport-type organic compound and means an organic compound which readily donates electrons. Specifically, in a case in which two organic materials are in contact with each other during use, one organic compound with low ionization potential is the organic p-type semiconductor. Therefore, any organic compound may be used as the donor-type organic compound as long as it has an electron donating property.

The organic n-type semiconductor is an acceptor-type organic semiconductor (compound) whose representative example is an electron-transport-type organic compound and means an organic compound which readily accepts electrons. Specifically, in a case in which two organic compounds are in contact with each other during use, one organic compound with high electron affinity is the organic n-type semiconductor. Therefore, any organic compound may be used as the acceptor-type organic compound as long as it has an electron accepting property.

Materials applicable to the organic p-type semiconductor and the organic n-type semiconductor and the structure of the photoelectric conversion film 616 have been described in detail in Japanese Laid-Open Patent Publication No. 2009-032854 and thus a detailed description thereof will be omitted. The photoelectric conversion film 616 may include fullerene or carbon nanotubes.

It is preferable that the thickness of the photoelectric conversion film 616 be as large as possible in terms of the absorption of light from the scintillator 608. However, when the thickness of the photoelectric conversion film 616 is greater than a predetermined value, the intensity of the electric field of the photoelectric conversion film 616 generated by the bias voltage applied from both ends of the photoelectric conversion film 616 is reduced, which makes it difficult to collect charge. Therefore, the thickness of the photoelectric conversion film 616 is preferably from 30 nm to 300 nm, more preferably from 50 nm to 250 nm, and most preferably from 80 nm to 200 nm.

One photoelectric conversion film 616 is common to all pixel units. However, the photoelectric conversion film 616 may be divided for each pixel unit. The lower electrode 614 is a thin film that is divided for each pixel unit. However, one lower electrode 614 may be common to all pixel units. The lower electrode 614 may be appropriately made of a transparent or opaque conductive material, such as aluminum or silver. The thickness of the lower electrode 614 may be, for example, from 30 nm to 300 nm.

In the sensor unit 606, a predetermined bias voltage can be applied between the upper electrode 612 and the lower electrode 614 to move one of the charges (a hole and an electron) generated from the photoelectric conversion film 616 to the upper electrode 612 and move the other charge to the lower electrode 614. In the radiation detector 600 according to this modified example, a wiring line is connected to the upper electrode 612 and the bias voltage is applied to the upper electrode 612 through the wiring line. It is assumed that the polarity of the bias voltage is determined such that the electron generated in the photoelectric conversion film 616 is moved to the upper electrode 612 and the hole is moved to the lower electrode 614. However, the polarity may be reversed.

The sensor unit 606 forming each pixel unit may include at least the lower electrode 614, the photoelectric conversion film 616, and the upper electrode 612. In order to prevent an increase in dark current, it is preferable that at least one of electron blocking film 618 and hole blocking film 620 be provided, and it is more preferable that both the electron blocking film 618 and the hole blocking film 620 be provided.

The electron blocking film 618 may be provided between the lower electrode 614 and the photoelectric conversion film 616. In a case in which the bias voltage is applied between the lower electrode 614 and the upper electrode 612, it is possible to prevent an increase in the dark current due to the injection of electrons from the lower electrode 614 into the photoelectric conversion film 616.

The electron blocking film 618 may be made of an electron donating organic material. In practice, the material used for the electron blocking film 618 may be selected according to a material forming an adjacent electrode and a material forming an adjacent photoelectric conversion film 616. It is preferable that the material used for the electron blocking film 618 have an electron affinity (Ea) that is at least 1.3 eV higher than the work function (Wf) of the material forming the adjacent electrode and have an ionization potential (Ip) equal to or less than that of the material forming the adjacent photoelectric conversion film 616. Materials applicable as the electron donating organic material have been described in detail in Japanese Laid-Open Patent Publication No. 2009-032854 and thus a detailed description thereof will be omitted.

The thickness of the electron blocking film 618 is preferably from 10 nm to 200 nm, more preferably from 30 nm to 150 nm, and most preferably from 50 nm to 100 nm in order to reliably obtain the effect of preventing the dark current and prevent a reduction in the photoelectric conversion efficiency of the sensor unit 606.

The hole blocking film 620 may be provided between the photoelectric conversion film 616 and the upper electrode 612. In a case in which the bias voltage is applied between the lower electrode 614 and the upper electrode 612, it is possible to prevent an increase in the dark current due to the injection of holes from the upper electrode 612 into the photoelectric conversion film 616.

The hole blocking film 620 may be made of an electron accepting organic material. The thickness of the hole blocking film 620 is preferably from 10 nm to 200 nm, more preferably from 30 nm to 150 nm, and most preferably from 50 nm to 100 nm in order to reliably obtain the effect of preventing the dark current and prevent a reduction in the photoelectric conversion efficiency of the sensor unit 606.

In practice, the material used for the hole blocking film 620 may be selected according to a material forming an adjacent electrode and a material forming an adjacent photoelectric conversion film 616. It is preferable that the material used for the hole blocking film 620 have an ionization potential (Ip) that is at least 1.3 eV higher than the work function (Wf) of the material forming the adjacent electrode and have an electron affinity (Ea) equal to or more than that of the material forming the adjacent photoelectric conversion film 616. Materials applicable as the electron accepting organic material have been described in detail in Japanese Laid-Open Patent Publication No. 2009-032854 and thus a detailed description thereof will be omitted.

In a case in which the bias voltage is set such that, among the charges generated in the photoelectric conversion film 616, holes are moved to the upper electrode 612 and electrons are moved to the lower electrode 614, the positions of the electron blocking film 618 and the hole blocking film 620 may be reversed. In addition, it is not necessary to provide both the electron blocking film 618 and the hole blocking film 620. When either the electron blocking film 618 or the hole blocking film 620 is provided, it is possible to a certain extent to obtain the effect of preventing the dark current.

As shown in FIG. 49, the signal output unit 604 is provided on the surface of the substrate 602 so as to correspond to the lower electrode 614 of each pixel unit. The signal output unit 604 has a storage capacitor 622 that stores the charge moved to the lower electrode 614, and a TFT 624 that converts the charge stored in the storage capacitor 622 into an electric signal and outputs the electric signal. A region in which the storage capacitor 622 and the TFT 624 are formed has a portion that overlaps the lower electrode 614 in a plan view. In this way, the signal output unit 604 and the sensor unit 606 in each pixel unit overlap each other in the thickness direction. It is possible to minimize the plane area of the radiation detector 600 (pixel unit), when the signal output unit 604 is formed such that the storage capacitor 622 and the TFT 624 are completely covered with the lower electrode 614.

The storage capacitor 622 is electrically connected to the corresponding lower electrode 614 through a conductive line that is formed so as to pass through an insulating film 626 provided between the substrate 602 and the lower electrode 614. In this way, it is possible to move the charge captured by the lower electrode 614 to the storage capacitor 622.

The TFT 624 is formed by laminating a gate electrode 628, a gate insulating film 630, and an active layer (channel layer) 632 and providing a source electrode 634 and a drain electrode 636 on the active layer 632 with a predetermined gap therebetween. The active layer 632 may be made of, for example, amorphous silicon, an amorphous oxide, an organic semiconductor material, or carbon nanotubes. The material forming the active layer 632 is not limited thereto.

An oxide (for example, an In—O-based oxide) including at least one of In, Ga, and Zn is preferable as the amorphous oxide that can form the active layer 632. An oxide (for example, an In—Zn—O-based oxide, an In—Ga—O-based oxide, or a Ga—Zn—O-based oxide) including at least two of In, Ga, and Zn is more preferable as the amorphous oxide. An oxide including In, Ga, and Zn is most preferable as the amorphous oxide. As an In—Ga—Zn—O-based amorphous oxide, an amorphous oxide having a composition represented by $InGaO_3(ZnO)_m$ (m is a natural number smaller than 6) in a crystalline state is preferable, and $InGaZnO_4$ is more preferable. The amorphous oxide that can form the active layer 632 is not limited thereto.

A phthalocyanine compound, pentacene, or vanadyl phthalocyanine may be given as an example of the organic semiconductor material that can form the active layer 632, but the organic semiconductor material is not limited thereto. The structure of the phthalocyanine compound has been described in detail in Japanese Laid-Open Patent Publication No. 2009-212389 and thus a detailed description thereof will be omitted.

When the active layer 632 of the TFT 624 is made of an amorphous oxide, an organic semiconductor material, or carbon nanotubes, radiation 46, such as X-rays, is not absorbed. Even if the radiation 46 is absorbed, the absorbed amount will be very small. Therefore, it is possible to effectively prevent the generation of noise in the signal output unit 604.

In a case in which the active layer 632 is made of carbon nanotubes, it is possible to improve the switching speed of the TFT 624 and form the TFT 624 with low light absorptance in the visible light range. In addition, in a case in which the active layer 632 is made of carbon nanotubes, even though a very small amount of metallic impurities is mixed with the active layer 632, the performance of the TFT 624 is significantly reduced. Therefore, it is necessary to separate and extract carbon nanotubes with very high purity using, for example, centrifugal separation and form the active layer 632 with the carbon nanotubes.

All of the amorphous oxide, the organic semiconductor material, the carbon nanotubes, and the organic photoconductor can be used to form a film at a low temperature. Thus, the substrate 602 is not limited to a substrate with high heat resistance, such as a semiconductor substrate, a quartz substrate, or a glass substrate, but a flexible substrate, such as a plastic substrate, an aramid substrate, or a bio-nanofiber substrate may be used as the substrate 602. Specifically, for example, a flexible substrate made of the following materials may be used: polyester, such as polyethylene terephthalate, polybutylene phthalate, or polyethylene naphthalate, polystyrene, polycarbonate, polyether sulfone, polyarylate, polyimide, polycycloolefin, norbornene resin, and polychlorotrifluoroethylene. When such a flexible substrate made of plastic is used, it is possible to reduce the weight of the substrate. For example, this structure has an advantage in portability.

When the photoelectric conversion film 616 is formed of the organic photoconductor and the TFT 624 is formed of the organic semiconductor material, it is possible to form films of the photoelectric conversion film 616 and the TFT 624 at a low temperature with respect to a flexible substrate (substrate 602) of plastic. Also, it is possible to reduce the thickness and weight of the radiation detector 600 in its entirety, and thereby it is possible to reduce the thickness and weight of the cassette 12 housing the radiation detector 600. Accordingly, it is possible to improve convenience when used outside of a hospital. Further, a base material of the photoelectric conversion unit is made of a flexible material instead of glass that is commonly used. Thus, it is possible to enhance resistance to damage or the like when the radiographic image capturing apparatus is carried or used.

In addition, for example, an insulating layer for ensuring an insulating property, a gas barrier layer for preventing the penetration of water or oxygen, and an undercoating layer for improving flatness or the adhesion of, for example, the electrode may be provided on the substrate 602.

Since aramid can be applied to a high-temperature process of 200 degrees or more, a transparent electrode material can be cured at a high temperature to have low resistance, and the aramid can respond to the automatic mounting of a driver IC including a solder reflow process. In addition, the thermal expansion coefficient of aramid is close to that of ITO (indium tin oxide) or a glass substrate. Therefore, after an aramid substrate is manufactured, the warping of the aramid substrate is small and the aramid substrate is less likely to be cracked. In addition, aramid is capable of forming a substrate thinner than, for example, a glass substrate. Aramid may be laminated on a super-thin glass substrate to form the substrate 602.

The bio-nanofiber is a composite of a cellulose microfibril bundle (bacterial cellulose) generated by bacteria (Acetobacter, Acetobacter Xylinum) and a transparent resin. The cellulose microfibril bundle has a width of 50 nm, a size of one-tenth of the visible light wavelength, high strength, high elasticity, and a low thermal expansion coefficient. A transparent resin, such as an acrylic resin or an epoxy resin, is impregnated into the bacterial cellulose and is then cured to obtain bio-nanofiber that has a light transmittance of about 90% at a wavelength of 500 nm while including 60 to 70% of fiber. The bio-nanofiber has a low thermal expansion coefficient (3 to 7 ppm) equal to that of a silicon crystal, strength (460 MPa) similar to that of steel, high elasticity (30 GPa), and flexibility. Therefore, the bio-nanofiber is capable of forming a substrate 602 thinner than, for example, a glass substrate.

In this example, the signal output unit 604, the sensor unit 606, and the transparent insulating film 610 are sequentially formed on the substrate 602 and the scintillator 608 is bonded to the substrate 602 by an adhesive resin with low light absorptance, thereby forming the radiation detector 600.

In the radiation detector 600 according to the modified example, since the photoelectric conversion film 616 is made of an organic photoconductor and the active layer 632 of the TFT 624 is made of the organic semiconductor material, radiation 46 is hardly absorbed by the photoelectric conversion film 616 or the signal output unit 604. Therefore, it is possible to prevent a reduction in sensitivity for the radiation 46.

Both the organic semiconductor material forming the active layer 632 of the TFT 624 and the organic photoconductor forming the photoelectric conversion film 616 can be used to form a film at a low temperature. Therefore, the substrate 602 can be made of a plastic resin, aramid, or bio-nanofiber that absorbs a small amount of radiation 46. Accordingly, it is possible to prevent a reduction in sensitivity for the radiation 46.

For example, in a case in which the radiation detector 600 is adhered to the irradiated surface 20 of the housing and the substrate 602 is made of a plastic resin with high rigidity, aramid, or bio-nanofiber, it is possible to reduce the thickness of the irradiated surface 20 of the housing since the radiation detector 600 has high rigidity. In addition, in a case in which the substrate 602 is made of a plastic resin, aramid, or bio-nanofiber having high rigidity, the radiation detector 600 has flexibility. In case the substrate 602 is made of a plastic resin, aramid, or bio-nanofiber having high rigidity, even when an impact is applied to the irradiated surface 20, the radiation detector 600 is less likely to be damaged due to its flexibility.

The radiation detector 600 according to the modified example is a so-called rear surface reading type (so-called PSS (Penetration Side Sampling) type) in which the light emitted from the scintillator 608 is converted by the sensor unit 606 (photoelectric conversion film 616) into the electric charge for reading the radiographic image, while the sensor unit 606 is positioned on the side opposite to the radiation source 44. The type of the radiation detector, however, is not limited thereto.

For example, a radiation detector may be a so-called front surface reading type (so-called ISS (Irradiation Side Sampling) type). In this case, the insulating substrate 602, the signal output unit 604, the sensor unit 606, and the scintillator 608 are successively laminated along an irradiation direction of the radiation 46. The light emitted from the scintillator 608 is converted by the sensor unit 606 into the electric charge for reading the radiographic image, while the sensor unit 606 is positioned on the same side as the radiation source 44. Usually, the scintillator 608 emits light having higher intensity on a radiation-irradiated side by the radiation 46 than a back side. Therefore, in the radiation detector of the front surface reading type, the distance from the scintillator 608 to the photoelectric conversion film 616, by which emitted light travels, can be shorter than in the radiation detector 600 of the rear surface reading type. Thus, it is possible to reduce the diffusion or attenuation of the light. As a result, the resolution of the radiographic image can be higher.

What is claimed is:

1. A radiographic image capturing apparatus comprising:
   a radiation source device including a radiation source for outputting radiation; and
   a detector device including a radiation detector for detecting radiation that is transmitted through a subject when the subject is irradiated with radiation by the radiation source, and converting the detected radiation into a radiographic image;
   at least one of the radiation source device and the detector device having an electric power supply limiting unit for limiting supply of electric power;
   the electric power supply limiting unit comprising:
   an activator/deactivator for determining activation or deactivation of supply of electric power between the radiation source device and the detector device, based on a present position of a corresponding one of the radiation source device and the detector device, or based on a distance between the radiation source device and the detector device; and
   an electric power supply activator for enabling supply of electric power between the radiation source device and the detector device, if the activator/deactivator determines activation of supply of electric power between the radiation source device and the detector device.

2. The radiographic image capturing apparatus according to claim 1, wherein the activator/deactivator comprises:
   a present position acquirer for acquiring the present position of the corresponding one of the radiation source device and the detector device; and
   a determiner for determining whether or not the acquired present position is outside of a medical organization,
   wherein the electric power supply activator enables supply of electric power between the radiation source device and the detector device, if the determiner judges that the acquired present position is outside of the medical organization.

3. The radiographic image capturing apparatus according to claim 2,
   wherein each of the radiation source device and the detector device is provided with a corresponding said electric power supply limiting unit, and wherein the electric power supply activator of each corresponding said electric power supply limiting unit enables the supply of electric power between the radiation source device and the detector device, if the determiner judges that the acquired present position is outside of the medical organization.

4. The radiographic image capturing apparatus according to claim 2, wherein the activator/deactivator deactivates supply of electric power between the radiation source device and the detector device, if the determiner judges that the acquired present position is within the medical organization.

5. The radiographic image capturing apparatus according to claim 1, wherein the activator/deactivator comprises:
a present position acquirer for acquiring the present position of the corresponding one of the radiation source device and the detector device; and
a determiner for determining whether or not the acquired present position is in a preset location,
wherein the electric power supply activator enables supply of electric power between the radiation source device and the detector device, if the determiner judges that the acquired present position is in the preset location.

6. The radiographic image capturing apparatus according to claim 5,
wherein each of the radiation source device and the detector device is provided with a corresponding said electric power supply limiting unit, and
wherein the electric power supply activator of each corresponding said electric power supply limiting unit enables the supply of electric power between the radiation source device and the detector device, if the determiner judges that the acquired present position is in the preset location.

7. The radiographic image capturing apparatus according to claim 5, wherein the activator/deactivator deactivates supply of electric power between the radiation source device and the detector device, if the determiner judges that the acquired present position is not in the preset location.

8. The radiographic image capturing apparatus according to claim 1, wherein the activator/deactivator comprises:
a determiner for determining whether or not the distance between the radiation source device and the detector device satisfies a certain condition,
wherein the electric power supply activator enables supply of electric power between the radiation source device and the detector device, if the determiner judges that the distance satisfies the certain condition.

9. The radiographic image capturing apparatus according to claim 8, wherein the activator/deactivator deactivates supply of electric power between the radiation source device and the detector device, if the determiner judges that the distance does not satisfy the certain condition.

10. The radiographic image capturing apparatus according to claim 8, wherein the certain condition is that a linear distance between the radiation source device and the detector device is equal to or less than a preset reference distance.

11. The radiographic image capturing apparatus according to claim 8, further comprising:
a controller for controlling at least the radiation source device and the detector device,
wherein the determiner determines whether or not the distance between at least two of the radiation source device, the detector device, and the controller satisfies the certain condition, and
the electric power supply activator enables supply of electric power between the at least two of the radiation source device, the detector device, and the controller, if the determiner judges that the distance satisfies the certain condition.

12. The radiographic image capturing apparatus according to claim 11, wherein the activator/deactivator deactivates supply of electric power between the at least two of the radiation source device, the detector device, and the controller, if the determiner judges that the distance does not satisfy the certain condition.

13. The radiographic image capturing apparatus according to claim 11, wherein the certain condition is that a linear distance between the at least two of the radiation source device, the detector device, and the controller is equal to or less than a preset reference distance.

14. The radiographic image capturing apparatus according to claim 1, wherein the electric power supply limiting unit further comprises an electric power controller activatable by the electric power supply activator based on an electric power supply request, for supplying electric power only along a route from the radiation source device to the detector device.

15. The radiographic image capturing apparatus according to claim 14, further comprising:
an electric power storage unit of the radiation source device; and
an electric power storage unit of the detector device;
wherein the electric power controller supplies the electric power from the electric power storage unit of the radiation source device to the electric power storage unit of the detector device.

16. The radiographic image capturing apparatus according to claim 15,
wherein the electric power storage unit of the radiation source device comprises a battery for supplying electric power to the radiation source; and
the electric power storage unit of the detector device comprises a built-in capacitor for supplying electric power to the radiation detector.

17. The radiographic image capturing apparatus according to claim 1, wherein the electric power supply limiting unit further comprises:
an electric power controller activatable by the electric power supply activator based on an electric power supply request, for supplying electric power only along a route from the detector device to the radiation source device.

18. The radiographic image capturing apparatus according to claim 17, further comprising:
an electric power storage unit of the detector device; and
an electric power storage unit of the radiation source device;
wherein the electric power controller supplies the electric power from the electric power storage unit of the detector device to the electric power storage unit of the radiation source device.

19. The radiographic image capturing apparatus according to claim 18, wherein the electric power storage unit of the radiation source device comprises a built-in capacitor for supplying electric power to the radiation source; and
the electric power storage unit of the detector device comprises a battery for supplying electric power to the radiation detector.

20. The radiographic image capturing apparatus according to claim 1, wherein the electric power supply limiting unit further comprises:
an electric power controller activatable by the electric power supply activator;

the electric power controller including an electric power manager for managing electric power required to capture a given number of radiographic images, and supplying required electric power flexibly to at least one of the radiation source device and the detector device, wherein the electric power manager supplies electric power from one of the radiation source device and the detector device, which has excessive electric power with respect to the required electric power, to the other of the radiation source device and the detector device, which has insufficient electric power with respect to the required electric power, up to the required electric power.

21. The radiographic image capturing apparatus according to claim 1, wherein the electric power supply limiting unit further comprises an electric power controller activatable by the electric power supply activator based on an electric power supply request made before an image capturing process, for supplying electric power between the radiation source device and the detector device.

22. The radiographic image capturing apparatus according to claim 21, wherein the electric power controller deactivates supply of electric power between the radiation source device and the detector device from a start of the image capturing process after electric power has been supplied and until an electric power supply request is given before a next image capturing process.

23. The radiographic image capturing apparatus according to claim 1, wherein the electric power supply limiting unit further comprises an electric power controller for supplying electric power between the radiation source device and the detector device; and an electric power supply limiter for limiting supply of the electric power by the electric power controller between the radiation source device and the detector device, during a period in which the radiographic image is being captured based on the radiation.

24. The radiographic image capturing apparatus according to claim 1, wherein the electric power supply limiting unit further comprises an electric power controller activatable by the electric power supply activator upon completion of an image capturing process, for supplying electric power between the radiation source device and the detector device.

25. The radiographic image capturing apparatus according to claim 1, further comprising:

a controller for controlling at least the radiation source device and the detector device;

the radiation source device including a first battery for supplying electric power to the radiation source;

the detector device including a second battery for supplying electric power to the radiation detector;

the controller including a third battery and an electric power supply limiting unit, which functions the same as the first-mentioned electric power supply limiting unit, wherein the electric power supply activator of the electric power supply limiting unit of at least the controller enables supply of electric power between the first battery, the second battery, and the third battery, if the activator/deactivator of the electric power supply limiting unit determines activation of supply of electric power between the radiation source device and the detector device.

26. The radiographic image capturing apparatus according to claim 25, wherein the electric power supply limiting unit of the controller includes an electric power controller activatable by the electric power supply activator based on an electric power supply request made before an image capturing process or upon completion of the image capturing process, for supplying electric power from the third battery to the first battery.

27. The radiographic image capturing apparatus according to claim 25, wherein the electric power supply limiting unit of the controller includes an electric power controller activatable by the electric power supply activator based on an electric power supply request made before an image capturing process or upon completion of the image capturing process, for supplying electric power from the third battery to the second battery.

28. The radiographic image capturing apparatus according to claim 26, wherein the controller includes an electric power collector for collecting electric power from at least one of the first battery and the second battery into the third battery.

29. The radiographic image capturing apparatus according to claim 1, the radiation detector comprising:

a scintillator;

a photoelectric converter for absorbing light converted by the scintillator and generating a charge corresponding to the absorbed light; and a signal output unit for outputting an electric signal that corresponds to radiographic image information, for the charge generated by the photoelectric converter, wherein the photoelectric converter includes an organic photoconductor, and the signal output unit includes a channel layer that comprises an organic semiconductor material.

30. A radiographic image capturing system comprising:

a radiation source device including a radiation source for outputting radiation;

a detector device including a radiation detector for detecting radiation that is transmitted through a subject when the subject is irradiated with radiation by the radiation source, and converting the detected radiation into a radiographic image;

an activator/deactivator for determining activation or deactivation of supply of electric power between the radiation source device and the detector device, based on a present position of at least one of the radiation source device and the detector device, or based on a distance between the radiation source device and the detector device; and an electric power supply activator for enabling supply of electric power between the radiation source device and the detector device, if the activator/deactivator determines activation of supply of electric power between the radiation source device and the detector device.

* * * * *